US008001963B2

(12) United States Patent
Giroux

(10) Patent No.: US 8,001,963 B2
(45) Date of Patent: Aug. 23, 2011

(54) INTEGRATED NEBULIZER AND PARTICLE DISPERSION CHAMBER FOR NASAL DELIVERY OF MEDICAMENT TO DEEP NASAL CAVITY AND PARANASAL SINUSES

(75) Inventor: Marc Giroux, Lynnwood, WA (US)

(73) Assignee: Kurve Technology, Inc., Lynnwood, WA (US)

( * ) Notice: Subject to any disclaimer, the term of this patent is extended or adjusted under 35 U.S.C. 154(b) by 1099 days.

(21) Appl. No.: 10/570,724

(22) PCT Filed: Sep. 3, 2004

(86) PCT No.: PCT/US2004/029001

§ 371 (c)(1),
(2), (4) Date: Feb. 8, 2007

(87) PCT Pub. No.: WO2005/023335

PCT Pub. Date: Mar. 17, 2005

(65) Prior Publication Data

US 2007/0131224 A1 Jun. 14, 2007

Related U.S. Application Data

(60) Provisional application No. 60/500,386, filed on Sep. 5, 2003, provisional application No. 60/581,296, filed on Jun. 19, 2004.

(51) Int. Cl.
*A61M 11/00* (2006.01)

(52) U.S. Cl. ......... 128/200.14; 128/203.12; 128/200.21; 128/203.15

(58) Field of Classification Search ............. 128/203.12, 128/200.21, 200.14, 207.18, 207.13, 203.15, 128/200.23, 204.12; 239/337–338
See application file for complete search history.

(56) References Cited

U.S. PATENT DOCUMENTS

| | | | |
|---|---|---|---|
| 2,819,716 | A | 1/1958 | Miller |
| 2,951,644 | A | 9/1960 | Mahon |
| 3,362,405 | A | 1/1968 | Hazel |
| 3,762,409 | A | 10/1973 | Lester |
| 3,858,615 | A | 1/1975 | Weigl |
| 4,119,096 | A | 10/1978 | Drews |

(Continued)

FOREIGN PATENT DOCUMENTS

| | | |
|---|---|---|
| EP | 0539674 | 5/1993 |

(Continued)

OTHER PUBLICATIONS

U.S. Appl. No. 60/500,386, filed Sep. 5, 2003, Giroux.

(Continued)

*Primary Examiner* — Justine R Yu
*Assistant Examiner* — Colin Stuart
(74) *Attorney, Agent, or Firm* — Barry L. Davison; Davis Wright Tremaine LLP

(57) ABSTRACT

Particular aspects provide a novel integrated nebulizer and particle dispersion chamber (12), and novel methods of using same. Preferably, the particle dispersion chamber (12) provides for delivery of a vortical flow of nebulized particles to the nostrils. The inventive integrated nebulizer, delivery methods and breathing techniques allow for delivering medicament into the deep nasal cavity and paranasal sinuses of a user. Significantly, the inventive devices and methods allow for systemic and topical delivery of medicaments via the membranes of the nasal cavity and paranasal sinuses. Additional preferred embodiments provide complementary cartridge docking system that allows for user-specific nebulized drug delivery.

26 Claims, 34 Drawing Sheets

U.S. PATENT DOCUMENTS

| | | | |
|---|---|---|---|
| 4,150,071 A | 4/1979 | Pecina | |
| 4,198,969 A | 4/1980 | Virag | |
| 4,299,784 A | 11/1981 | Hense | |
| 4,454,880 A | 6/1984 | Muto | |
| 4,461,425 A | 7/1984 | Miller | |
| 4,702,415 A | 10/1987 | Hughes | |
| 4,809,692 A | 3/1989 | Nowacki | |
| 4,809,706 A | 3/1989 | Watson | |
| 4,865,027 A | 9/1989 | Laanen | |
| 4,938,209 A | 7/1990 | Fry | |
| 4,953,545 A | 9/1990 | McCarty | |
| 4,972,830 A | 11/1990 | Wong | |
| RE33,642 E * | 7/1991 | Lester | 128/200.21 |
| RE33,717 E * | 10/1991 | Svoboda | 239/338 |
| 5,063,922 A | 11/1991 | Häkkinen | |
| 5,201,726 A | 4/1993 | Kirkham | |
| 5,203,323 A | 4/1993 | Tritle | |
| 5,241,954 A | 9/1993 | Glenn | |
| 5,287,847 A | 2/1994 | Piper | |
| 5,301,663 A | 4/1994 | Small | |
| 5,309,900 A | 5/1994 | Knoch | |
| 5,388,574 A | 2/1995 | Ingebrethsen | |
| 5,392,767 A | 2/1995 | Bianco | |
| 5,427,089 A | 6/1995 | Kraemer | |
| 5,435,282 A | 7/1995 | Haber | |
| 5,437,267 A | 8/1995 | Weinstein | |
| 5,458,135 A | 10/1995 | Patton | |
| 5,476,093 A | 12/1995 | Lankinen | |
| 5,479,920 A | 1/1996 | Piper | |
| 5,485,828 A | 1/1996 | Hauser | |
| 5,487,378 A | 1/1996 | Robertson | |
| 5,490,630 A | 2/1996 | Hecker | |
| 5,497,765 A | 3/1996 | Praud | |
| 5,497,944 A | 3/1996 | Weston | |
| 5,505,193 A | 4/1996 | Ballini | |
| 5,520,167 A | 5/1996 | Hamilton | |
| 5,577,497 A | 11/1996 | Mecikalski | |
| 5,584,285 A | 12/1996 | Salter | |
| 5,586,551 A | 12/1996 | Hilliard | |
| 5,588,564 A | 12/1996 | Hutson | |
| 5,685,291 A | 11/1997 | Marsh | |
| 5,687,912 A | 11/1997 | Denyer | |
| 5,724,965 A | 3/1998 | Handke | |
| 5,743,250 A | 4/1998 | Gonda | |
| 5,755,218 A | 5/1998 | Johansson | |
| 5,775,320 A | 7/1998 | Patton | |
| 5,785,049 A | 7/1998 | Smith | |
| 5,855,202 A | 1/1999 | Andrade | |
| RE36,070 E * | 2/1999 | Ballini et al. | 128/200.14 |
| 5,875,774 A | 3/1999 | Clementi | |
| 5,906,198 A | 5/1999 | Flickinger | |
| 5,950,623 A | 9/1999 | Michell | |
| 5,954,049 A | 9/1999 | Foley | |
| 6,062,214 A | 5/2000 | Howlett | |
| 6,073,629 A | 6/2000 | Hardy | |
| 6,076,520 A | 6/2000 | Cooper | |
| 6,085,740 A | 7/2000 | Ivri | |
| 6,085,741 A * | 7/2000 | Becker | 128/200.21 |
| 6,095,141 A | 8/2000 | Armer | |
| 6,112,746 A | 9/2000 | Kwok | |
| 6,119,694 A | 9/2000 | Correa | |
| 6,131,568 A | 10/2000 | Denyer | |
| 6,158,428 A | 12/2000 | Mecikalski | |
| 6,192,876 B1 | 2/2001 | Denyer | |
| 6,202,643 B1 | 3/2001 | Sladek | |
| 6,223,744 B1 | 5/2001 | Garon | |
| 6,234,459 B1 | 5/2001 | Rock | |
| 6,240,917 B1 | 6/2001 | Andrade | |
| 6,244,573 B1 | 6/2001 | Rock | |
| 6,338,443 B1 | 1/2002 | Piper | |
| 6,347,629 B1 | 2/2002 | Braithwaite | |
| 6,363,932 B1 * | 4/2002 | Forchione et al. | 128/203.12 |
| 6,367,471 B1 | 4/2002 | Genosar | |
| 6,394,085 B1 | 5/2002 | Hardy | |
| 6,412,488 B1 | 7/2002 | Barnett | |
| 6,418,925 B1 | 7/2002 | Genova | |
| 6,470,882 B1 | 10/2002 | Newhouse | |
| 6,550,472 B2 | 4/2003 | Litherland | |
| 6,576,224 B1 | 6/2003 | Osbakken | |
| 6,651,655 B1 | 11/2003 | Licalsi | |
| 6,702,997 B2 | 3/2004 | Chaudry | |
| 6,749,597 B2 | 6/2004 | Frank | |
| 6,796,513 B2 | 9/2004 | Fraccaroli | |
| 6,810,872 B1 | 11/2004 | Ohki | |
| RE38,700 E | 2/2005 | Briggs, III | |
| 6,851,626 B2 | 2/2005 | Patel | |
| 6,883,517 B2 | 4/2005 | Halamish | |
| 6,948,491 B2 | 9/2005 | Loeffler | |
| 6,994,083 B2 | 2/2006 | Foley | |
| 2002/0124843 A1 | 9/2002 | Skiba | |
| 2003/0078551 A1 | 4/2003 | Hochrainer | |
| 2003/0183222 A9 * | 10/2003 | Ganan-Calvo | 128/200.14 |
| 2004/0025871 A1 | 2/2004 | Davies | |
| 2004/0164099 A1 | 8/2004 | Diestelhorst | |

FOREIGN PATENT DOCUMENTS

| | | | |
|---|---|---|---|
| EP | 0734719 | | 10/1996 |
| EP | 0747078 | | 12/1996 |
| GB | 1069048 | | 5/1967 |
| JP | 8280809 | | 10/1996 |
| WO | WO 98/26827 | | 6/1998 |
| WO | WO 99/47273 | | 9/1999 |
| WO | WO 01/02024 | | 1/2001 |
| WO | WO 01/36033 | | 5/2001 |
| WO | WO 01/49350 | | 7/2001 |
| WO | WO 02/026299 | * | 4/2002 |
| WO | WO 03/026559 | | 4/2003 |
| WO | WO 2005/023335 | | 3/2005 |

OTHER PUBLICATIONS

U.S. Appl. No. 60/581,296, filed Jun. 19, 2004, Giroux.
Hess et al., "Medication Nebulizer Performance," Chest, 2006, pp. 498-505, vol. 110.
Hess, "Nebulizers: Principles and Performance," Respiratory Care, 2000, pp. 609-622, vol. 45.
Loffert et al., "A Comparison of Commercial Jet Nebulizers," Chest, 1994, pp. 1788-1792, vol. 106.
O'Callaghan et al., "The science of nebulised drug delivery," Thorax, 1997, pp. S31-S44, vol. 52, Supplement 2.
Zhao et al., "Effect of Anatomy of Human Nasal Air flow and Odorant Transport Patterns: Implications for Olfaction," Chemical Senses, 2004, pp. 365-379, vol. 29.

* cited by examiner

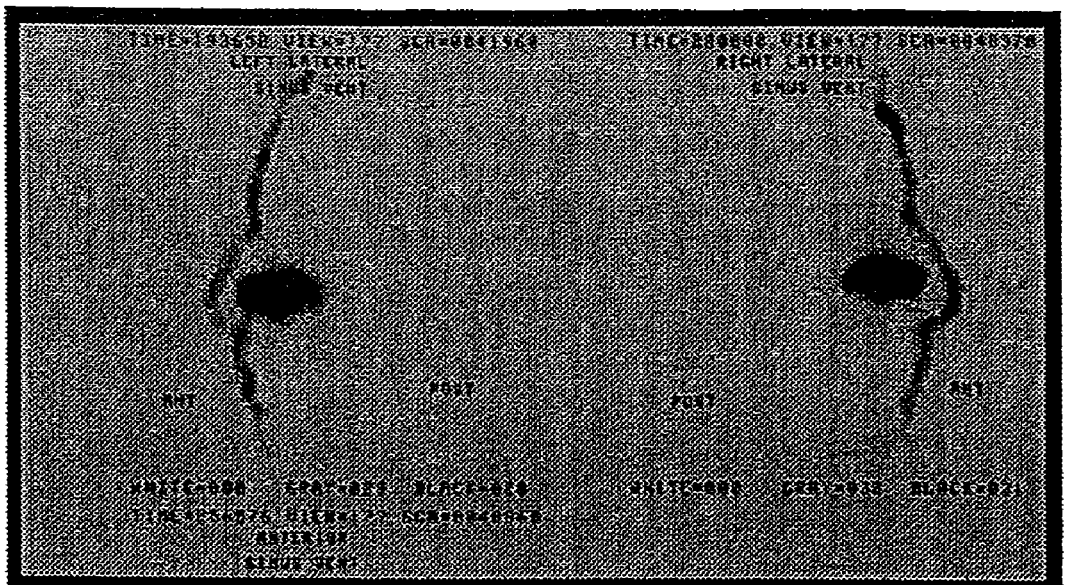
Fig. 21 Drug delivery using the current technology. The drug does not penetrate the sinuses and remains in the nasal cavity. Note the limited exposure and absorption area.
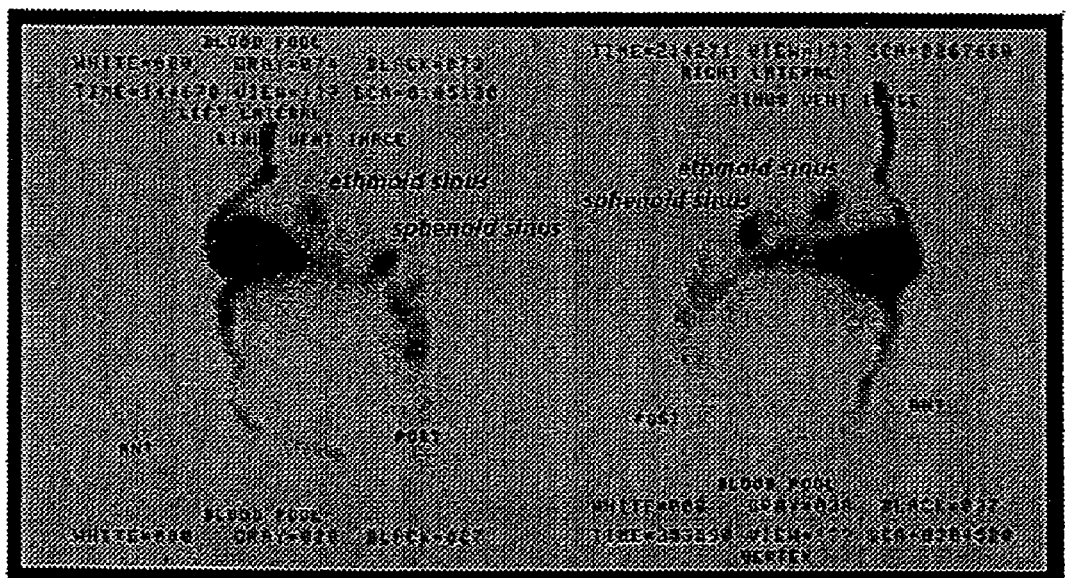

Fig. 22 Drug delivery using the NebuNase device. The exposed area is significantly larger with more absorption area. Most notably, the drug penetrated the ethmoid and sphenoid sinus. The sphenoid sinus is located farthest from the nasal cavity. These areas have not been penetrated at any time using the current technology. This is a significant breakthrough in intranasal drug delivery.

Please note the drug path leading to the throat. This was created in the breathing cycle and leads to the lungs where it will be further absorbed.

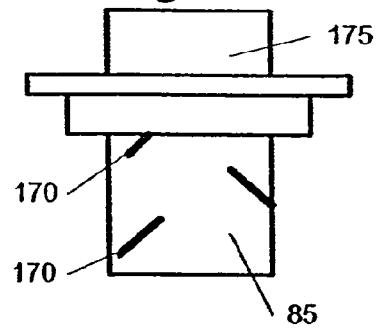
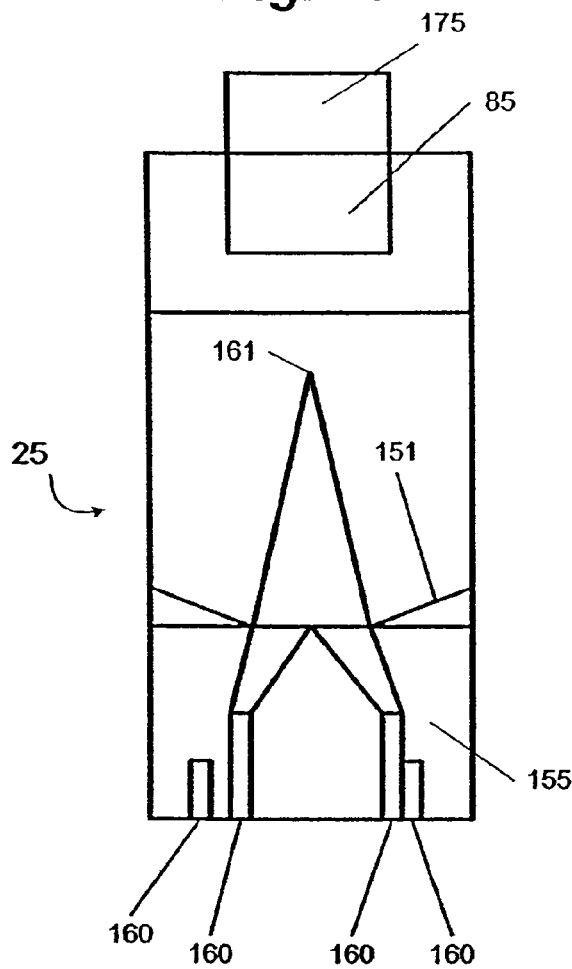
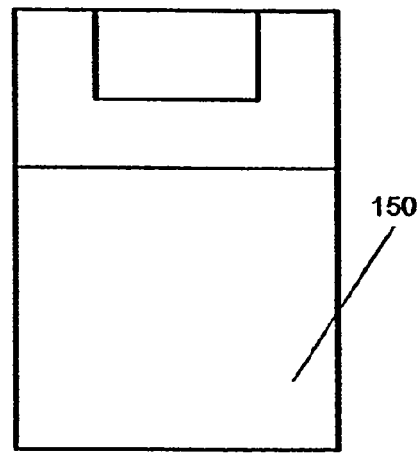
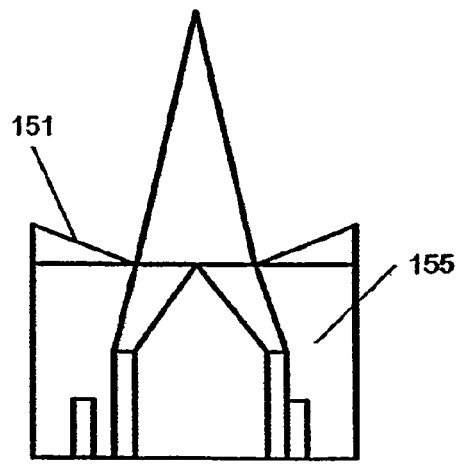

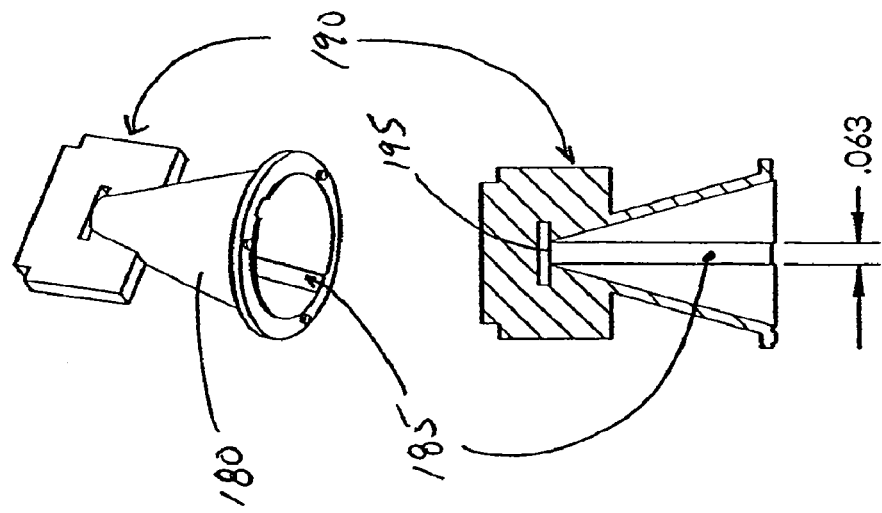
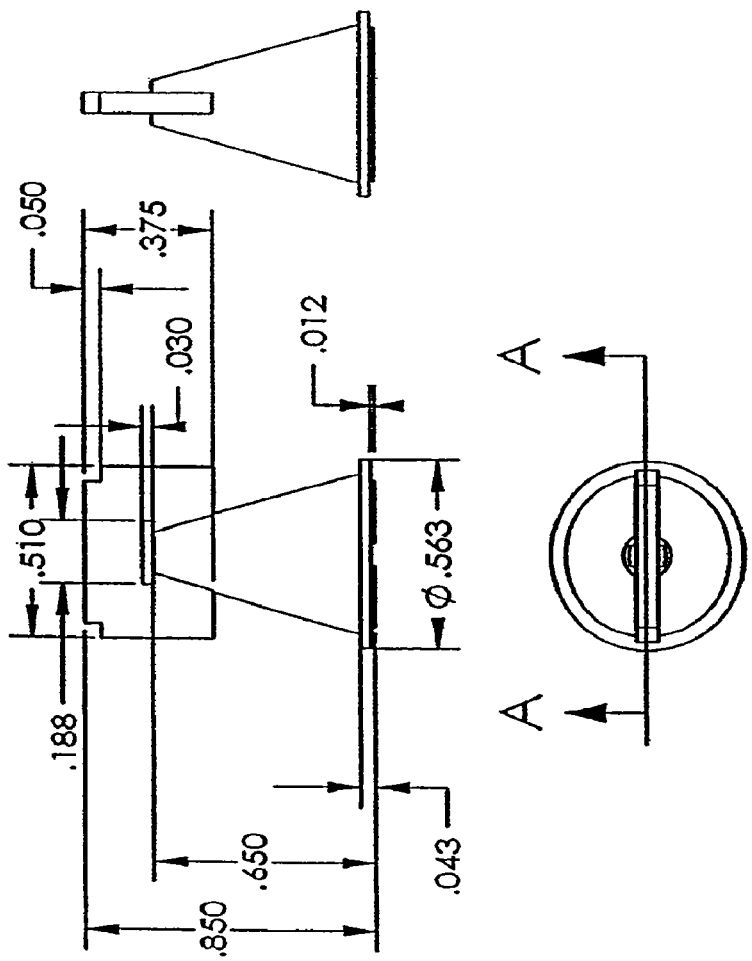
Fig. 33

Velocity Profile of the Air Stream

$X = (v_0 \cos \theta_0) t$ where:

$v_0$ is the initial velocity of the droplet as it passes through the nasal aperature $\theta_0$ is the angle of the nasal pump $t$ is the time the droplet is in the air stream $t = (2 v_0 \sin \theta_0)/g$ Distance traveled: $X$

Fig. 46

Linear Nebulization

Nebulizer Platform

Fig. 50

Type I
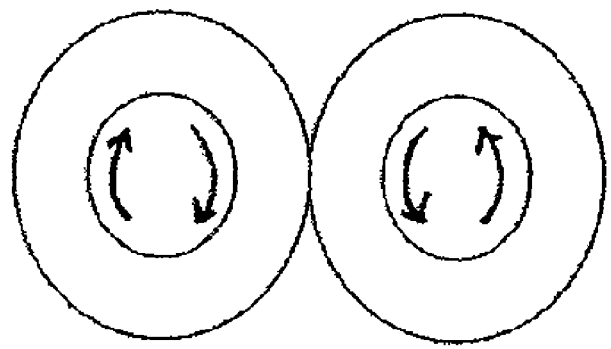
Type II
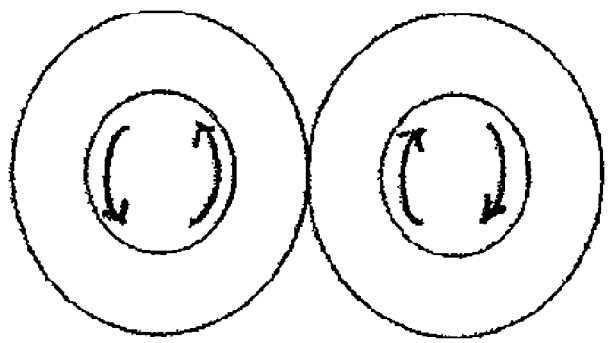
Fig. 54

INTEGRATED NEBULIZER AND PARTICLE DISPERSION CHAMBER FOR NASAL DELIVERY OF MEDICAMENT TO DEEP NASAL CAVITY AND PARANASAL SINUSES

FIELD OF THE INVENTION

The present invention is directed to an apparatus that serves as a conduit for delivering airborne materials to the nasal cavity. In particular, the invention is directed to an integrated device that is useful for the administration of therapeutic agents to the nasal cavity and paranasal sinuses of a patient. The present invention integrates a nebulizer, particle dispersion chamber and nasal adapter into one device.

This application is the United States National Stage under 35 U.S.C. §371 of PCT/US2004/029001 filed Sep. 3, 2004 and published as WO 2005/023335, which claims priority to U.S. Provisional Patent Application Ser. Nos. 60/500,386 filed Sep. 5, 2003, and 60/581,296 filed Jun. 19, 2004, incorporated by reference herein in their entirety.

BACKGROUND

This invention relates to devices for administration of therapeutic agents to the nasal cavity and paranasal sinuses of a patient.

In the United States, sixty million people suffer from chronic sinusitis and allergic rhinitis and are treated by means of topically applied antihistamines, antibiotics, decongestants, and pain relievers. Many of these drugs would work more effectively in relieving symptoms if they could be directly applied to all of the affected areas. However, the devices utilized thus far to deliver these drugs have proven to be extremely inadequate, if not useless, in reaching all areas needed especially the deep nasal cavity and paranasal sinuses where it is critical in the treatment of some of these diseases. In addition to the topically applied drugs above, there are a wide variety of systemically absorbed drugs that are delivered intranasally. Devices utilized for these drugs as well, have proven to be extremely inadequate.

Current delivery systems comprise, for example, a pressurized canister (MDI) that ejects the medicine into the nostrils in short bursts, or streams of atomized liquid in an aqueous nasal spray. The efficacy of medicine administered in this manner is limited due to difficulties in the medicine reaching very little of the nasal mucosa and no part of paranasal sinuses where it needs to be delivered to fully treat the condition. In cases of severe congestion or nasal polyps, the medicine often does not proceed beyond the nostril and will not be effectively absorbed into the bloodstream or the necessary area of the nasal cavity and paranasal sinuses. Current systems also do not allow for particles to reach high into the nasal cavity and paranasal sinuses.

Additionally, nebulizers are machines that convert medicine into a mist, or vapor, of very tiny particles to deliver a drug to the lungs during an attack by breathing the medicine from a pipe attachment or, in the case of young children, a face mask. The small particle size generated is important in that it allows passage of the drug through heavily congested airways over a period of about 10 minutes which allows for deep penetration. Nebulizers are used by asthmatics in case of an asthma attack.

Nasal nebulizers are currently in use for antibiotics and are ineffectively delivering the drugs due to the fact they do not deliver into the paranasal sinuses nor as far into the nasal cavity as this device due to the lack of additional technology enclosed herein.

There is a pronounced need in the art for delivery methods that enable better delivery, and delivery of more medicament to the nasal cavity and paranasal sinuses.

There is a pronounced need in the art for more effective devices to deliver medicaments to all areas of the nasal cavity and paranasal sinuses.

There is a pronounced need in the art for more effective methods and devices to effectively administer therapeutic agents systemically via the nasal passages and the deep paranasal sinuses.

There is a pronounced need in the art for more effective methods and devices for delivery of medicament to treat patients for certain conditions without taking the medicament orally.

SUMMARY OF THE INVENTION

Novel nebulizers, methods of breathing to facilitate them, and methods of drug delivery using the inventive nebulizers are herein disclosed and described. According to preferred aspects of the present invention, particle size and velocity characteristics determine whether a majority of a medicament will reach the deep nasal cavities, the paranasal sinuses, the bloodstream, the circulation (systemic delivery), the lungs, or drip back down the nose or the mouth.

Particular embodiments provide a controlled particle dispersion breathing method performed by a user having a sinus includes providing a nebulizer having a particle dispersion chamber to a user, the particle dispersion chamber capable of producing nebulized particles; activating the nebulizer; breathing a plurality of quick breaths as nebulized particles begin to flow out of the particle dispersion chamber; holding the quick breaths for a plurality of seconds; creating a pressure in the sinus of the user using the back of the throat; repeating the breathing of plurality of long, slow steady breaths and creating a pressure in the sinuses for the duration, or repeating the breathing a plurality of quick breaths, holding the quick breaths and creating a pressure in the sinuses; breathing a plurality of long breaths; and repeating the breathing a plurality of quick breaths, holding the quick breaths, creating a pressure in the sinuses and breathing a plurality of long breaths.

In another embodiment, a nebulizer is shown and described including a nasal adapter; a dispersion chamber in communication with the nasal adapter; an outflow tube in communication with the dispersion chamber capable of causing a plurality of nebulized particles to move in a vortex or other randomized movement within the internal channel of the nebulizer; and a housing, the housing having a medicine chamber in communication with the outflow tube.

In yet another embodiment, a particle dispersion chamber is shown and described including a housing having an external surface and an internal channel; and a plurality of air outputs communicating with the internal chamber, whereby the air outputs are capable of causing a plurality of nebulized particles to move in a vortex or other randomized movement within the internal channel.

In a preferred embodiment, the present invention provides for a nebulizer (e.g., 'jet' or linear/direct nebulization) suitable for topical drug delivery to, or systemic drug delivery via, a deep nasal cavity or paranasal sinus, comprising: a nasal adapter; a dispersion chamber in communication with the nasal adapter; a nebulizing chamber in direct communication with the dispersion chamber, and in which a medicine is nebulizable; and a nebulizing pressure feed in communication with the nebulizing chamber, and having a compressor channel to channel compressed fluid.

In another preferred embodiment, the nebulizer further comprises a nebulizer pressure release member (e.g., nebulization cone in the context of a jet nebulizer, or nebulizatin platform in the context of linear nebulization), comprising a pressure release channel having at a first end a pressure release orifice, wherein the pressure release member and pressure release channel extend into the nebulizing chamber, and wherein the pressure release channel at a second end is in communication with the compressor channel of the nebulizing pressure feed to channel compressed fluid through the pressure release member and orifice and into the nebulizing chamber. Preferably, the pressure release member is integral with the nebulizing pressure feed, although the pressure release member is alternately integral with the nebulizing chamber or with a substantial portion thereof. Alternatively, the pressure release member is integral with both the nebulizing pressure feed, and the nebulizing chamber or a substantial portion thereof.

In preferred embodiments, the wall of the dispersion chamber comprises at least one integral dispersion feed channel suitable to channel compressed fluid into the dispersion chamber to create a vortex, or otherwise affect movement of nebulized particles. Preferably, the integral dispersion feed channel of the dispersion chamber is fed from a compressor channel of the nebulizing pressure feed. Even more preferably, the compressed fluid from a compressor channel of the nebulizing pressure feed is partially diverted to the integral dispersion feed channel of the dispersion chamber through a channel within or along the wall of the nebulizing chamber.

In alternative embodiments, the integral dispersion feed channel of the dispersion chamber and the compressor channel of the nebulizing pressure feed are fed by separate outputs of a multiple output compressor.

Preferably, the fluid is air or another suitable compressible gas, or combinations thereof.

According to preferred aspects of the present invention, the delivered nebulized particles are comprised of particles substantially having a mean diameter of about 2 to about 50 μm, about 5 to about 50 μm, about 5 to about 40 μm, about 5 to about 35 μm, about 5 to about 30 μm, about 5 to about 20 μm, about 5 to about 17 μm, about 5 to about 15 μm, about 8 to about 30 μm, about 8 to about 25 μm, about 8 to about 20 μm, about 10 to about 30 μm, about 10 to about 25 μm, about 10 to about 20 μm, about 10 to about 17 μm, about 10 to about 15 μm, about 11 to about 40 μm, about 11 to about 30 μm, about 11 to about 20 μm, about 11 to about 15 μm, about 12 to about 17 μm, about 15 to about 25 μm, about 15 to about 20 μm, and about 17 to about 23 μm.

Preferably, the delivered nebulized particles are comprised of particles substantially having a mean diameter of about 5 to about 30 μm, about 8 to about 25 μm, about 10 to about 20 μm, about 10 to about 17 μm, about 10 to about 15 μm, and about 12 to about 17 μm.

Preferably, the delivered nebulized particles are comprised of particles substantially having a mean diameter of about 8 to about 25 μm, about 10 to about 15 μm, or about 12 to about 15 μm.

In preferred embodiments, the nebulizer further comprises a medicament cartridge or ampoule, having a three-dimensional exterior surface shape and an interior cavity suitable for housing a medicament, wherein the cartridge or ampoule is insertible into a complementary receptacle of the nebulizing chamber and is thereby cooperative with the nebulizer to enable dispensing of medicament into the nebulizing chamber.

Preferably, cooperative insertion of the cartridge or ampoule is dependent or optionally dependent upon said complementarity between the exterior shape and the receptacle so that deliver of medicaments to individual users can be restricted or controlled by provision of the user with complementary nebulizers and cartridges or ampoules. Therefore, additional preferred embodiments provide a complementary cartridge docking system (CCDS) that allows for drug-specific delivery with respect to a given user and device.

The foregoing aspects and many of the attendant advantages will become more readily appreciated as the same become better understood by reference to the following detailed description, when taken in conjunction with the accompanying drawings. The discussion below is descriptive, illustrative and exemplary and is not to be taken as limiting the invention.

BRIEF DESCRIPTION OF THE DRAWINGS

FIG. 21 shows the results of a sinus ventilation study using a prior art drug delivery apparatus;
and
FIG. 22 shows the results of the sinus ventilation study using an embodiment of the nebulizer with a particle dispersion chamber for delivery of medicament to the sinus cavity.
FIG. 25 shows an alternative embodiment of the nebulizer.
FIG. 26 shows an embodiment of a nebulizing compressor feed with nebulizer pressure cone.
FIG. 27 shows an embodiment of a nebulizing chamber.

FIG. 28 shows an embodiment of a particle dispersion chamber.

FIG. 33 shows cross sectional and perspective views of a nebulizer impacter member used in of FIGS. 30-32.

FIG. 46 shows a modular representation of a preferred embodiment of the inventive integrated nebulizer and particle dispersion chamber.

FIGS. 49 and 50 show an additional, particularly preferred linear nebulization embodiment of the inventive integrated nebulizer and particle dispersion chamber.

FIG. 54 illustrates the preferred modes of the inventive bi-directional controlled particle dispersion delivery as described herein (e.g., dual vortical flow patterns; one in each dispersion channel of a dispersion chamber having dual dispersion channels). Preferred modes Type I and Type II are shown.

DETAILED DESCRIPTION OF THE INVENTION

Figure 1:
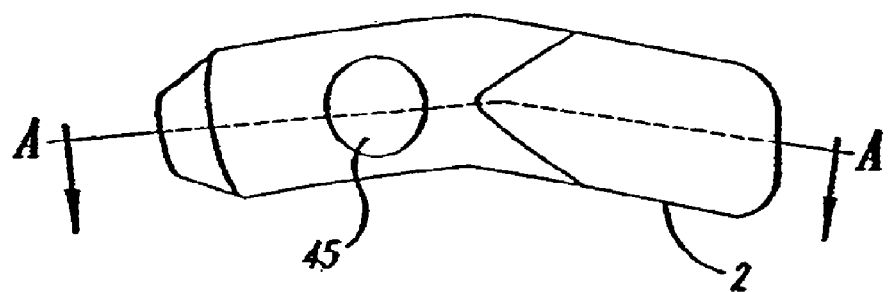
FIG. 1 is a top planar view of one embodiment of the nasal nebulizer.

Current topical drug delivery methods are ineffective at penetrating very far into the nasal cavity and not at all into the paranasal sinuses. Further, systemic delivery via inhalation utilizing the nasal mucosa and mucosa in the paranasal sinuses is desired for many targeted disease states. Preferred aspects of the present invention provide an integrated nebulizer and particle dispersion chamber apparatus that has the ability to deliver the same drugs presently prescribed for many diseases and conditions as very tiny particle doses of medicine via a nasal adapter that allows more efficacious sinus penetration and systemic delivery for the user.

Examples of diseases that can be treated by systemic delivery with the inventive apparatus and methods include, but are not limited to, endocrine and metabolic disorders, migraines, sleep disorders, autoimmune diseases, osteoporosis, neurological diseases and disorders, obesity, sexual dysfunctions, and cardiovascular diseases and episodes.

According to the present invention, the particle sizes, time of application and particle dispersion technology allow the medicine to reach and permeate the nasal cavity and most of the paranasal sinuses. These factors also allow the medicine to enter the user's system via the nasal cavity. All medicines currently applied by direct action to the nasal cavity and paranasal sinuses could be adapted for use with the inventive integrated nebulizer embodiments, including over-the-counter nasal medicines for allergy and colds and flu. Additionally, many medicines currently taken orally, by skin patch, or parenterally could be adapted for use with the inventive integrated nebulizer embodiments.

Significantly, according to the present invention, the integrated nebulizer is used for both topical and systemic delivery of drugs, therapeutics and other beneficial compounds.

For a user with a secondary condition of nasal polyps, the inventive apparatus and methods a low far more effective application of the medicine, which is otherwise blocked or precluded using contemporary systems. Nasal inhalers and spray bottles used to deliver corticosteroids are designed to also slow the re-growth of polyps following their removal. Currently, however, such devices are largely ineffective at accomplishing this, often not slowing polyp growth at all. According to the present invention, the apparatus and methods described herein are significantly more effective in slowing polyp re-growth following their removal.

Many of the side effects of some medicines are eradicated by the inventive devices and methods. With many sprays, for example, the propellant causes a drying of the nasal passages leading to bleeds. With the use of contemporary devices that lead to bleeds, a secondary spray of saline is added to the treatment to try and control the bleeding. Furthermore, steroids in pill form have many unpleasant side effects such as internal bleeding, a redistribution of fluid to the head, neck and back causing unsightly "humps," and easy bruising, to name a few. An effective use of the inventive integrated nebulizer does not have these side effects associated with steroids in pill form.

The inventive integrated nebulizer will allow medicine to be administered to the nasal cavity and paranasal sinuses via very small particles that will penetrate deeply into the nasal cavity, most regions of the paranasal sinuses, and allow for both topical and systemic delivery. The inventive integrated nebulizer will also provide the patient with a more effective absorption of the drug, increasing effectiveness, and will allow multiple conditions to be treated in a far more effective manner.

Typically, since the medicine is delivered in a treatment and not an attack scenario, the application or delivery time is only 0.5-3 minutes, rather than the 10-15 minutes used during an asthma attack. Multiple dose levels of the medicine can be placed in the inventive integrated nebulizer, a week supply for example, and the unit will run for a prescribed time, for example but not limited to three minutes, and will then, in particular embodiments, shut itself off. Preferably, the inventive integrated nebulizer is designed with multiple dose capability and a timer with a pause feature. The pause feature allows the user to stop the treatment under way to deal with a short, minor happenstance and then resume the treatment for the remaining time. The timer is variable to accommodate the drug being administered and/or prescribed by the physician.

In preferred aspects, the nasally delivered nebulized particles are comprised of particles substantially having a mean diameter of about 2 to about 50 μm, about 5 to about 50 μm, about 5 to about 40 μm, about 5 to about 35 μm, about 5 to about 30 μm, about 5 to about 20 μm, about 5 to about 17 μm, about 5 to about 15 μm, about 8 to about 30 μm, about 8 to about 20 μm, about 10 to about 30 μm, about 10 to about 25 μm, about 10 to about 20 μm, about 10 to about 17 μm, about 10 to about 15 μm, about 11 to about 40 μm, about 11 to about 30 μm, about 11 to about 20 μm, about 11 to about 15 μm, about 12 to about 17 μm, about 15 to about 25 μm, about 15 to about 20 μm, and about 17 to about 23 μm.

Preferably, the nasally delivered nebulized particles are comprised of particles substantially having a mean diameter of about 5 to about 30 the delivered nebulized particles are comprises of particles substantially having a mean diameter of about 5 to about 30 μm, about 10 to about 20 μm, about 10 to about 17 μm, about 10 to about 15 μm, and about 12 to about 17 μm.

Preferably, the nasally delivered nebulized particles are comprised of particles substantially having a mean diameter of about 10 to about 15 μm, or about 12 to about 15 μm.

The phrase "substantially having a mean diameter," as used herein with respect to preferred particle diameter ranges, refers to the use of particle collections, wherein at least 50%, at least 60%, at least 70%, at least 80%, at least 90%, at least 95%, or at least 98% have the preferred diameter range. Preferably, at least 60%, at least 70%, at least 80%, at least 90% or at least 95% of the nebulized particles are of the preferred particle diameter range. Preferably, at least 70%, at least 80%, at least 90% or at least 95% of the nebulized particles are of the preferred particle diameter range.

Advantages of Vorticity and Preferred Particle Sizes

According to preferred aspects of the present invention, placing nebulized particles in a vortex (into vortical flow) for nasal delivery allows for efficient delivery of nebulized particles to the deep nasal cavity and paranasal sinuses. The following compares motion in a plane, and vortical circulation.

Motion in a Plane. Curved motion with constant acceleration is projectile motion. There is negligible impact of the air stream on the path of the droplet. In the case of the typical prior art nasal pump, the initial velocity of the droplet $(v_o)$ is generated by the pump, and where $$v_o >> v_{air\,stream}$$

(this is further exaggerated in the nasal cavity), the air stream velocity is equal to the volumetric flow divided by the cross-sectional area.

$$A_{aperture} << A_{nasal\,cavity}$$

Thus, for conventional nasal pumps and nebulizers, motion of a droplet is one of constant acceleration, g, directed downward. There is no horizontal component of acceleration, and the horizontal velocity component retains its initial value throughout the flight.

Figure 38:
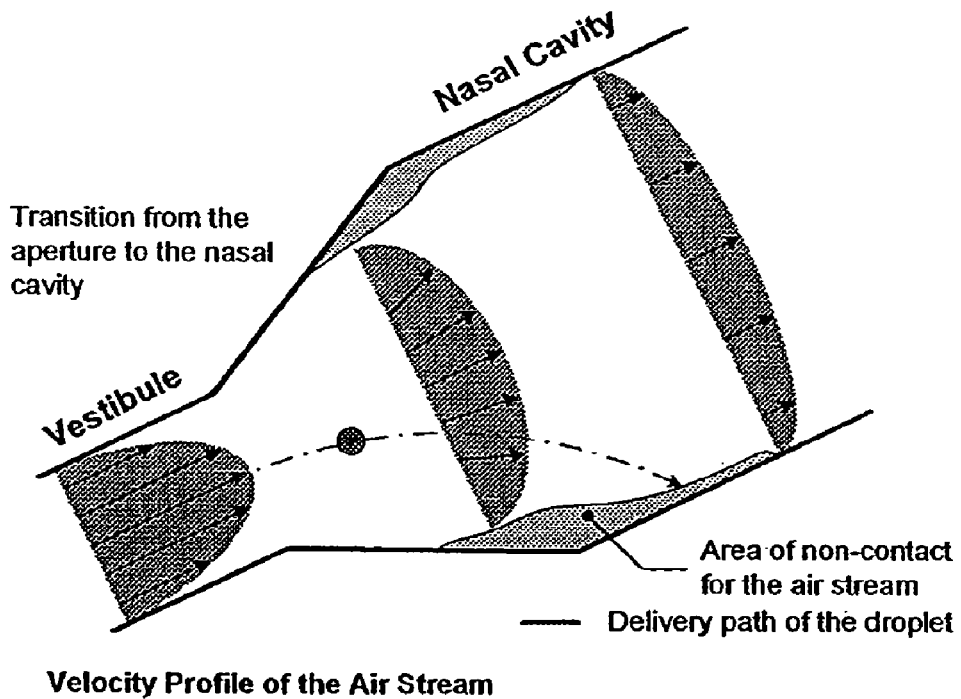
FIG. 38 shows the delivery pattern of a particle droplet exiting from a prior art device.
Figure 39:
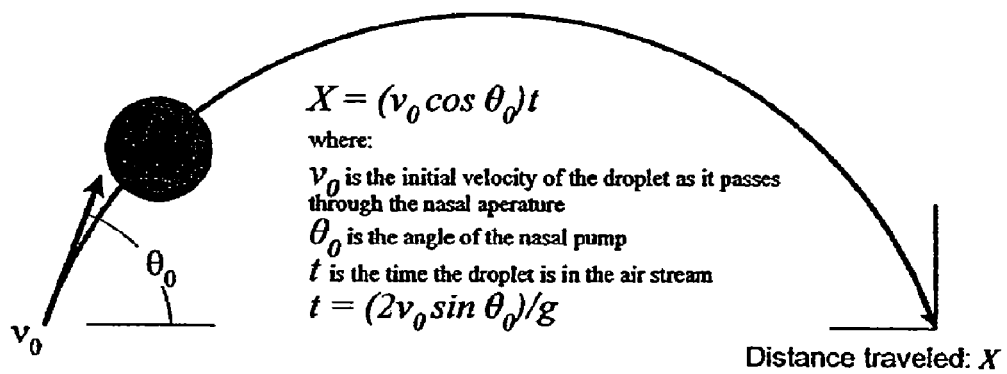
FIG. 39 shows the droplet trajectory of a particle exiting from a prior art device.

FIG. 38 shows the result for a typical prior art device; that is, a delivery pattern that causes the droplets to distribute on the soft pallet. FIG. 39 shows the droplet trajectory of prior art nasal pump or nebulizer.

Vorticity and Circulation. According to preferred embodiments of the present inventions, vorticity plays a central role in the development of forces on an object such as the lifting force. It is important to understand an important vorticity-related quantity known as circulation, "Γ." Circulation is defined by:

$$\Gamma = \int_C u\,ds = \iint_A \omega n\,dA$$

Where: "C" is a closed contour, and "ds" is a differential vector tangent to the contour; "n" is a unit normal to the plane containing the contour C; and circulation is the integral of the vorticity component normal to the area bounded by the contour.

Figure 40:
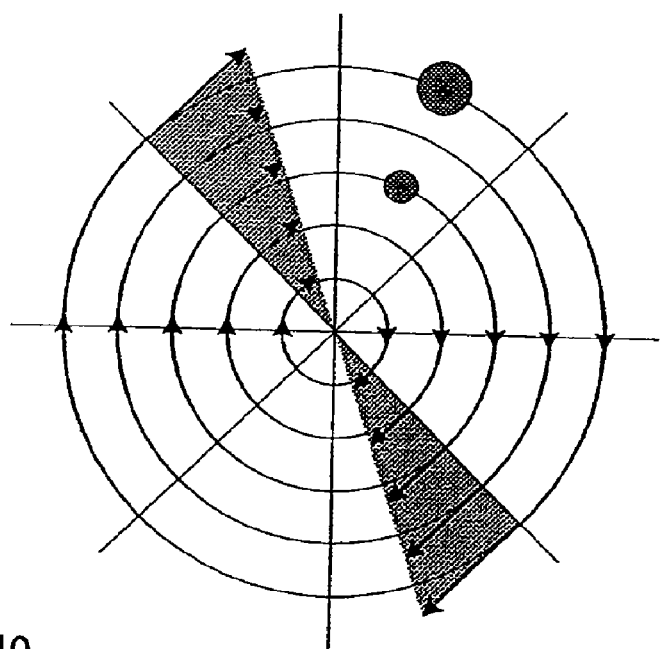
FIG. 40 illustrates the concept of vorticity by showing the increase in velocity as a function of the distance from the center of a vortex.

Circulation provides a measure of strength of the vorticity contained with in the contour. Circulation is constant across the vortex rings. Therefore velocity increases as a function of the distance from the center of the vortex, as illustrated in FIG. 40. This means the velocity of an air stream above a droplet is greater than the velocity below the droplet, creating a low pressure:

$$p_{\psi n+1} < p_{\psi n}$$

Following the principles behind Bernoulli's equation, this generates lift. To emphasis the connection between vorticity and the force on a droplet (lift per unit diameter on the droplet) Lift is defined by:

$$L = \rho v_{air} \Gamma_n$$

Figure 41:
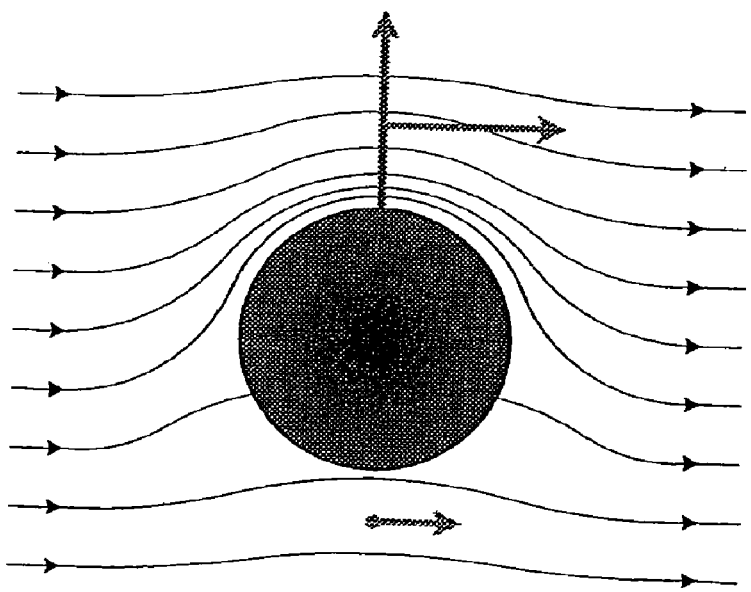
FIG. 41 illustrates the connection between vorticity and the force on a droplet that creates lift.

The dynamic lift on the droplet is normal to the air stream flow, as illustrated in FIG. 41. With respect to, for example, a nose, this direction is up into the nasal cavity and toward the lining of the sinuses.

A vortex will also act like a clarifier and will send the larger droplets to the outside rings and will keep the smaller diameter droplets in the air stream for a longer period of time.

Figure 42:
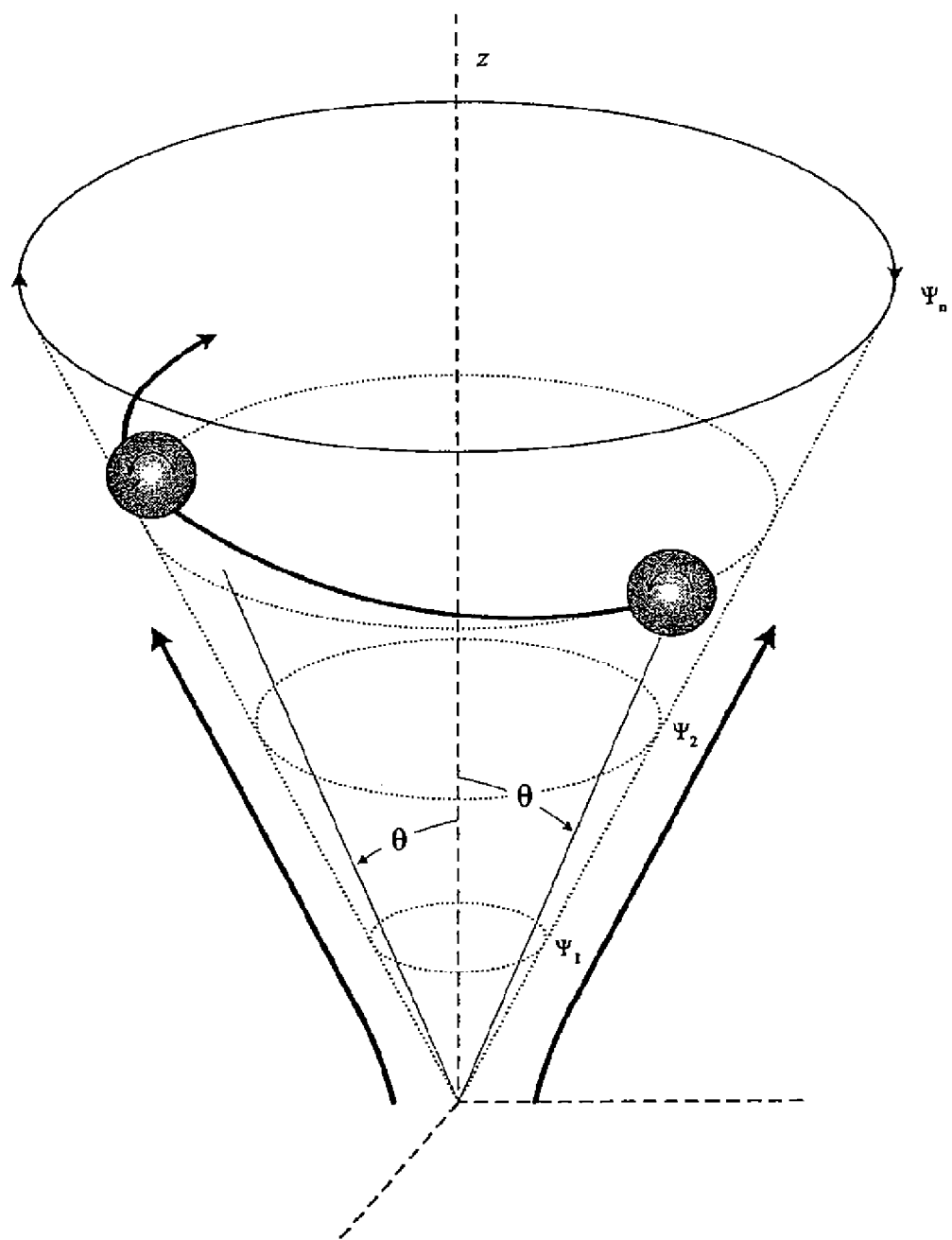
FIG. 42 illustrates a three-dimensional model of a vortex, displaying key forces, including the affects of the inventive controlled introduction of a supplemental inhaled air curtain adjacent to and surrounding the vertical flow patterns, and which causes vortex stretching and a corresponding increase in vorticity as discussed herein.

FIG. 42A illustrates a three-dimensional model of a vortex, displaying key forces. One key factor in the present preferred implementations is the controlled introduction of a convective draft (e.g., air brought into the nose that is not generated by the atomizer; supplemental inhalation). This air is introduced as a shear force, vertical to the direction of the vortex. The convective draft affects the value of the angle θ and the cross-sectional area A, at any given point along the Z-axis, causing vortex stretching and increasing the vorticity.

To understand vortex stretching, consider a point in the vortex, where the cross-sectional area is defined by A. When the vortex is elongated, the principal of mass conservation states the cross-sectional area must decrease to contain the same fluid particles. The circulation (r) remains constant, and average voracity of the vortex increases inversely to the decrease in the cross-sectional area. The strength of the vortex is then carried deeper into the nasal cavity.

Droplet Distribution. According to the present invention, the mass median aerodynamic diameter (MMAD) is important in determining droplets within the nasal passages. Droplets with a MMAD less than about 8 microns (μm) in diameter have a high probability of reaching the lower areas respiratory track. Larger droplets (e.g., 8-25 μm) will be more controllable (are more substantially acted upon) by the forces generated within a vortex. Droplets with a MMAD greater than 25 μm are not very aerodynamic and have a high probability of leaving the vortex early.

Figure 43:
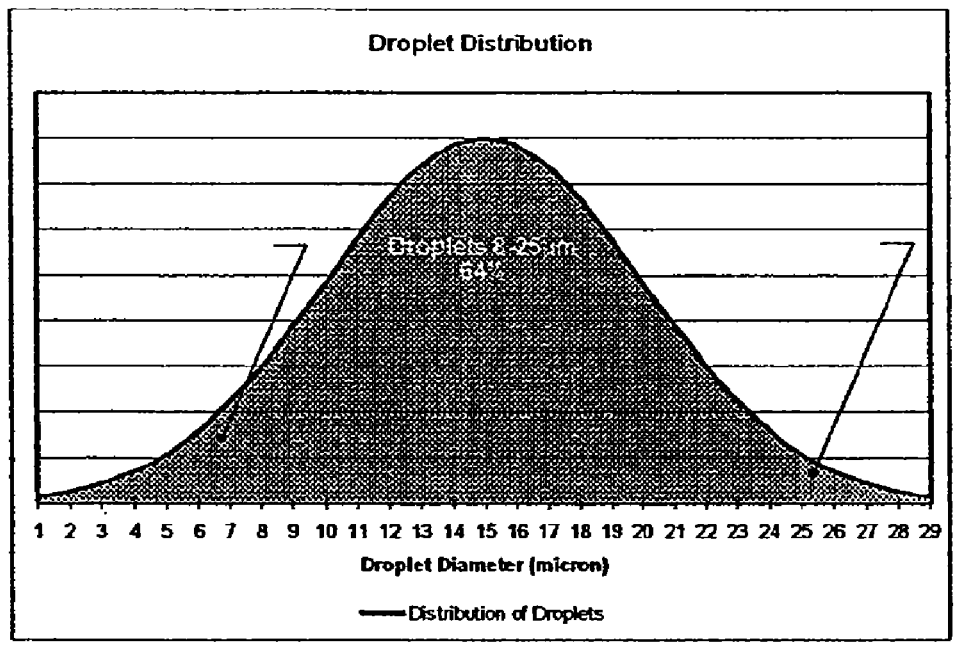
FIGS. 43 and 44 illustrate droplet distributions.
Figure 44:
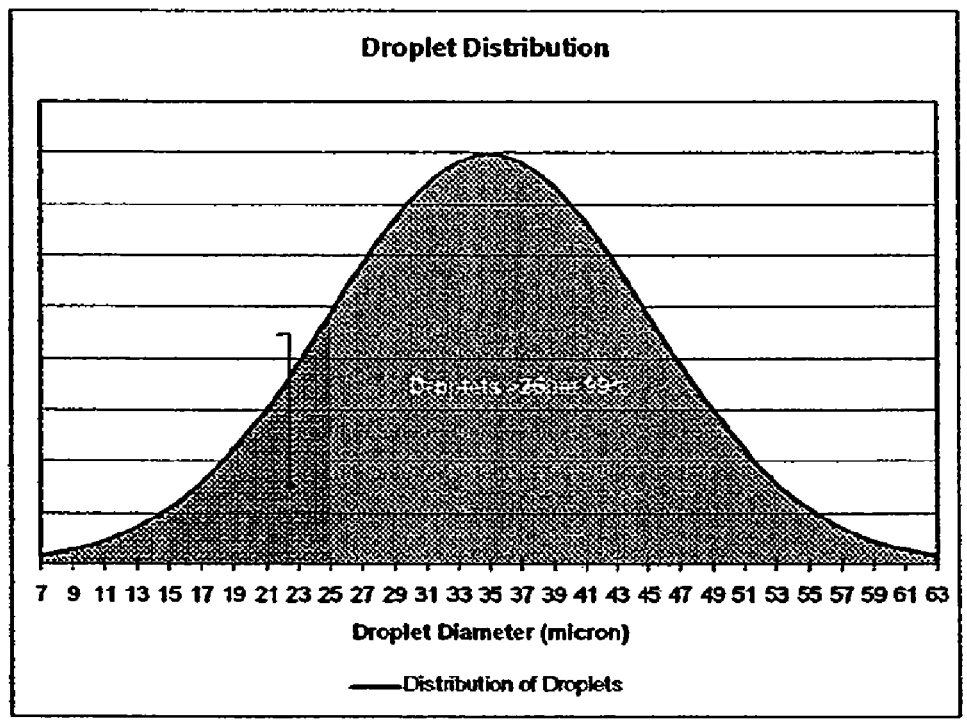

Prior art nasal pumps, for example, have a mean droplet size of 35 μm. Droplet distribution indicates ~99% of the delivered volume of drug will end up on the pallet. FIGS. 43 and 44 show droplet distributions for particles of different sizes.

FIG. 44 shows a typical droplet distribution for a prior art nasal pump, wherein the mean droplet size is about 35 μm. With this droplet distribution, about 99% of the delivered volume of drug will end up on the pallet, and will not reach the deep nasal cavity and sinuses.

FIG. 43, by contrast, shows a droplet distribution according to one embodiment of the present invention. Here the MMAD is about 15 μm, with a standard deviation of about 5 μm. With this distribution, about 64% of the nebulized drug is controlled by the vortex, and is delivered deep into the nasal cavity and sinuses.

According to preferred aspects of the present invention, the nasally delivered nebulized particles are comprised of particles substantially having a mean diameter of about 2 to about 50 μm, about 5 to about 50 μm, about 5 to about 40 μm, about 5 to about 35 μm, about 5 to about 30 μm, about 5 to about 20 μm, about 5 to about 17 μm, about 5 to about 15 μm, about 8 to about 30 μm, about 8 to about 20 μm, about 10 to about 30 μm, about 10 to about 25 μm, about 10 to about 20 μm, about 10 to about 17 μm, about 10 to about 15 μm, about 11 to about 40 μm, about 11 to about 30 μm, about 11 to about 20 μm, about 11 to about 15 μm, about 12 to about 17 μm, about 15 to about 25 μm, about 15 to about 20 μm, and about 17 to about 23 μm.

Preferably, the nasally delivered nebulized particles are comprised of particles substantially having a mean diameter of about 5 to about 30 the delivered nebulized particles are comprises of particles substantially having a mean diameter of about 5 to about 30 μm, about 10 to about 20 μm, about 10 to about 17 μm, about 10 to about 15 μm, and about 12 to about 17 μm.

Preferably, the nasally delivered nebulized particles are comprised of particles substantially having a mean diameter of about 10 to about 15 μm, or about 12 to about 15 μm.

The phrase "substantially having a mean diameter," as used herein with respect to preferred particle diameter ranges, refers to the use of particle collections, wherein at least 50%, at least 60%, at least 70%, at least 80%, at least 90%, or at least 95% have the preferred diameter range. Preferably, at least 60%, 70%, 80%, 90% or 95% of the nebulized particles are of the preferred particle diameter range. More preferably, at least 70%, 80%, 90% or 95% of the nebulized particles are of the preferred particle diameter range.

Exemplary Embodiments

Referring now to the accompanying drawings, as shown in FIGS. 1-15, a nasal adapter 10 has been designed to attach to the outflow tube 15 of the nebulizer 25 to allow it to fit over the nasal openings and the nose itself restricting the flow of medicine to the nose alone. The nasal adapter 10 limits various unwanted occurrences such as delivery of any medicament to the eyes and face surrounding the nose and into the general environment.

Use of a nasal adaptor 10 also limits the spread and growth of bacteria or microorganisms. Use of a nasal adaptor 10 that fits over the nasal openings reduces the spread of bacteria that can be picked up from inside the nasal openings into or onto the delivery device if the nasal adaptor 10 were placed inside the nasal openings as is the case with current MDI's or AQ sprays. Further, use of a disposable nasal adaptor 10 that fits over the nasal openings reduces the occurrence of re-inoculation of the nasal openings with bacteria present on a nasal adaptor 10, when not properly cleaned, is fit over the nasal openings. Also, use of a disposable nasal adaptor 10 that fits over the nose reduces the extent of bacteria or microorganisms picked up from inside the nasal openings which can grow in the any tubing 80 associated with the nebulizer 25.

Figure 7:
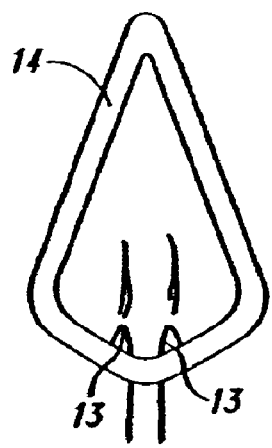
FIG. 7 is a rear view of the nasal adapter.
Figure 8:
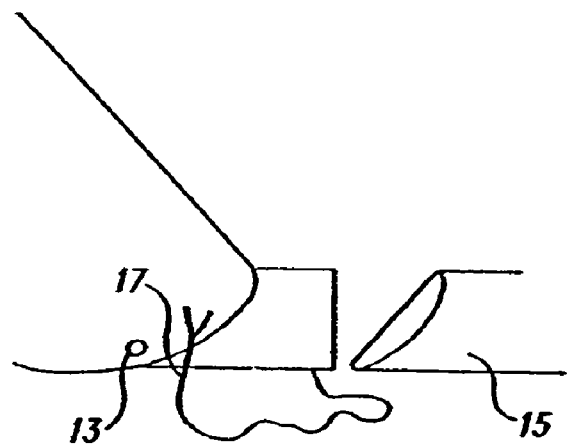
FIG. 8 is a side view of the tubing and nasal adapter.

As shown in FIG. 7, the nasal adapter 10 has an optional lip 14 to seal the area around the nose keeping the aerosolized medicine away from the eyes and restricting the flow to the nasal passages. In one aspect of this embodiment, the nasal adapter 10 is approximately 1½ inches wide across the bridge of the nose and 1½ inches long. Other dimensions for the bridge width and length are envisioned. Further, in one aspect of the lip 14, the lip 14 on the nasal adapter 10 is approximately ⅛ inch long and is capable of forming a seal between the nasal adapter 10 and the face surrounding the nose. Other lip 14 widths are envisioned. In one aspect of this embodiment, the outflow tube 15 has an internal diameter of 9/16 of an inch and is tapered to fit or cooperate with the hose 9. Other diameters of the outflow tube 15 are envisioned and the device is not to be restricted to the above-mentioned diameter. As shown in FIG. 8, in one aspect, the nasal adapter 10 has been designed with exhaust valves or vent holes 13 on either side below the curve of the nose allowing necessary venting while keeping the aerosolized medicine away from the eyes.

Figure 2:
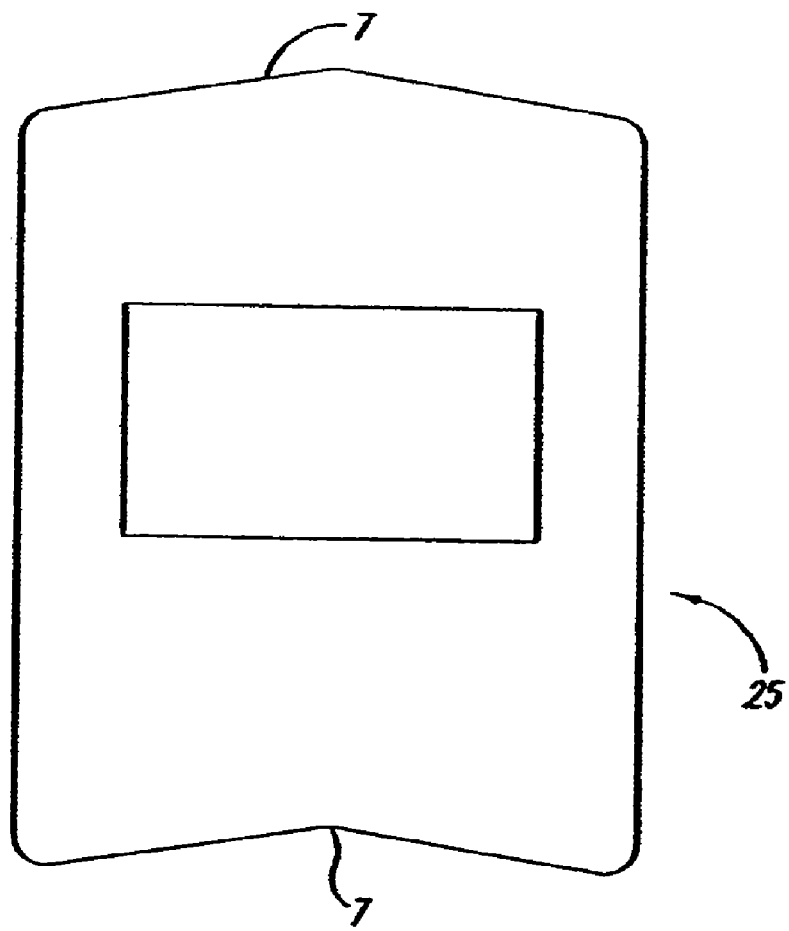
FIG. 2 is a frontal elevational view of the nasal nebulizer.
Figure 5:
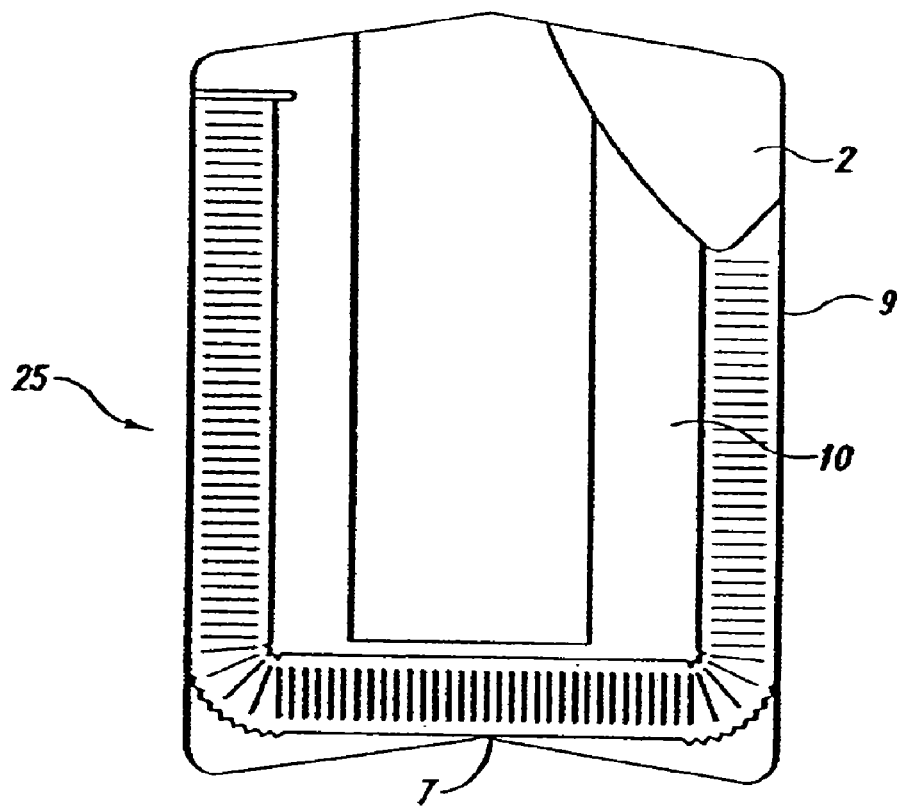
FIG. 5 is a side cross-sectional view of the nasal nebulizer of FIG. 1 along line A-A showing internal components thereof.
Figure 6:
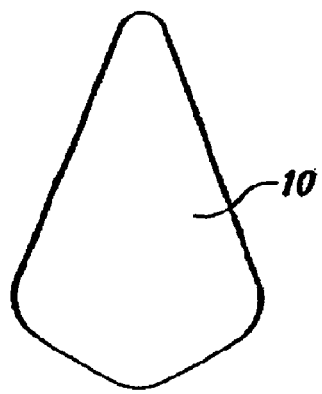
FIG. 6 is a front view of one embodiment of the nasal adapter.

The nebulizer 25 has been greatly improved by being designed to accommodate daily use rather than occasional use as originally intended. As shown in FIG. 2, in one embodiment, it has been designed thinner and shorter with a hip-hugging curve 7 when in use in hands-free position. As shown in FIG. 8, for hands-free operation, the nasal adapter is equipped with elastic bands 17 that go around the head to hold the adapter in place while the treatment is delivered. Other manners of holding the nasal adapter 10 in place other than elastic bands 17 are envisioned. As shown in FIG. 5, the nasal adapter 10 can be attached to a hose 9 built into the device that can extend the reach to a standing person or a sitting person. In one aspect, the hose 9 is an accordion hose. In another embodiment, it can also be operated with the nasal adapter 10 attached directly to the unit outflow and held by hand to the nose for the duration of the treatment.

Figure 3:
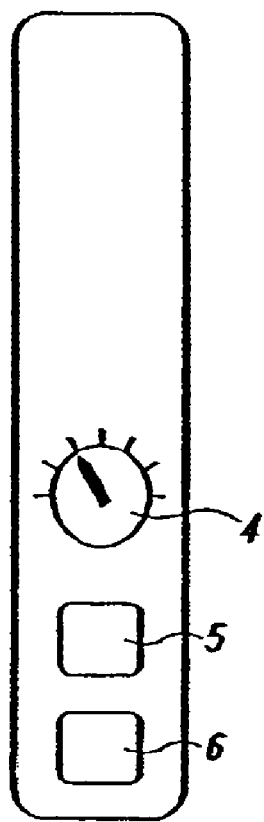
FIG. 3 is a side elevational view of the nasal nebulizer.
Figure 4:
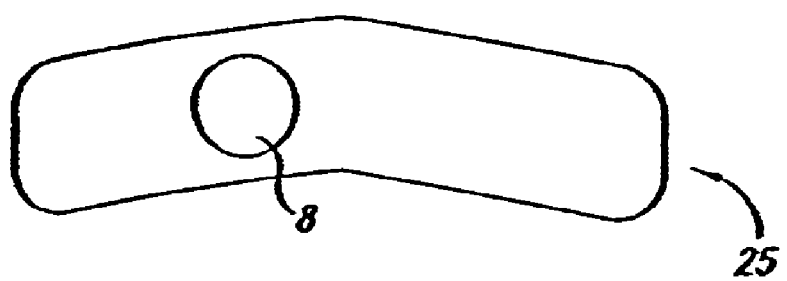
FIG. 4 is a bottom planar view of the nasal nebulizer.
Figure 10:
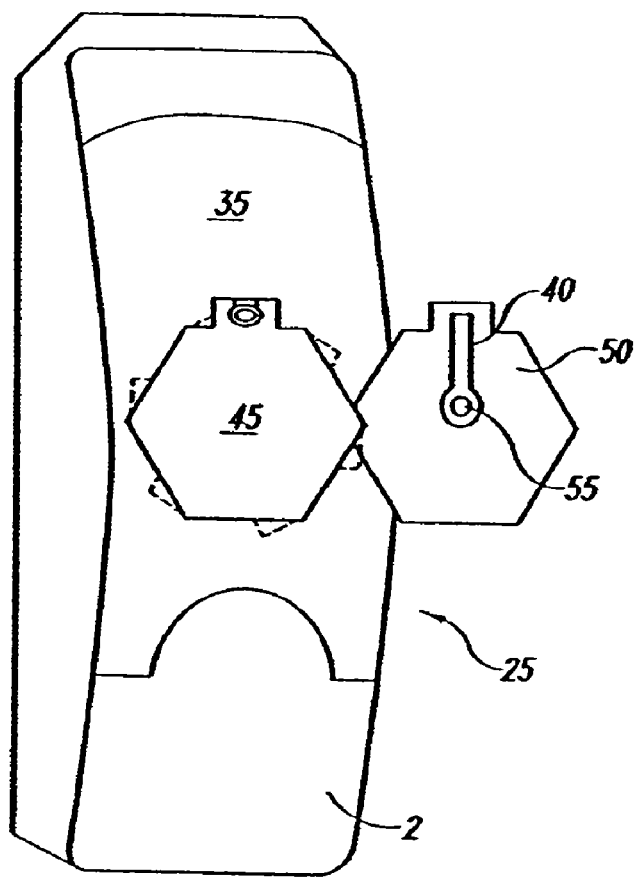
FIG. 10 is a top view of the nebulizer showing the cartridge chamber.

As shown in FIG. 4, an additional feature will be the multiple dose compartment 8 arrangement in which multiple doses of a medicament or compound may be placed inside the nebulizer 25. For example, in the case of chronic sinusitis, a week's worth of medicine will be placed into the nebulizer 25. As shown in FIG. 3, the nebulizer 25 has been designed with a timer 4 so that it will run for a programmed period of time and then turn itself off. As shown in FIG. 3, a pause feature 5 has been added to allow for dealing with minor disturbances and then resuming the treatment. The time allotted will depend upon the optimum time needed for the drug being dispensed and it has been designed to prevent evaporation for the duration of the predetermined supply. As shown in FIG. 10, the device can also be used in a single-dose application.

Figure 9:
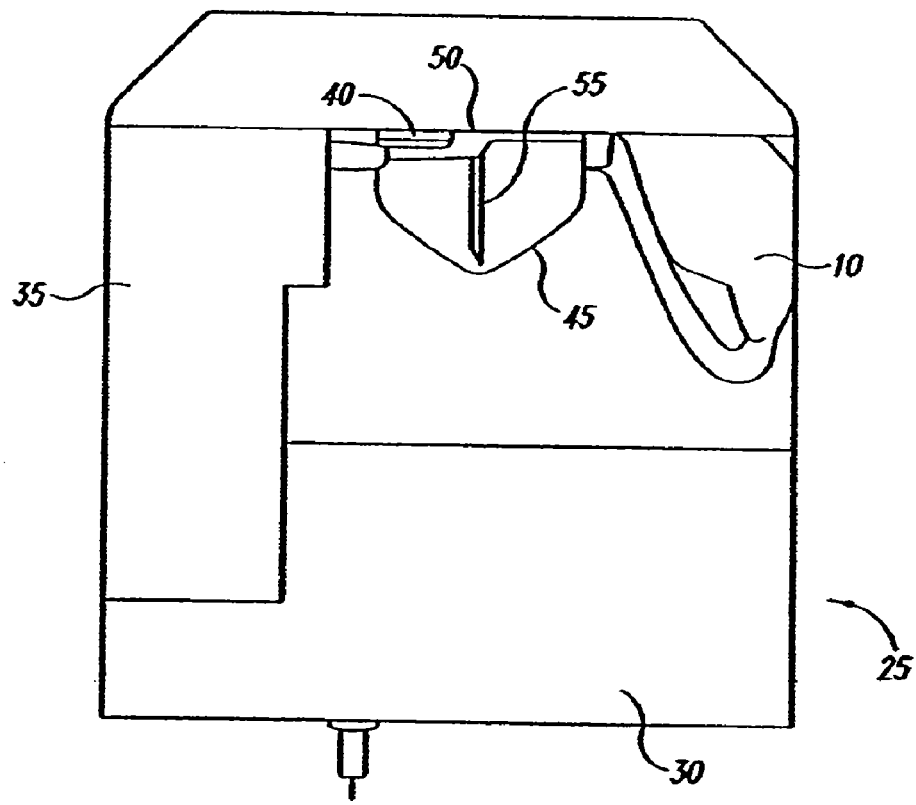
FIG. 9 is a side view of another embodiment of the nebulizer showing the cartridge chamber.

FIGS. 9 and 10 show one embodiment of the nebulizer 25. The nebulizer 25 may have a variety of dimensions but in one aspect, the nebulizer 25 is approximately three inches wide and approximately four inches high. The nebulizer 25 will generally include a power supply 30, a pump 35, a pump connector 40, a medicine chamber 45, a lid 50 for covering the medicine chamber and a nebulizing stem 55 for introduction into a FFS ampoule 60 inserted into the medicine chamber 45. A nasal adapter 10 of varying sizes is associable with the nebulizer 25.

Figure 23:
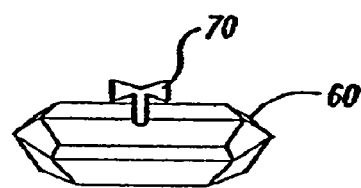
FIG. 23 shows a side view of one embodiment of the cartridge.
Figure 24:
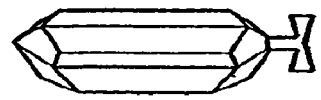
FIG. 24 shows a prior art cartridge.

FIG. 23 shows one embodiment of the Form-Fill-Seal (FFS) ampoule 60. The FFS ampoule 60 is shaped so that it fits into the medicine chamber 45 and can spin freely therein. It is provided with an opening 65 so that the nebulizing stem 55 can be introduced into the FFS ampoule 60 and access the medicament contained in the FFS ampoule 60 through the opening 65. FIG. 23 shows the FFS ampoule 60 for use with the nebulizer 25. As shown in FIG. 23, the FFS ampoule 60 is generally a three-dimensional octagonal shape filled with a medicament. In one embodiment, the FFS ampoule 60 is formed from plastic, preferably biodegradable. As shown in FIG. 24, the prior art FFS ampoules for containing medicament are generally of three-dimensional shape and have a twist opening located at the proximal or distal end of the FFS ampoule. Rather, the improved FFS ampoules 60 may have a twist opening located on the surface of one of the octagons forming the top and bottom of the FFS ampoule. In another embodiment, the FFS ampoule 60 may have a weakened perforated area on the surface of the FFS ampoule 60 through which the nebulizing stem 55 can be easily introduced. As shown in FIG. 23, the novel shape of the FFS ampoule 60 allows for it to fit within the medicine chamber 45 of the nebulizer 25. The FFS ampoule 60 then sits in the medicine chamber 45 and is capable of spinning while seated in the medicine chamber 45. The nebulizing stem 55 can be introduced into the FFS ampoule 60 at the FFS ampoule opening 65 caused by the removal of the twist-off cap 70. Using the FFS ampoule 60 in the nebulizer 25 facilitates the delivery of proper dosage by providing a FFS ampoule 60 pre-packaged with a proper dosage amount; the dosage being variable by medicament, ailment, patient and the like. In addition, the FFS ampoule 60 facilitates the use of the nebulizer 25 with a variety of various medicaments. Since the FFS ampoule 60 is placed into the medicine chamber 45, the medicine chamber 45 itself does not fill with a variety of different medications. This eases the cleaning process of the medicine chamber 45. It also prevents the intermixing of different medicaments in the medicine chamber 45. For example, by using the FFS ampoule 60, the same nebulizer 25 can be used to deliver two different medications at different times to different patients with more certainty that the different medications would not intermix in the medicine chamber 45. Without the use of the FFS ampoule 60, when the medicine chamber 45 is filled first with one medicament and later with another medicament for delivery via use of the nebulizer 25, if the medicine chamber 45 is not properly and thoroughly cleaned, the two different medicaments inserted into the medicine chamber 45 may intermix. The use of the FFS ampoule 60 greatly reduces the chances of intermixing of two medicaments and facilitates or increases the ease of cleaning of the medicine chamber 45. In another embodiment of the nebulizer 25, drugs, medicaments, therapeutic or beneficial compounds can be added directly into a medicine chamber 45 of a nebulizing chamber 150.

In other embodiments, rather than using the FFS ampoule 60, the nebulizer 25 is capable of accepting a multi-dose FFS ampoule 75. In use, the multi-dose FFS ampoule 75 may be filled with, for example, a week's supply of a particular medicament. The nebulizer 25 would then be provided with a dosing system so that each time medicament is dispensed from the multi-dose FFS ampoule 75, it is dispensed in a dose-specific amount. In other aspects of this embodiment, the multi-dose FFS ampoule 75 may be filled with enough medicament for a daily dose, bi-weekly dose, a weekly dose, a bi-monthly dose, and other variety of dosage amounts.

In another aspect of the embodiment of the FFS ampoule 60, it is envisioned that the FFS ampoule 60 may be an octagonal shape, a circular shape, an oval shape, and any other variety of shape which would be cooperative with the medicine chamber 45.

As shown in FIGS. 11-15, the nebulizer 25 includes a tube 80 for delivering compressed air in cooperation with nebulized particles from the medicine chamber 45. The tube 80 may also deliver any other gas or combination of gases. The nebulizer 25 also includes a particle dispersion chamber 85. The particle dispersion chamber 85 is associated with a nasal adapter 10. As the nebulized particles travel from the medicine chamber 45 through the compressed air tubing 80, they reach the particle dispersion chamber 85. As the particles are passed through the particle dispersion chamber 85, they are swirled into a vortex and emerge from the chamber 85 while still in the vortex into the nasal cavity and the paranasal sinuses. In this process, the individual particles are themselves caused to spin and are caught up in the vortex. The particles advantageously enter the nasal cavity at many angles. The particles also bounce or ricochet within the nasal cavity allowing the particles to reach previously impossible areas. Further, the particles are capable of systemic delivery. The particles can be delivered across the nasal and sinus mucosal membranes to enter the systemic blood circulation to treat medical conditions elsewhere in the body. Compounds that can be delivered include, but not limited to, synthetic and natural peptides, proteins, antibodies, hormones, vaccines, DNA and RNA, sugars, carbohydrates, and lipids. Delivered compounds can also include small synthetic organic pharmaceuticals, radiopharmaceuticals, vitamins, homeopathic solutions or any pharmaceutical, with or without additional formulation to aid in the stability or to aid in the crossing of the mucosal membrane by the compound.

Figure 11:
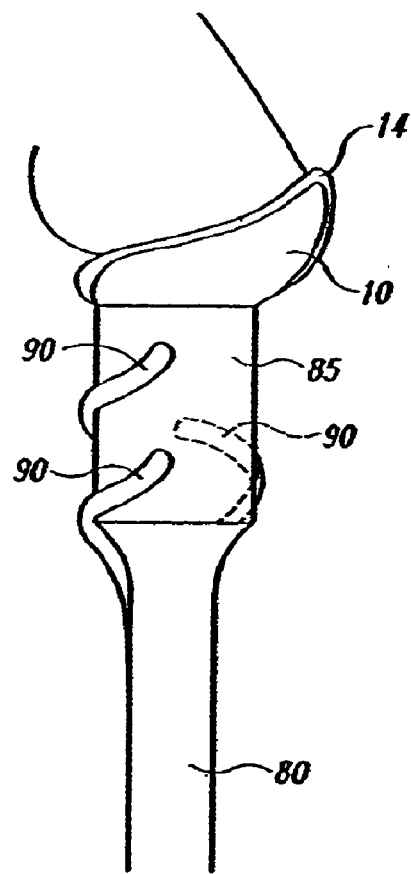
FIG. 11 shows one embodiment of the particle dispersion chamber, the tubing, and the nasal adapter.

In one embodiment of the particle dispersion chamber 85 as shown in FIG. 11, as the particles exit the compressed air tubing 80 and enter the particle dispersion chamber 85, they come into contact with a variety of air outputs 90. The air outputs 90 may be positioned either randomly along the particle dispersion chamber 85 or in a set array. The air outputs 90 are, for example, a plurality of air jets which spurt, blow or vent, or the like, into the particle dispersion chamber 85 and cause the nebulized particles within the chamber 85 to randomly move in a vortex. This random movement of the particles in a vortex continues while the particles travel through the nasal adapter 10, eventually into the nose and into the nasal cavity and paranasal sinuses and capable of local and systemic delivery.

Figure 12:
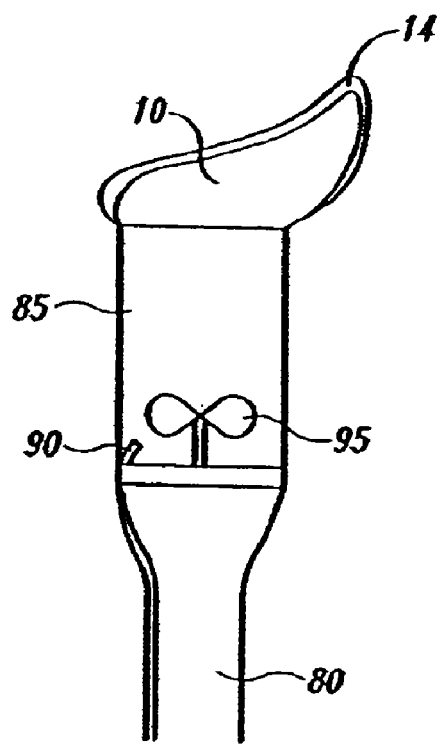
FIG. 12 shows a further embodiment of the nasal adapter, particle dispersion chamber, and tubing.

In a further embodiment, as shown in FIG. 12, the nebulized particles once again travel through the tubing 80 and into the particle dispersion chamber 85. In the embodiment shown in FIG. 12, the particle dispersion chamber 85 contains at least an air output 90 and a dispersion blade 95. The dispersion blade 95 may have solid blades or blades made of netting or openings. Movement of the dispersion blade 95 is created through spurts or jets of air exiting from the air output 90. Alternatively, movement of the dispersion blade 95 can be created using a motor. A variety of other equivalent movement mechanisms varying from magnetic to a wind-up spring can be used to create movement of the dispersion blade 95. As the dispersion blade 95 rotates within the particle dispersion chamber 85, the nebulized particles exiting from the tubing 80 into the dispersion chamber 85 come into contact with the movement from the dispersion blades 95 and are caused to randomly move within the dispersion chamber 85 in a vortex. As the particles exit the particle dispersion chamber 85 and the nasal adapter 10, they enter the nasal cavity and paranasal sinuses and the paranasal sinuses still exhibiting random motion in the vortex.

Figure 13:
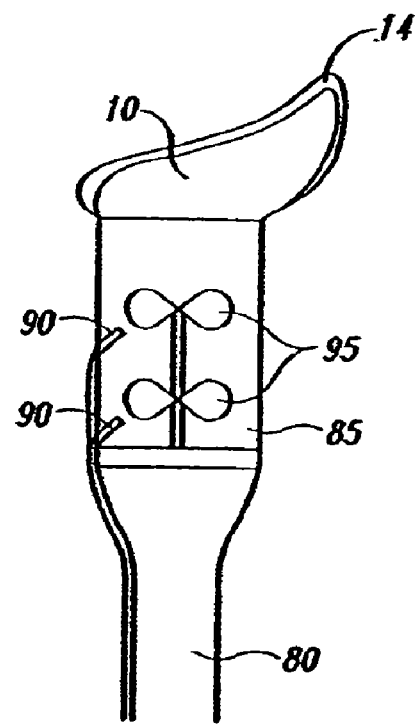
FIG. 13 shows yet another embodiment of the nasal adapter, particle dispersion chamber, and tubing.

As shown in FIG. 13, a plurality of dispersion blades 95 and outlets 90 may be located in the particle dispersion chamber 85. This plurality of blades 95 may rotate all clockwise, all counterclockwise, or in opposite directions from one another around an axis of rotation. The dispersion blades 95 create motion of the nebulized particles in a vortex within the particle dispersion chamber 85. The nebulized particles exit the particle dispersion chamber 85 and nasal adapter 10 still in a vortex and enter into the nasal cavity and paranasal sinuses.

Figure 14A:
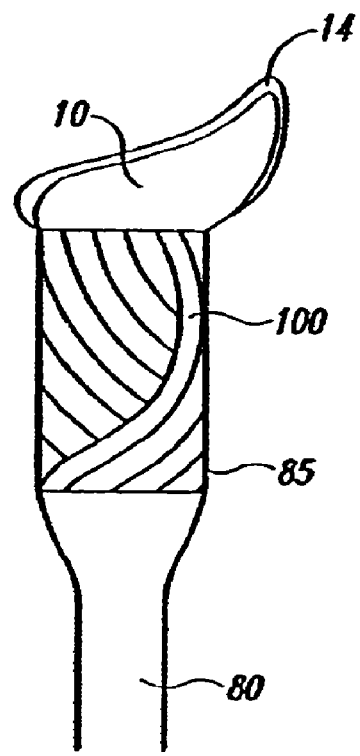
FIG. 14a shows another embodiment of the nasal adapter, particle dispersion chamber, and tubing.
Figure 14B:
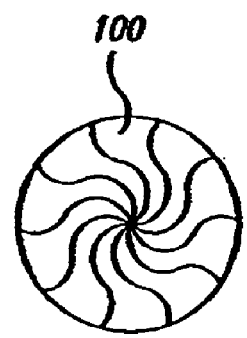
FIG. 14b shows a bottom view of one embodiment of the baffle.

In the embodiment shown in FIG. 14, the nebulized particles exit the tubing 80 and come into contact with a baffle 100 located in the particle dispersion chamber 85. The baffle 100 is shaped so as to create movement of the particles while in a vortex. As shown in FIG. 14, the baffle 100 is generally serpentine shape. Although in FIG. 14 the baffle 100 is shown in a generally serpentine or helix shape, it is understood that any baffle 100 shape which would create motion of the nebulized particles in a vortex as they exit the dispersion chamber 85 is equivalent. For example, a helical shaped baffle 100 may create motion of the particles in a vortex.

Figure 15:
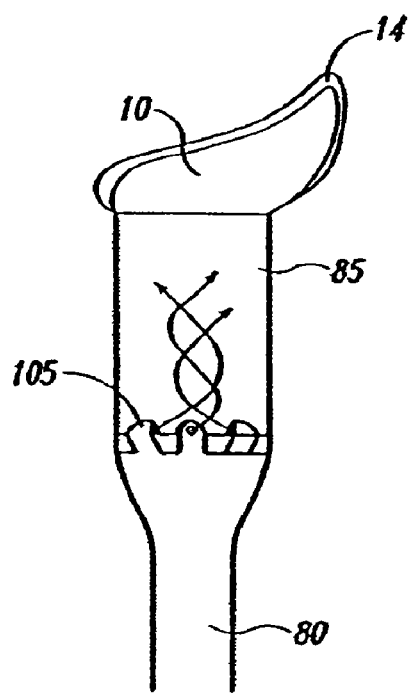
FIG. 15 shows yet another embodiment of a nasal adapter, particle dispersion chamber, and tubing.

The embodiment shown in FIG. 15 includes a particle dispersion chamber 85 having a plurality of directional output nozzles 105. The directional output nozzles 105 spray, spurt, vent, jet, or the like, air into the particle dispersion chamber 85 so as to create a vortex of nebulized particles. The particles remain in a vortex and continue to travel in a manner even when exiting the particle dispersion chamber 85 and introduced into the nasal cavity and paranasal sinuses.

The particle dispersion chambers 85 described herein can also be adopted for use with current pressurized canister inhalers, dry powder inhalers, inhaler and other mechanisms for which medicine is breathed through the nose, mouth, or both including inhaling and exhaling through the same orifice or alternating between the orifices. A small pump 35, either hand-primed, electric, or battery powered or otherwise, is attached to a housing and is prepared to be actuated. Tubing 80 which leads to air ports 90 lead from the pump 35 to a particle dispersion chamber 85 placed over the exit off the actuator 120. The pump fires when the unit is actuated and creates a vortex of the particles prior to the medicament entering the nostril where it can be swirled into the nasal cavity. The pump 35 can be fired by hand and timed with the breathing process of the user with such versions as a dry powder inhaler which uses the user's breathing to release the powder into the system.

Figure 16:
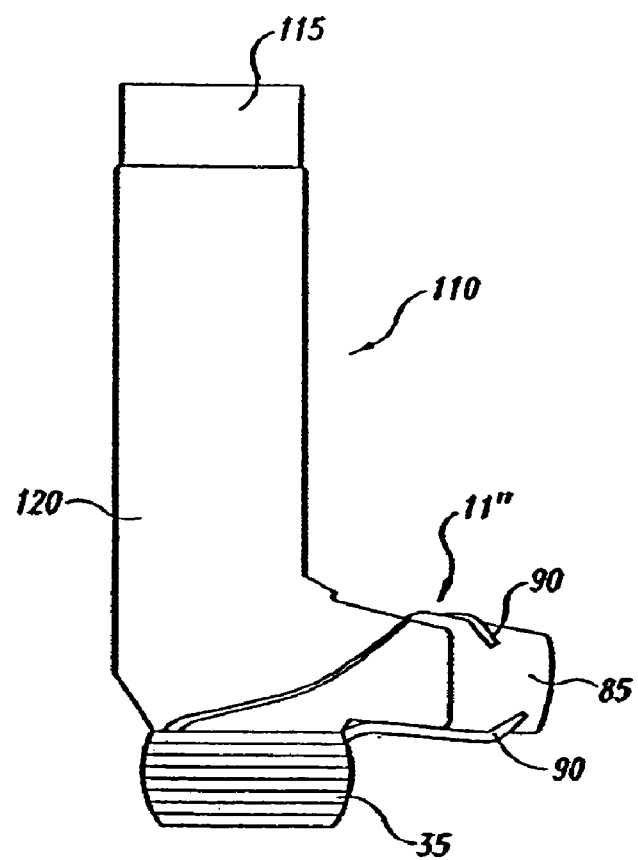
FIG. 16 shows an inhaler with one embodiment of a particle dispersion chamber.

FIG. 16 shows an inhaler 110 having a mouthpiece 11, a pump 35, a pressurized canister 115 of medicine, and an actuator 120. To the inhaler 110 can be attached at the mouthpiece 11 a particle dispersion chamber 85. The embodiment of FIG. 16 shows an inhaler 110 having a particle dispersion chamber 85 with a plurality of air outports 90, although other embodiments of the particle dispersion chamber 85 can be associated with the inhaler 110.

Figure 17:
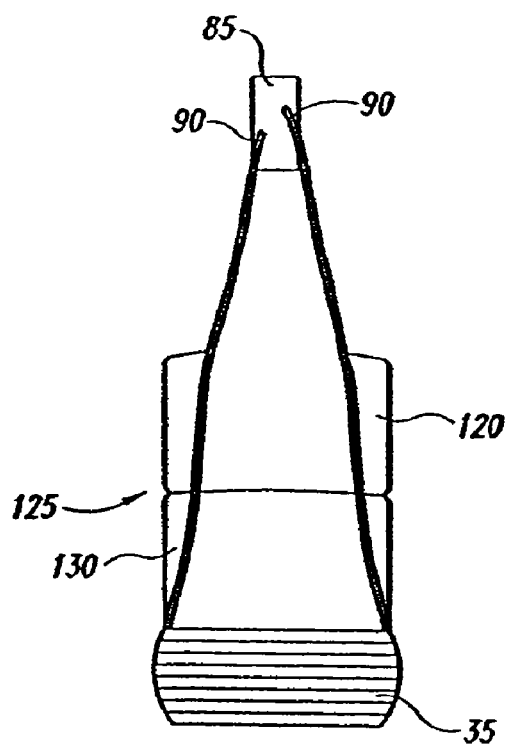
FIG. 17 shows a nasal spray with one embodiment of a particle dispersion chamber.

FIG. 17 shows a nasal spray 125 having a pump 35, a particle dispersion chamber 85 with a plurality of air ports 90, a nasal spray actuator 120, and a nasal spray medicine container 130. The embodiment of FIG. 17 shows a nasal spray inhaler 125 having a particle dispersion chamber 85 with a plurality of air outports 90, although other embodiments of the particle dispersion chamber 85 can be associated with the nasal spray inhaler 125.

Figure 18:
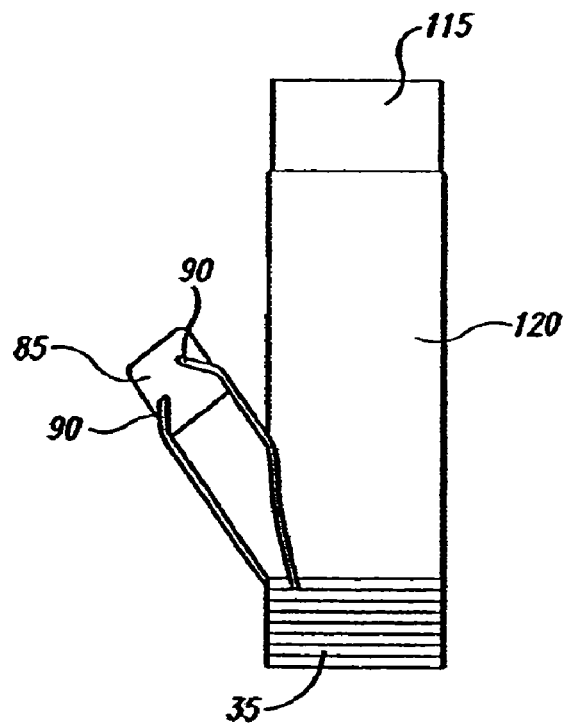
FIG. 18 shows a nasal inhaler with one embodiment of a particle dispersion chamber.

FIG. 18 shows an inhaler 110 having a pump 35, a pressurized canister 115 of medicine, and an actuator 120. To the inhaler 110 can be attached a particle dispersion chamber 85. The embodiment of FIG. 18 shows an inhaler 110 having a particle dispersion chamber 85 with a plurality of air outports 90, although other embodiments of the particle dispersion chamber 85 can be associated with the inhaler 110.

Figure 19:
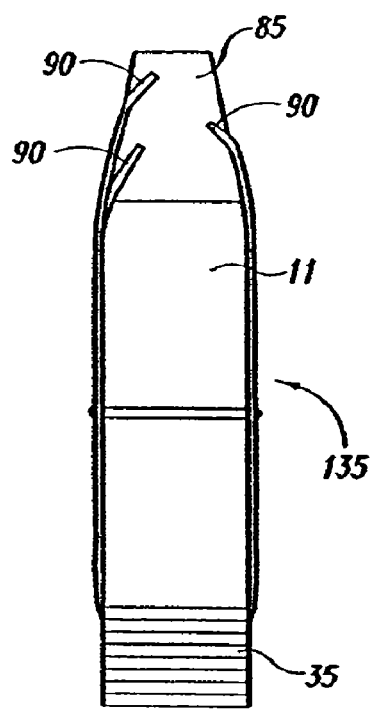
FIG. 19 shows a dry powder spinhaler with one embodiment of a particle dispersion chamber.

FIG. 19 shows a dry powder inhaler 135 having a mouthpiece 11 and a pump 35. To the dry powder inhaler 135 can be attached a particle dispersion chamber 85. The embodiment of FIG. 19 shows the dry powder inhaler 135 having a particle dispersion chamber 85 with a plurality of air outports 90, although other embodiments of the particle dispersion chamber 85 can be associated with the dry powder inhaler 135.

Figure 20:
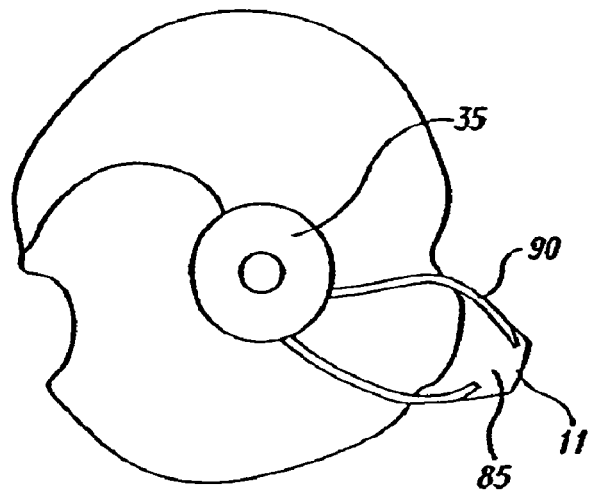
FIG. 20 shows a dry powder inhaler with one embodiment of a particle dispersion chamber.

FIG. 20 shows a dry powder inhaler 140 having a mouthpiece 11 and a pump 35. To the dry powder inhaler 140 can be attached a particle dispersion chamber 85. The embodiment of FIG. 20 shows the dry powder inhaler 140 having a particle dispersion chamber 85 with a plurality of air outports 90, although other embodiments of the particle dispersion chamber 85 can be associated with the dry powder inhaler 135. In a pulmonary application using a dry powder inhaler 140, the particle dispersion chamber 85 serves to break down the particles further reducing clumping and increasing the amount that reaches the lungs. In pulmonary inhaler versions, the medicament is greater dispersed and increases the opportunities for it to get into the throat without being blocked by the tongue. Research has shown that particle turbulence increases deposition into the lungs.

In yet another embodiment, there are two air outputs 90, or jets, and a third jet is used to spin the particles prior to them entering the chamber 45. This is designed to get the individual particles spinning prior to being put into the vortex in the chamber 45. This will allow the particles to get better "bounce" in the nasal cavity and deeper penetration and larger coverage area into the nasal cavity and the sinuses. This will be done for specific medicaments that could benefit from this action and will be turned off for medicaments that would not benefit from it.

In an additional embodiment (FIG. 36), prior to the nebulized particles entering the dispersion chamber 85, they will pass through a charge station where they will gain a negative or positive charge which causes the particles to repel each other and does not allow them to recombine into larger particles. The acquired charges cause the particles to repel each other in the chamber 85, the nasal cavity, and sinuses allowing for deeper penetration and larger coverage area. This is done for specific medicaments that could benefit from this action and are be turned off for medicaments that would not benefit from it.

In yet another embodiment of the nebulizer 25 as shown in FIGS. 25-28, the nebulizer 25 has a nebulizing chamber 150, a nebulizing compressor feed 155, and a particle dispersion chamber 85. The nebulizing chamber 150 has a concave or receptacle-like bottom 151. The nebulizing chamber 150 is oval shaped. The nebulizing compressor feed 155 allows for the introduction of fluid, for example, compressed air or other gasses. Further, the nebulizing compressor feed 155 allows, in particular aspects, for the exit from the nebulizing chamber 150 of air or other gases. Introduction and exit of the fluid from the nebulizing chamber 150 can be accomplished thru the use of a plurality of compressor channels 160. A nebulizer pressure cone 165, as shown in FIGS. 25 and 26, is found within the nebulizing chamber 150 and projects from the concave of receptacle-like bottom 151. Introduction of fluid into the nebulizing chamber 150 from the nebulizing compressor feeds 155 occurs thru a channel in the nebulizer pressure cone 165 having a fluid opening 166 at the top of the nebulizer pressure cone 165. A drug, therapeutic or beneficial compound can be introduced into the nebulizing chamber and will fill or partially fill the concave bottom 151. Located generally opposite the nebulizer pressure cone 165 is a particle dispersion chamber 85. In this embodiment, the particle dispersion chamber 85 projects into the nebulizing chamber 150. In one aspect of the particle dispersion chamber 85 as used with this embodiment of the nebulizer 25, the air outputs 90 are dispersion feed channels in the wall of the particle dispersion chamber 85 and molded from the same material as the particle dispersion chamber 85, for example. The particle dispersion chamber 85 has an opening thru which the nebulized particles may exit and which is capable of association with a mouth or nosepiece.

Figure 29A:
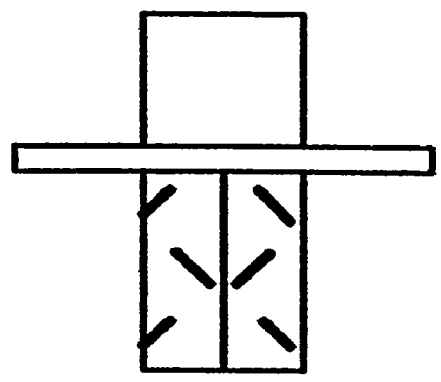
FIGS. 29A and 29B show a dispersion chamber plurality of particle sub-dispersion chambers.
Figure 29B:
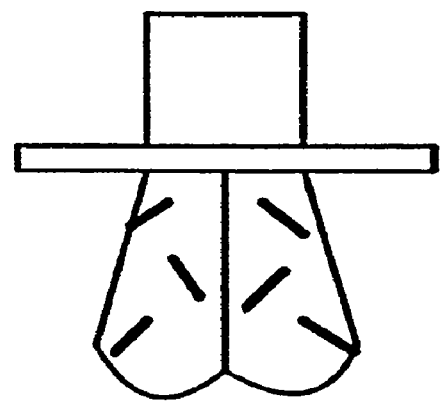

In another embodiment, as shown in FIGS. 29A and 29B, a nebulizer 25 contains a plurality of particle dispersion chambers 85. The plurality of particle dispersion chambers 85 may spin particles in the same or different direction, and may contain particles of the same or different size. The plurality of chambers 85 would flow into an upper chamber 175 capable of association with a nose piece or mouth piece.

In one manner of operation, a FFS ampoule 60 containing a medicament or the medicament itself is placed into the medicine chamber 45 of the nebulizer 25 shown in FIG. 1. The nasal adapter 10 is fitted over the nose of the user and the nebulizer 25 is activated. The user breathes using the BT. More particularly in operation:

1. In FIG. 1, the lid 50 is lifted to the medicine chamber 45 and the prescribed dosage of medicine is poured in. The lid 50 is then closed.

2. The nasal adapter 10 is lifted from its compartment 2, shown in FIG. 1, in the topside of the nebulizer 25 to the required height.

3. As shown in FIG. 11, the nasal adapter 10 is placed over the nose and pressed into place to seal in the nebulized particles.

4. As shown in FIG. 3, the timer 4 is set to the required time for the drug being used.

5. As shown in FIG. 3, the start button 6 is activated, for example, by being depressed.

6. The user breathes using the BT, but inhaling and exhaling out the mouth as needed to maintain oxygen levels.

7. When the timer 4 stops the nebulizer 25, if it is being used for a single dose treatment, the nasal adapter 10 is replaced in its compartment 2 and the medicine chamber 45 is cleaned.

Preferably, the nebulizer 25 is allowed to dry fully before reusing. If using for a multiple dose treatment, it should be cleaned after each dosage is complete. The nebulizer 25 disclosed herein is capable of delivering nebulized particles far into the nasal cavity and the paranasal sinuses.

In another method of operation, the user uses the nebulizer 25, or any other art-recognized nebulizer (or even standard spray bottle-type 'nebulizers'), in conjunction with a novel Controlled Particle Dispersion Breathing Technique (BT). The novel BT provides for the nebulized particles to reach deeply into the nasal cavity and paranasal sinuses. The BT includes placing the nasal adapter 10 of the nebulizer 25 over the nose of the patient and activating the nebulizer 25. As nebulized particles begin to flow out of the particle dispersion chamber 85, the user should take long, slow steady breaths alternating with approximately one to five quick breaths, preferably two to four quick breaths, and even more preferably three breaths, through the user's nose. The breath(s) should be held for approximately one to five seconds and more preferably for three seconds. Using the back of the throat, the user should then create pressure in their sinuses such as when relieving pressure due to a change in altitude when traveling in a car or plane. This allows the medicine to remain in the nasal cavity and aids in delivery of the medicine to the sinuses. This pressure should be used during both types of breathing. The breathing, breath holding, and pressure creation should be performed throughout the treatment. Preferably, the user should follow with three long, slow, deep breaths through the nose. More preferably, the user should follow with two long, slow deep breaths through the nose. Most preferably, the user should follow with one long, slow, deep breath through the nose. The above discussed breathing, breath holding, pressure creation, and slow, long deep breaths are then repeated until the treatment is complete. It is advised that when dealing with severe cases of sinus congestion, the user should be instructed to breathe through the mouth as needed to maintain necessary oxygen intake. Although the BT involves breathing in through the nose, it is understood that infants, children, the elderly and others with serious breathing problems may perform the BT through the mouth or through cooperatively the mouth and nose.

The nebulizer 25 disclosed herein is capable of delivering nebulized particles far into the ethmoid, maxillary and sphenoid sinus. The sphenoid sinus is located furthest from the nasal cavity. The ethmoid, maxillary and sphenoid sinuses have not been penetrated in the past through any other prior art technology. The delivery of medicament to the ethmoid, maxillary and sphenoid sinuses has been shown through sinus ventilation studies.

Preferably, the inventive nebulizer and methods deliver (nasally) nebulized particles comprised of particles substantially having a mean diameter of about 2 to about 50 μm, about 5 to about 50 μm, about 5 to about 40 μm, about 5 to about 35 μm, about 5 to about 30 μm, about 5 to about 20 μm, about 5 to about 17 μm, about 5 to about 15 μm, about 8 to about 30 μm, about 8 to about 20 μm, about 10 to about 30 μm, about 10 to about 25 μm, about 10 to about 20 μm, about 10 to about 17 μm, about 10 to about 15 μm, about 11 to about 40 μm, about 11 to about 30 μm, about 11 to about 20 μm, about 11 to about 15 μm, about 12 to about 17 μm, about 15 to about 25 μm, about 15 to about 20 μm, and about 17 to about 23 μm.

Preferably, the nasally delivered nebulized particles are comprised of particles substantially having a mean diameter of about 5 to about 30 the delivered nebulized particles are comprises of particles substantially having a mean diameter of about 5 to about 30 μm, about 10 to about 20 μm, about 10 to about 17 μm, about 10 to about 15 μm, and about 12 to about 17 μm.

Preferably, the nasally delivered nebulized particles are comprised of particles substantially having a mean diameter of about 10 to about 15 µm, or about 12 to about 15 µm.

PREFERRED EMBODIMENTS

Preferably, the nebulizers of the present invention are used to deliver drugs, therapeutics and other beneficial compounds systemically.

Systemic delivery via inhalation utilizing the nasal mucosa and mucosa in the paranasal sinuses is desired for many targeted disease states, and the nebulizers of the present invention are well suited for this purpose. The nebulizer 16 of FIG. 30, for example, is suited to deliver many drugs that are currently prescribed for many diseases. The inventive delivery is as very tiny particle doses of medicine via a nasal adapter 24 that allows more efficacious sinus penetration and systemic delivery for the user. Examples of diseases that can be treated by systemic delivery using the inventive devices include, but are not limited to endocrine and metabolic disorders, migraines, sleep disorders, autoimmune diseases, osteoporosis, neurological diseases and disorders, obesity, sexual dysfunctions, and cardiovascular diseases and episodes. The particle sizes, time of application and particle dispersion technology allow the medicine to reach and permeate the paranasal sinuses. These factors allow for systemic delivery of the medicine via the nasal cavity (paranasal sinuses). All medicines currently applied by direct action to the nasal cavity and paranasal sinuses are adaptable for use with the inventive nebulizer 16, including over-the-counter nasal medicines for allergy, colds and flu. Many medicines currently taken orally, by skin patch, or parenterally are adaptable for use with the inventive nebulizers (e.g., nebulizer 16).

For a user with a secondary condition of nasal polyps, the inventive apparatus and methods allow far more effective application of the medicine, which is otherwise blocked or precluded using contemporary systems. Prior art corticosteroid-based inhalers are designed to also slow the re-growth of polyps following their removal. Currently, however, such devices are largely ineffective at accomplishing this, often slowing polyp growth at all. According to the present invention, the apparatus and methods described herein are significantly more effective in slowing polyp re-growth following their removal.

Many of the side effects of some medicines are eradicated by the inventive devices and methods. With many sprays, for example, the propellant causes a drying of the nasal passages leading to bleeds. With the use of contemporary devices that lead to bleeds, a secondary spray of saline is added to the treatment to try and control the bleeding. Furthermore, steroids in pill form have many unpleasant side effects such as internal bleeding, a redistribution of fluid to the head, neck and back causing unsightly "humps," and easy bruising, to name a few. An effective use of the inventive integrated nebulizer does not have these side effects associated with steroids in pill form.

The inventive integrated nebulizer will allow medicine to be administered to the nasal cavity and paranasal sinuses via very small particles that will penetrate deeply into the nasal cavity, most regions of the paranasal sinuses, and allow for systemic delivery. The inventive integrated nebulizer will also provide the patient with a more effective absorption of the drug, increasing effectiveness, and will allow multiple conditions to be treated in a far more effective manner.

Typically, since the medicine is delivered in a treatment and not an attack scenario, the application or delivery time is only 0.5-3 minutes, rather than the 10-15 minutes used during an asthma attack. Multiple dose levels of the medicine can be placed in the inventive integrated nebulizer, a week supply for example, and the unit will run for a prescribed time, for example but not limited to three minutes, and will then, in particular embodiments, shut itself off. Preferably, the inventive integrated nebulizer is designed with multiple dose capability and a timer with a pause feature. The pause feature allows the user to stop the treatment under way to deal with a short, minor happenstance and then resume the treatment for the remaining time. The timer is variable to accommodate the drug being administered and/or prescribed by the physician.

Figure 30:
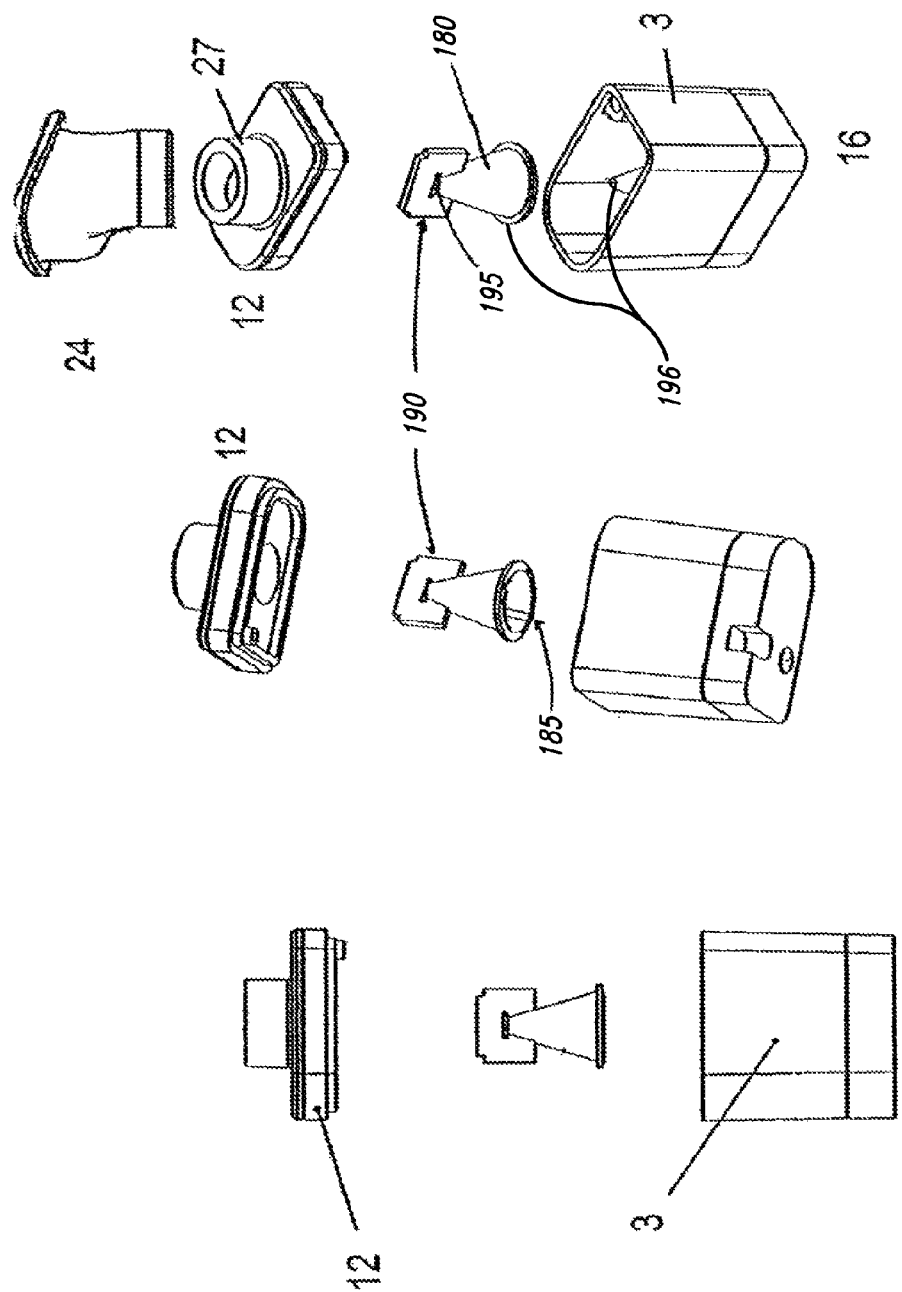
FIG. 30 is a perspective view of an illustrative embodiment of the inventive integrated nebulizer and particle dispersion chamber for nasal delivery with major components shown separately.

FIG. 30 shows an inventive nasal adapter 24 that has been designed to attach to the outflow tube 27 of the nebulizer 16 (i.e, outflow from the partical dispersion chamber of the nebulizer) and facilitate delivery of the medicine to the nose alone. The nasal adapter 24 limits various unwanted occurrences such as delivery of any medicament to the eyes and face surrounding the nose and into the general environment.

Use of a nasal adapter 24 also limits the spread and growth of bacteria or microorganisms. Use of a nasal adapter 24 reduces the spread of bacteria that can be picked up from inside the nasal openings as is the case with current MDI's or AQ sprays. Further, use of a disposable version of nasal adapter 24 reduces the occurrence of re-inoculation of the nasal openings with bacteria present on the nasal adapter 24, when not properly cleaned.

The nebulizer 16 is designed to accommodate daily use. The substantially compact size of the nebulizer allows for easy transport and discreet use.

Disrupting the air flow. A significant aspect of the inventive controlled particle dispersion technology is that it disrupts the air flow that air takes when passing through the nasal cavity through inhalation. This disruption allows the particles access to the upper and posterior sections of the nasal cavity and entry into the paranasal sinuses. This disruption can be, for example, a vortical, chaotic, or random mixing of the particles just prior to exiting the device with added but limited effect. Preferably, induction of vortical flow is the most efficient and effective means of disrupting the air flow but other means can accomplish this with the same goal of disrupting the air flow for better deposition in the nasal cavity.

As shown in FIG. 30, the nebulizer 16 is an integrated particle dispensing chamber. The nebulizer 16 comprises a particle dispersion chamber 12, which is in communication with a nasal adapter 24. As the nebulized particles pass through the particle dispersion chamber 12, they are dispersed (e.g., swirled into a vortex, chaotic, or other random movement) and emerge from the chamber 12 in such dispersed movement (e.g., vortical flow) into the nasal cavity and the paranasal sinuses. In this process, particles advantageously enter the nasal cavity at many angles. The particles also bounce or ricochet within the nasal cavity, allowing the particles to get by the nasal "concha" (turbinates) and reach previously inaccessible areas.

Further, the particles delivered by the inventive devices afford systemic delivery through the paranasal sinus membranes. The particles can be delivered across the nasal and sinus mucosal membranes to enter the systemic blood circulation to treat medical conditions elsewhere in the body. Treatments for medical conditions include, but are not limited to, treatments for pain management, sleep disorders, autoimmune diseases, neurological disease and disorders, and weight control, etc. Compounds that can be delivered include, but are not limited to, synthetic and natural peptides, proteins, antibodies, hormones, vaccines, DNA and RNA, sugars, carbohydrates, and lipids. Delivered compounds can also include small synthetic organic pharmaceuticals, radiopharmaceuticals, vitamins, homeopathic solutions or any pharmaceutical, with or without additional formulation to aid in the stability or to aid in the crossing of the mucosal membrane by the compound. The critical aspects, according to the present invention are the preferred particle size, and the randomized or vertical motion imparted by the inventive devices and methods.

Figure 37:
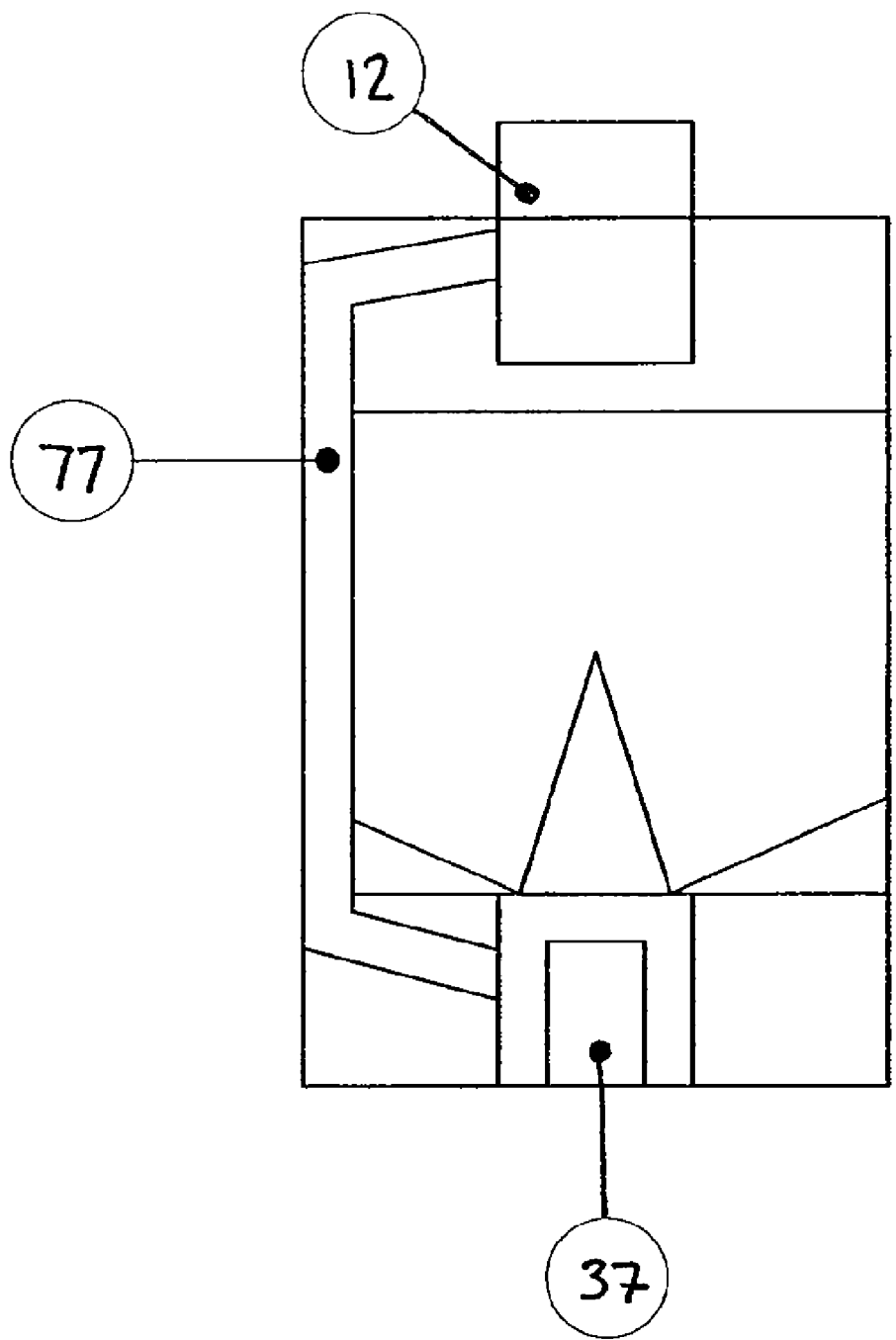
FIG. 37 is a cross-sectional view of an additional embodiment of the inventive integrated nebulizer and particle dispersion chamber.

In another embodiment, the nebulizer 16 shown in FIG. 37 has a particle dispersion chamber 12 that projects into the nebulizing chamber 3. In one aspect of the particle dispersion chamber 12 as used with the embodiment shown in FIG. 37, the dispersion feed channel 77 bleeds compressed air or fluid from one compressor channel 57 and directs it into the dispersion chamber 12 where it enters at an angle and creates a vortex of randomized motion of the particles.

Preferred Jet Nebulization Embodiments

Figure 31:
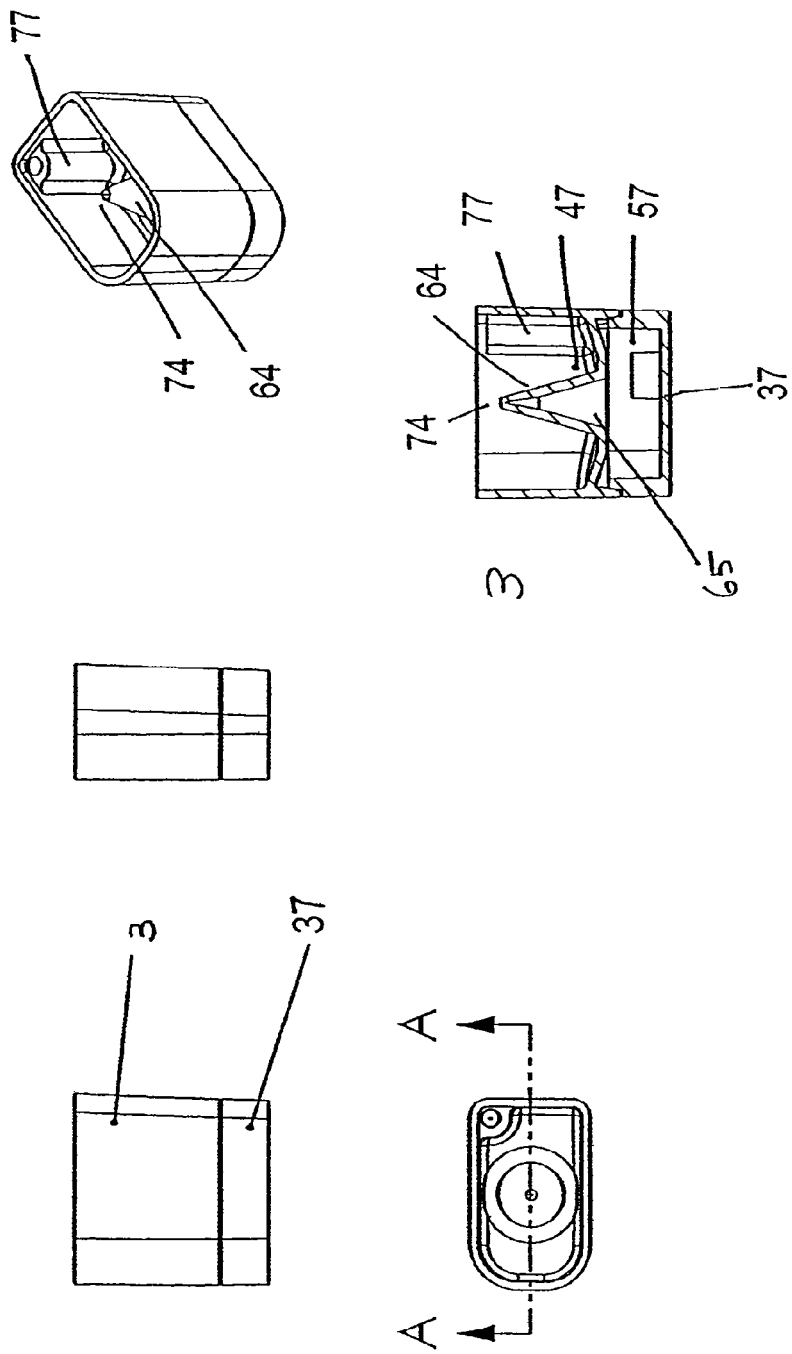
FIG. 31 is a cross sectional view of the illustrative integrated nebulizer and particle dispersion chamber embodiment of FIG. 30.
Figure 32:
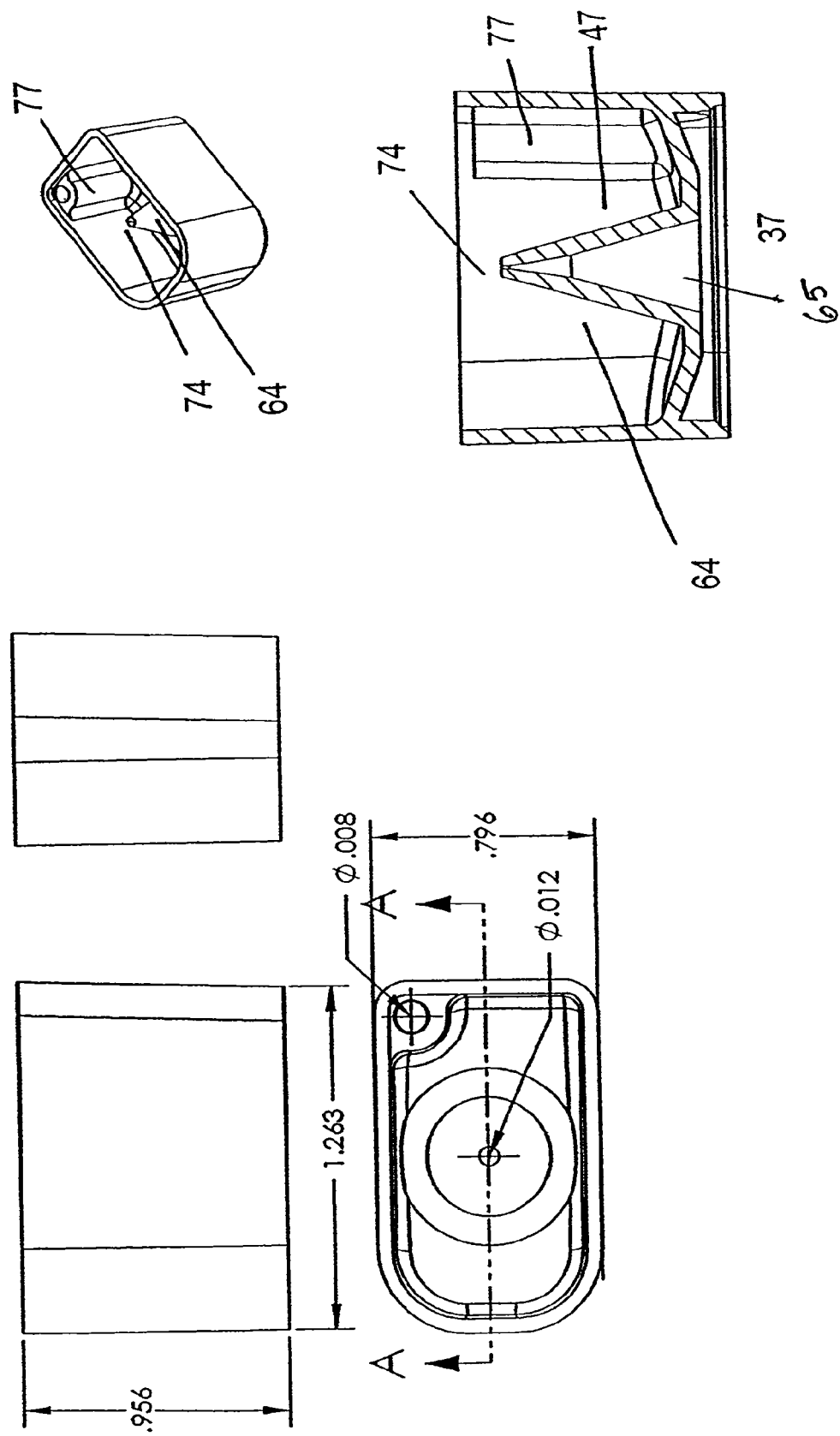
FIG. 32 is an enlarged cross sectional view of the of the illustrative integrated nebulizer and particle dispersion chamber embodiment of FIGS. 30 and 31.

A preferred embodiment of the nebulizer 16 is shown in FIGS. 30-35. The nebulizer 16 has a nebulizing chamber 3, a nebulizing compressor feed 37, and a particle dispersion chamber 12. The nebulizing chamber 3 has a concave or receptacle-like bottom 47. The nebulizing compressor feed 37 allows for the introduction of fluid, for example, compressed air or other gasses, or combinations thereof. Further, in particular aspects, the nebulizing compressor feed 37 allows for the exit from the nebulizing chamber 3 of air or other gases. Introduction and exit of a fluid from the nebulizing chamber 3 can be accomplished through the use of a plurality of compressor channels 57. A pressure release member 64, as shown in FIGS. 30-32, is found within the nebulizing chamber 3 and, in preferred embodiments, projects from the concave of the receptacle-like bottom 47. The pressure release member 64 comprises a pressure release channel 65 and a pressure release orifice 74 located substantially at the vertex of the pressure release member 64. FIGS. 31 and 32 show a dispersion feed channel 77 that is fed from a compressor channel 57 or nebulizing compressor feed 37. In this embodiment, dispersion feed channel 77 is partially diverted from the nebulizer compressor feed 37 and is located within or along the wall of the nebulizing chamber 3 and molded from the same material as the nebulizing chamber 3. Introduction of compressed fluid into the nebulizing chamber 3 from the nebulizing compressor feed 37 occurs through a pressure release channel 65 in the pressure release member 64 having a pressure release orifice 74 at the top of the pressure release member 64. The compressed fluid (e.g., air and/or gas) is directed up through the pressure release channel and member to a pressure release orifice 19 located substantially at the vertex of the pressure release member. A drug, therapeutic or beneficial compound can be introduced into the nebulizing chamber 3.

An impacter 180 (see FIGS. 30 and 33) fits over and substantially conforms to the surface (e.g., conical) of the pressure release member 64. The impacter 180 has a top opening 195 in communication with the pressure release orifice 74 to allow compressed fluid to travel from the pressure release orifice 74 through the top opening 195 of the impacter 180. The impacter 180 additionally comprises an obstructing member 190 that spans a position directly above the top opening 195, and thereby redirects the path of emerging fluid at generally right angles into the nebulizer chamber. The impacter 180 further comprises a medicament channel 185 that is recessed into the inner wall of the impacter such that the medicament channel 185 runs adjacent to the external surface (e.g., conical) of the pressure release member 64 (when the impacter is in place on the pressure release member), and further is in communication with the lower concave or receptacle-like bottom 47 of the nebulizing chamber, and the top opening 195 of the impacter 180. During operation of the nebulizer, liquid medicament is drawn (by virtue of the flow of compressed fluid through the pressure release orifice 74 and impacter top opening 195) from the base of the nebulizing chamber 47 up through the medicament channel 185 to the orifice 74 and top opening 195 of the impacter where the liquid is nebulized into droplets and directed by the impacter into the nebulizer chamber.

Figure 34:
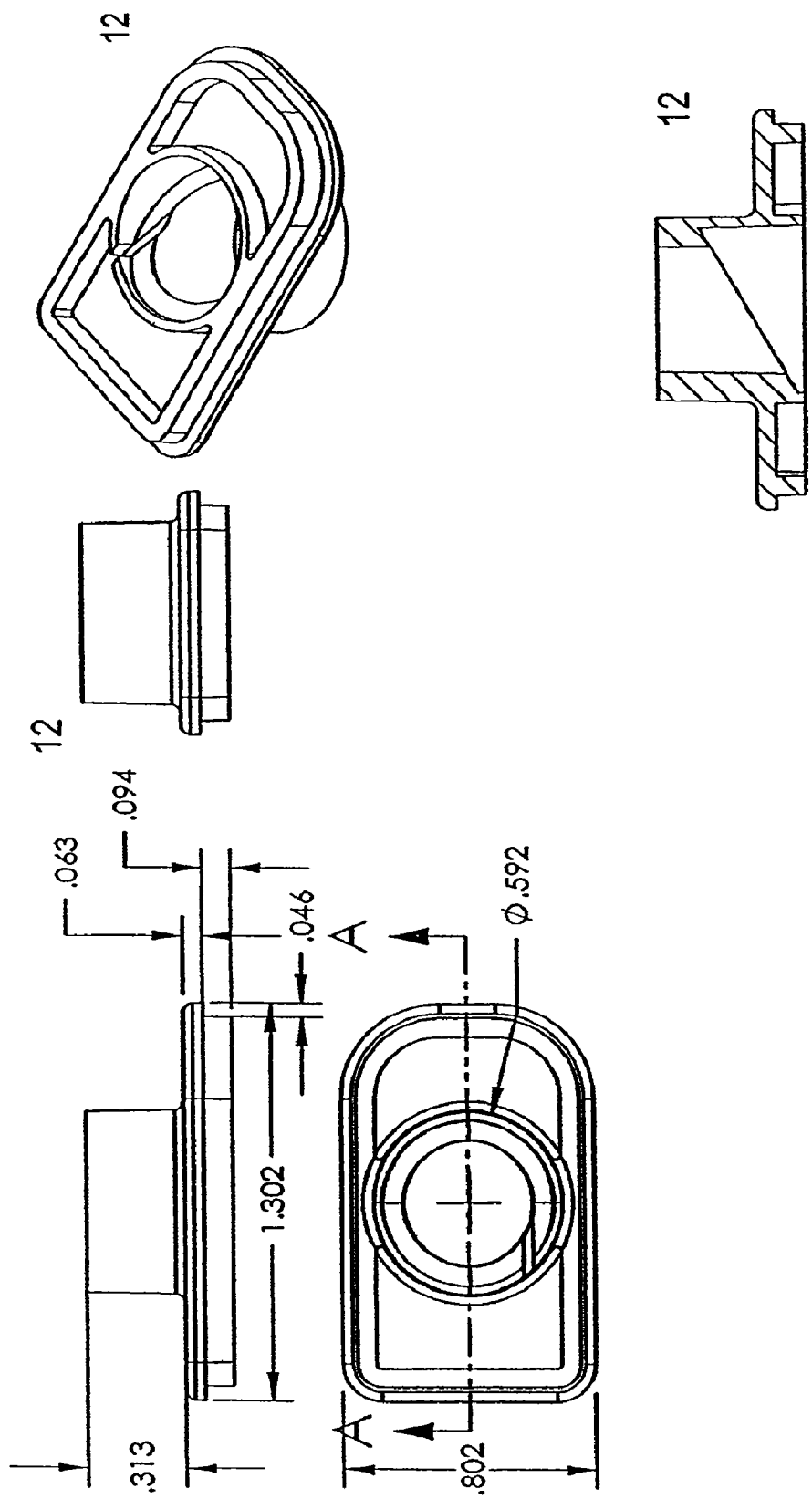
FIG. 34 is a cross sectional and perspective view of the particle dispersion chamber of the illustrative integrated nebulizer and particle dispersion chamber embodiment of FIGS. 30-33.
Figure 35:
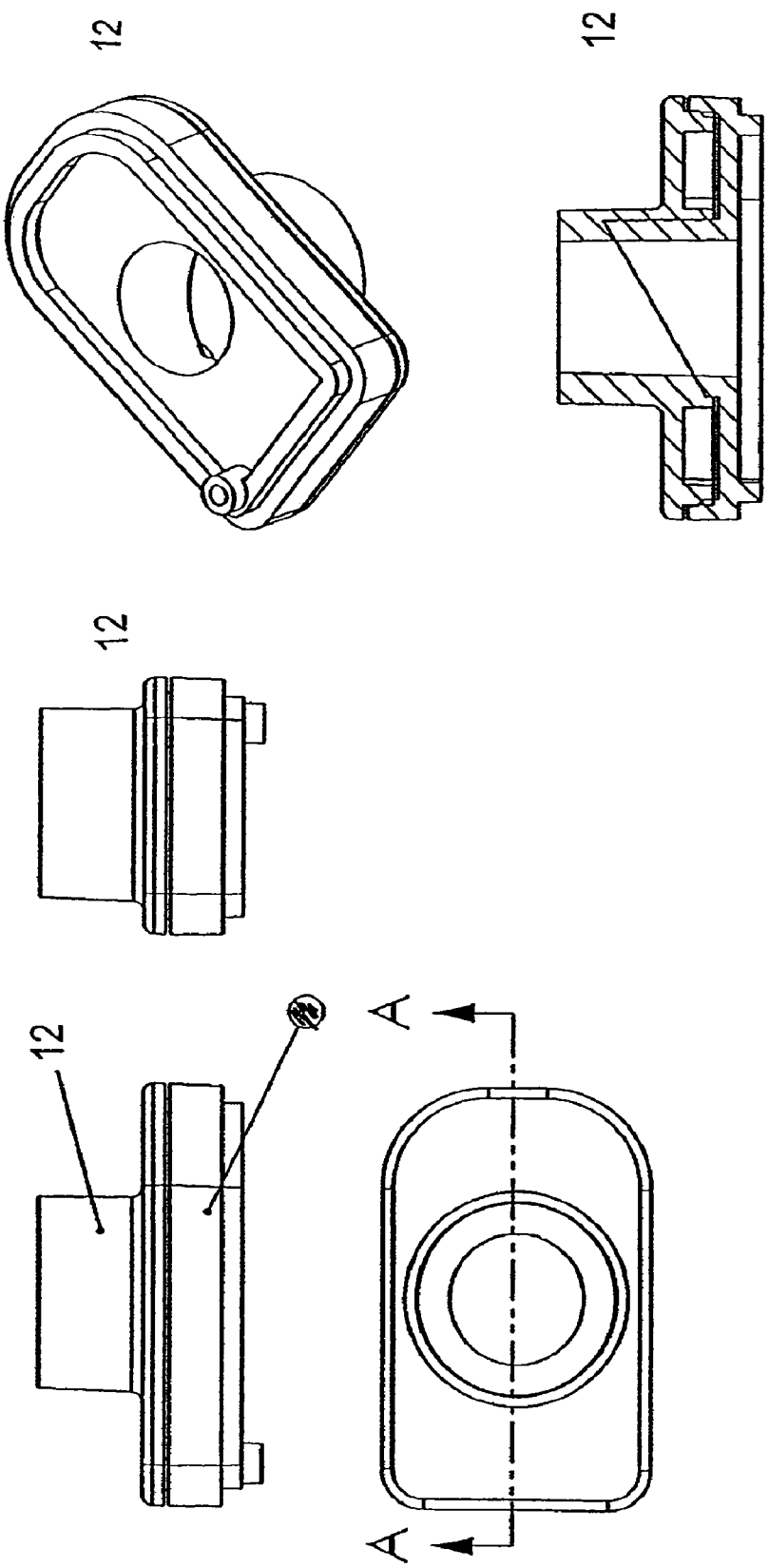
FIG. 35 is an enlarged cross-sectional and perspective view of the particle dispersion chamber of the illustrative integrated nebulizer and particle dispersion chamber embodiment of FIGS. 30-34.

Located generally opposite the pressure release member 64 and impacter 180 is a particle dispersion chamber 12 (see FIGS. 30 and 34). In this embodiment, the particle dispersion chamber 12 forms an integral unit with the nebulizing chamber 3. They can be made separately and fit together or be formed from the same mold or unitary material. In one aspect of the particle dispersion chamber 12 as used with this embodiment of the nebulizer 16, a dispersion feed channel 77 is adjacent to the wall within the particle dispersion chamber 12 (and/or nebulization chamber) and molded from the same material as the particle dispersion chamber 12 (and/or nebulization chamber), for example. The particle dispersion chamber 12 has an opening or aperture through which nebulized, dispersed (e.g., vortical flow) particles may exit, and which is capable of association with a mouth or nosepiece (nasal adapter).

Figure 36:
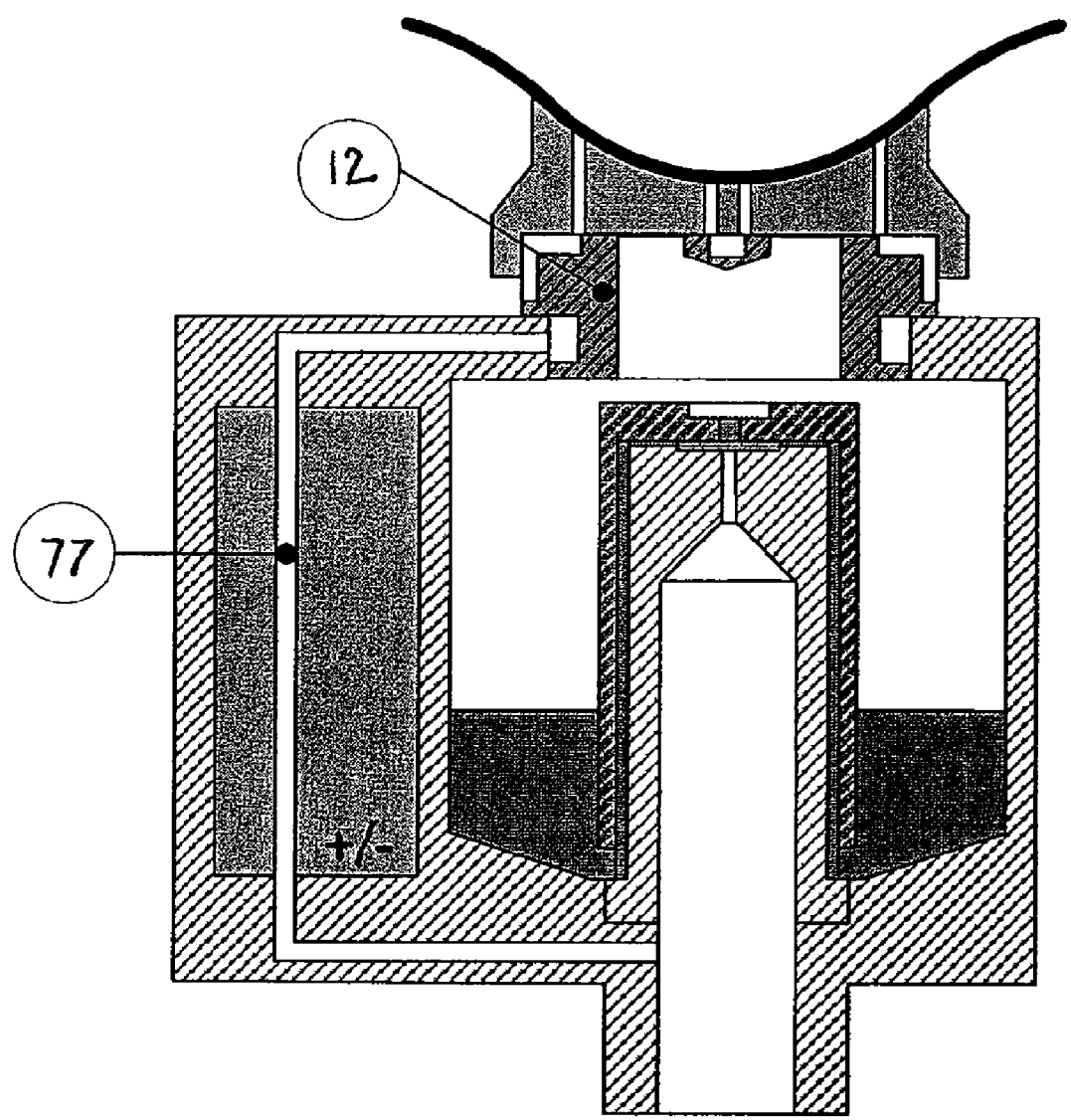
FIG. 36 is a cross-sectional view of an alternate illustrative embodiment of the inventive integrated nebulizer and particle dispersion chamber.

In another embodiment, the nebulizer 16 shown in FIG. 36 has a particle dispersion chamber 12 that projects into the nebulizing chamber 3. In one aspect of the particle dispersion chamber 12 as used with the embodiment shown in FIG. 36, the dispersion feed channel 77 feeds into the particle dispersion chamber 12 to disperse (e.g., create a vortex or randomized motion in) the particles in the dispersion chamber 12. The dispersion feed channel 77 is partially diverted from the nebulizer compressor feed 37, and travels outside of the nebulizing chamber wall to the particle dispersion chamber.

In another embodiment, the nebulizer 16 shown in FIG. 37 has a particle dispersion chamber 12 that projects into the nebulizing chamber 3. In this embodiment, the dispersion feed channel 77 bleeds compressed air or fluid from one compressor feed channel 57 and directs it into the dispersion chamber 12 where it enters at an angle and disperses (e.g., creates the vortex of randomized motion of) the particles. In this embodiment, fluid travels from the compressor channel to the dispersion feed channel(s) through a path within the wall of the nebulizing chamber.

The nebulizer 16 disclosed herein is capable of delivering nebulized particles far into the nasal cavity and the paranasal sinuses. In another method of operation, the user uses the nebulizer 16 in conjunction with a Controlled Particle Dispersion Breathing Technique (BT). The BT provides for the nebulized particles to reach deeply into the nasal cavity and paranasal sinuses. The BT includes placing the nasal adapter 24 to the nose of the patient and activating nebulizer 16. As nebulized particles begin to flow out of the particle dispersion chamber 12, the user should take long, slow steady breaths alternating with approximately one to five quick breaths, preferably two to four quick breaths, and even more preferably three breaths, through the user's nose. The breath(s) should be held for approximately one to five seconds and more preferably for three seconds. Using the back of the throat, the user should then create pressure in their sinuses such as when relieving pressure due to a change in altitude when traveling in a car or plane. This allows the medicine to remain in the nasal cavity and aids in delivery of the medicine to the sinuses. This pressure should be used during both types of breathing. The breathing, breath holding, and pressure creation should be performed throughout the treatment. Preferably, the user should follow with three long, slow, deep breaths through the nose. More preferably, the user should follow with two long, slow deep breaths through the nose. Most preferably, the user should follow with one long, slow, deep breath through the nose. The above discussed breathing, breath holding, pressure creation, and slow, long deep breaths are then repeated until the treatment is complete. It is advised that when dealing with severe cases of sinus congestion, the user should be instructed to breathe through the mouth as needed to maintain necessary oxygen intake. Although the BT involves breathing in through the nose, it is understood that infants, children, the elderly and others with serious breathing problems may perform the BT through the mouth or through cooperatively the mouth and nose.

The nebulizer 16 disclosed herein is capable of delivering nebulized particles far into the ethmoid, maxillary and sphenoid sinus. The sphenoid sinus is located furthest from the nasal cavity. The ethmoid, maxillary and sphenoid sinuses have not been penetrated in the past through any other prior art technology. The delivery of medicament to the ethmoid, maxillary and sphenoid sinuses has been shown through sinus ventilation studies.

Figure 46:
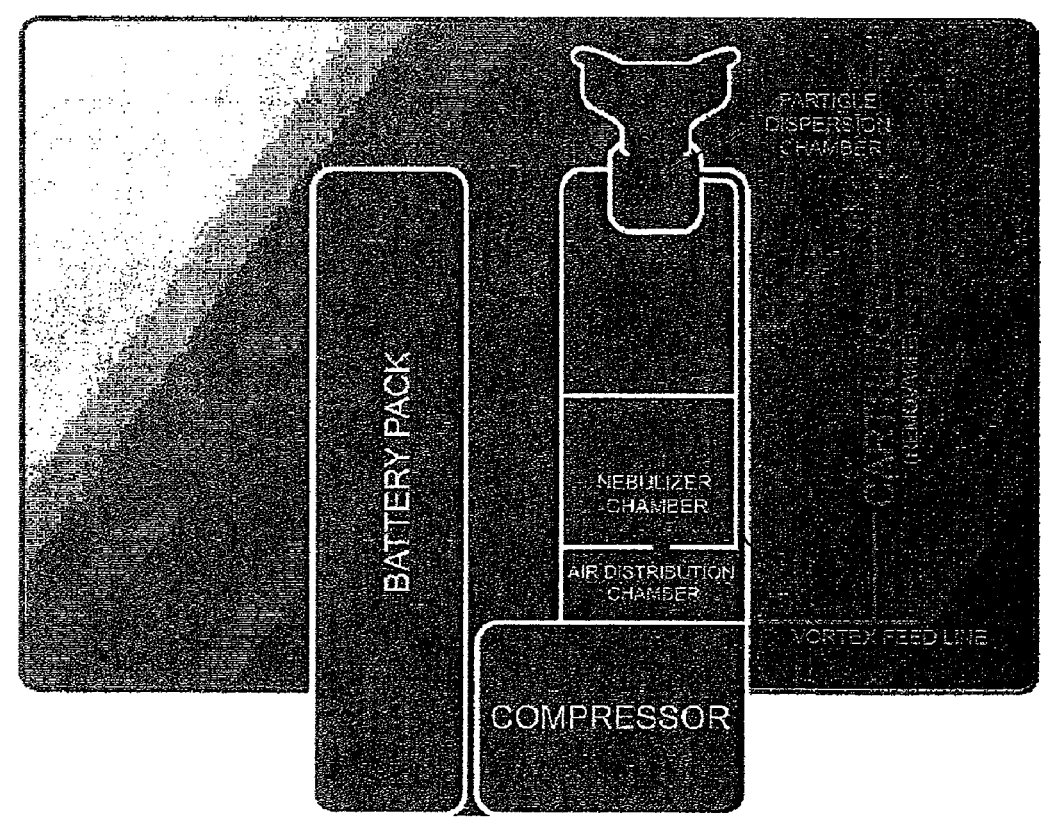
Figure 47:
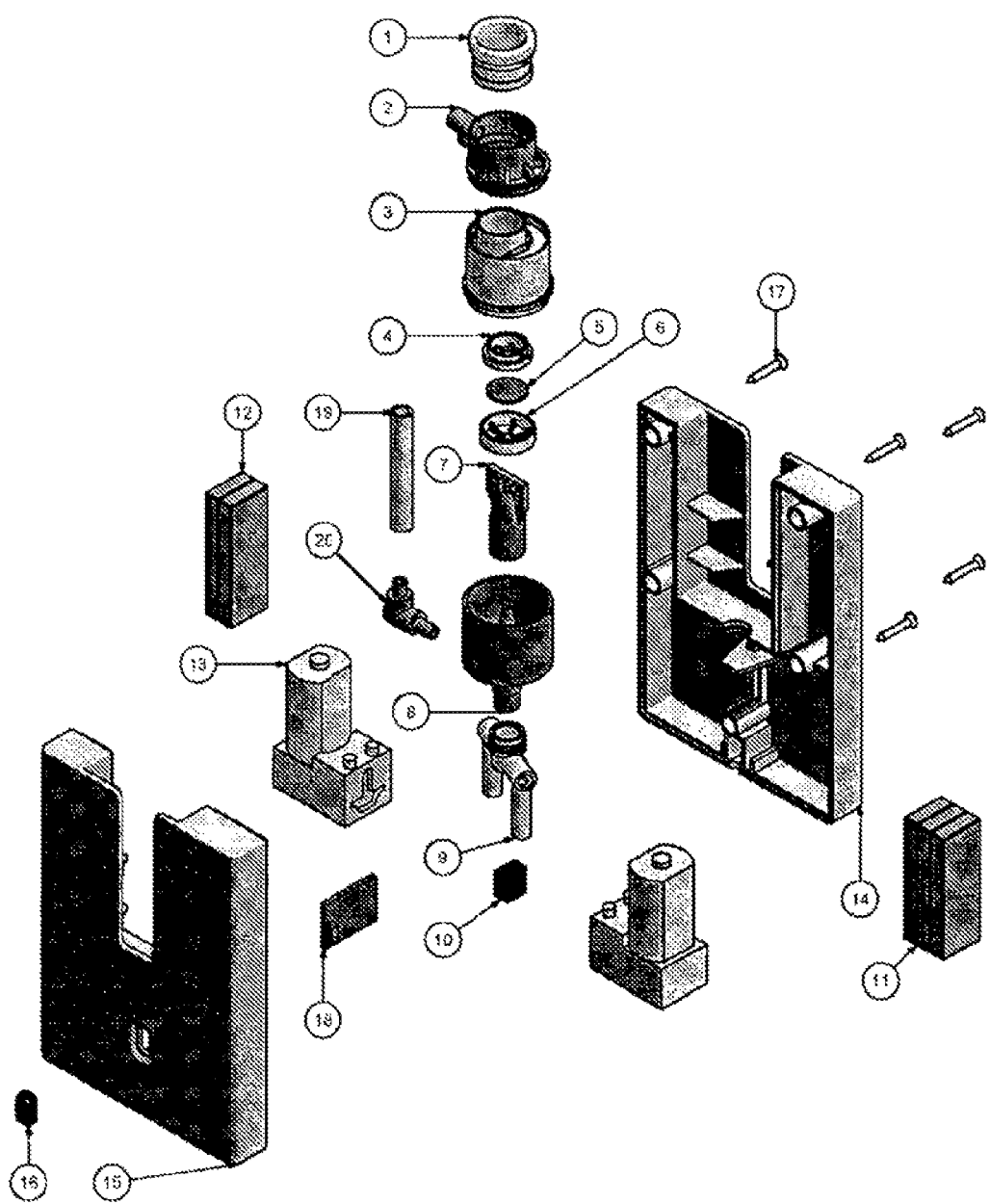
FIG. 47 and FIG. 48 show a particularly preferred embodiment of the inventive integrated nebulizer and particle dispersion chamber.
Figure 48:
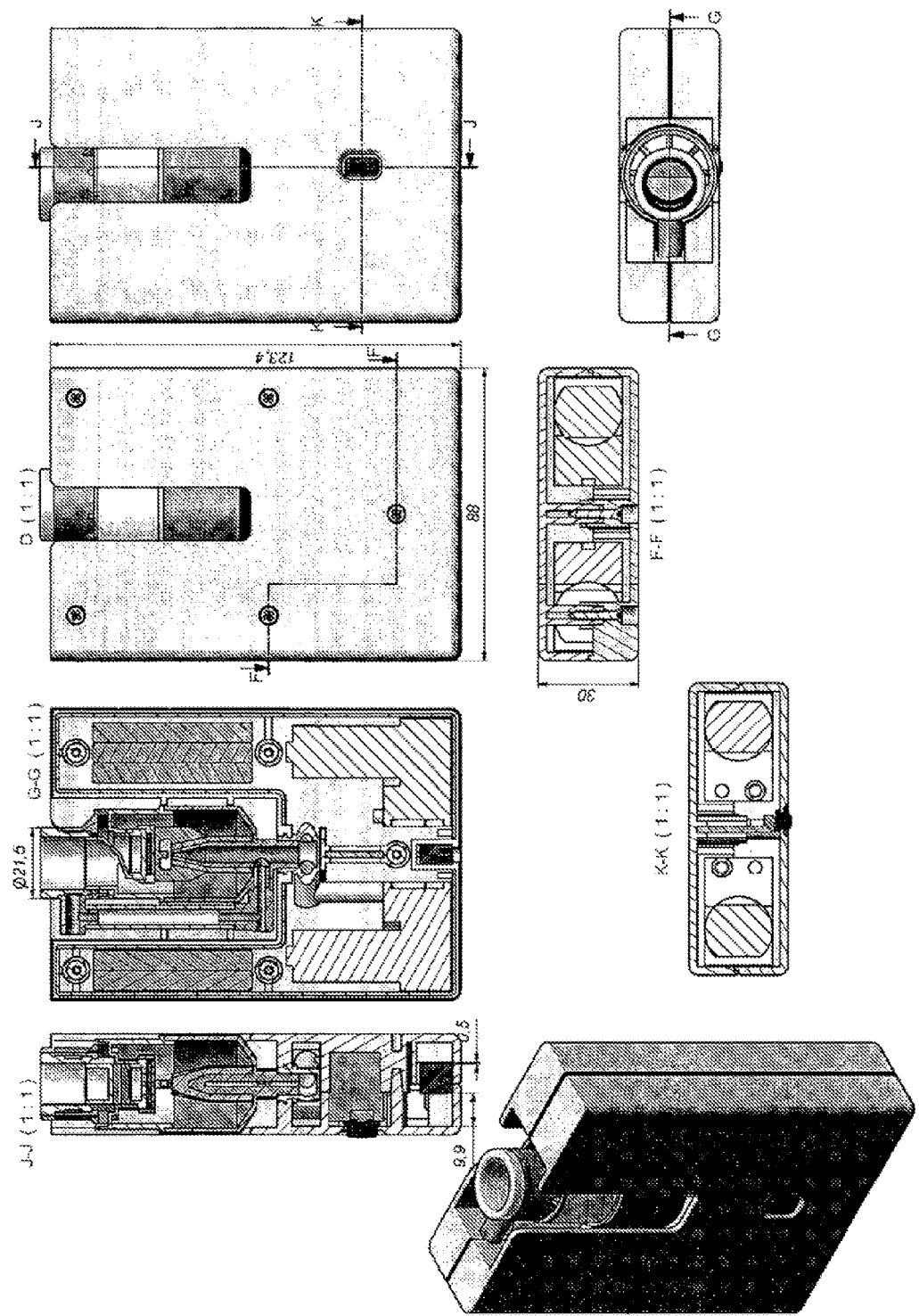

A particularly preferred embodiment of the present invention is shown in FIGS. 46, 47 and 48. Preferably, the device is constructed of, or substantially comprises, medical grade polycarbonate or acrylic material, although other art-recognized materials will suffice. The device comprises a housing having two halves 14 and 15, which are held together, for example, by screws or pins (or the equivalent thereof) 17. Alternatively, the housing could be sealed, snapped or otherwise held together. Batteries 11 and 12, and battery powered compressor pumps (fluid pumps) 13 are accommodated within the lower regions of the housing. The compressor units are activatable by engaging a switch means 16 and 18. A male plug connector 10 is also provided for compressor activation using an external power source. In alternate embodiments there may be only a single battery 11 (to power one or more compressor pumps 13), or a single compressor pump 13 (powered by one or more batteries 11). Alternatively, compressed air cartridges may be used in place of batteries, or in place of batteries and compressors. Compressed fluid is directed from the compressor pumps 13 toward the pressure release channel 8 of the nebulizing pressure release member (conical member projecting into the nebulizer chamber) of the nebulizer chamber via compressor channels 9. In the instant embodiment, the compressor channel is a manifold that combines and directs the compressed fluid (e.g., air, gas, or combinations thereof) from two compressors 13 to the pressure release channel 8 entering into the pressure release member projecting the nebulizer chamber. The nebulizer chamber, in this instance, is formed of lower and upper 3 cylindrical portions. The compressed fluid (e.g., air and/or gas) is directed up through the pressure release channel and member to a pressure release orifice 19 located substantially at the vertex of the pressure release member. An impacter 7 fits over and substantially conforms to the conical surface of the pressure release member. The impacter has a top opening 20 in communication with the pressure release orifice 19 to allow compressed fluid to travel from the pressure release orifice through the top opening of the impacter. The impacter additionally comprises an obstructing member that spans a position directly above the top opening 20, and thereby redirects the path of emerging fluid at generally right angles into the nebulizer chamber. The impacter further comprises a medicament channel (see e.g., the analogous impacter channel 185 of FIGS. 30 and 33) that is recessed into the inner wall of the impacter such that the medicament channel runs adjacent to the conical external surface of the pressure release member (that is, when the impacter is in place on the pressure release member), and further is in communication with the lower concave or receptacle-like bottom of the nebulizing chamber, and the top opening 20 of the impacter. During operation of the nebulizer, liquid medicament is drawn (by virtue of the flow of compressed fluid through the pressure release orifice 19 and impacter top opening 20) from the base of the nebulizing chamber up through the medicament channel to the top opening of the impacter where the liquid is nebulized into droplets and directed by the impacter into the nebulizer chamber. In addition to the nebulizing fluid entering the nebulization chamber from the pressure release channel/member 8, supplemental air required by a breathing user enters the nebulization chamber through an opening 18 in the top surface of the upper 3 cylindrical portion of the nebulization chamber. In some embodiments, the supplemental air thus enters the nebulizing chamber and combines with the nebulizing fluid (e.g., air, gas) and nebulized particles.

Preferred embodiments comprise a supplementary inhalation channel integral to or in direct communication with the nasal adapter, the inhalation channel at one end in communication with ambient air, and the other end being positioned adjacent to and in communication with the perimeter of the nasal-proximal aperture of the adapter channel. Preferably, the nasal-proximal end of the inhalation channel is annular, positioned adjacent to and surrounding the perimeter of the nasal-proximal aperture of the adapter channel, and is suitable to provide for a supplementary air curtain substantially adjacent to and surrounding the dispersed flow of delivered nebulized particles. Preferably, the nebulized particles are delivered in a vortical flow, and upon supplemental inhalation, the air curtain provides sufficient convective draft to stretch and increase the vorticity of the vortical flow.

Nebulized particles (and nebulizing fluid and supplemental air) travel through the nebulizer chamber and exit through a top opening 3 into a particle dispersion chamber, which is in direct communication with the top opening of the nebulizer chamber 3. In this instance, the particle dispersion chamber is formed from an outer annular member 2 and an inner annular member 1. The inner annular member 1, equipped with a pair of o-rings, is insertable into the outer annular member 2 to form an internal chamber that is sealed at each end by the o-rings, which are compressed between the outer 2 and inner 1 annular members. The outer annular member 2 comprises a opening for entry of compressed fluid into the internal chamber. The wall of inner annular member 1 comprises one or more integral fluid output channels for channeling compressed fluid from the internal chamber (formed between the inner 1 and outer 2 annul members) to the interior of the particle dispersion chamber. The integral fluid output channels are directionally oriented so that compressed fluid exiting therefrom passes tangentially, and at an upward angle $\theta$ (see FIG. 42) of between about 30 and about 75 degrees, into the particle dispersion chamber to provide for vortical flow of the nebulized medicament particles traveling through and exiting from the particle dispersion chamber. Preferably, the angle $\theta$ is about 30 to about 60 degrees. Preferably, the angle $\theta$ is about 45 degrees.

In the instant embodiment, compressed fluid travels from the compressor channel 9 to the particle dispersion chamber by means of a dispersion feed channel 19. In the instant embodiment, the dispersion feed channel lies outside the nebulizer chamber and the particle dispersion chamber. Alternatively, the dispersion feed channel may be integrated in to the wall of the nebulizer chamber, or may travel within the nebulizer chamber to eventually feed the integral fluid output channels of the particle dispersion chamber.

An optional 'check valve', comprising upper and lower retaining members 4 and 6, along with a check valve disc 5 is shown located within the nebulizer chamber, and positioned between the impacter and the lower opening of the particle dispersion chamber. The check valve serves to prevent particles from exiting the supplementary air intake opening 18 of upper portion 3 of the nebulization chamber.

Factors affecting nebulization rate, and particle size. According to the present invention, the rate of nebulization is affected, inter alia, by both the angle θ (see FIG. 42), and the compressed fluid flow. According to the present invention, the particle size is affected, inter alia, by the hydrodynamic properties of the medicament solution, the fluid flow, and the geometry of the impacter 7. Therefore, according to the present invention, these variables of the inventive integrated nebulizer and particle dispersion chamber can be adapted by one of ordinary skill in the art to provide particles having the preferred mean diameter range, and that can be delivered at an optimal rate and dosage.

Dual particle dispersion chambers and complementary nasal adaptor. The nasal anatomy is structured so that particles entering one side or the other will have a better propensity to penetrate space and impact on tissue if they are in a vortex spinning in a particular direction. This spin is imparted on the droplets (particles) using the inventive controlled particle dispersion technology disclosed herein.

In particularly preferred embodiments (see FIGS. 53 and 54) the inventive nebulizer is in direct communication with a pair of particle dispersion chambers (or with a pair of particle dispersion channels within one particle dispersion chamber) disoriented to provide direct parallel (or substantially parallel) delivery of vortical flow particles into each nostril via a complementary bifurcated nasal adapter. According to the present invention, such dual delivery significantly eliminates any medicament loss resulting from particle collisions with the center of the nose between the two separate nasal passages. Additionally, dual particle dispersion channels allow for setting different vortical parameters (e.g., angle, velocity, direction, etc.) for each particle dispersion channel, and further allows for vortical flows having opposite directions (a preferred aspect). The inventive dual design allows for a vortical flow to be targeted to each nostril, and the vortical flow is not interrupted by flow colliding with the division between the nostrils. Thus, in preferred embodiments, the dispersion parameters can be optionally and uniquely tailored to individual users if necessary or desired (e.g., for long-term users treating chronic conditions, or where one nostril if relatively obstructed or otherwise distinguishable from the other.

In the context of the present preferred implementations, there are two most preferred vortex motions, as seen in FIG. 54. The preferred dual vortical flow patterns of FIG. 54 are illustrated from a top view of the nasal-proximal ends of the nasal adapter or particle dispersion channels. Type I delivery (left vortex clockwise, right vortex counterclockwise) is typically used for topical application wherein droplets (nebulized particles) need to access under the turbinates in the nasal cavity. Type II delivery (left vortex counterclockwise, right vortex clockwise) is typically used for penetration high in the nasal cavity to reach the olfactory region. Type I or Type II delivery is affected in the present implementations by repositioning the dispersion channel components of the device by 180 degrees.

Particle sizes. According to preferred aspects of the present invention, the nasally delivered nebulized particles are comprised of particles substantially having a mean diameter of about 2 to about 50 µm, about 5 to about 50 µm, about 5 to about 40 µm, about 5 to about 35 µm, about 5 to about 30 µm, about 5 to about 20 µm, about 5 to about 17 µm, about 5 to about 15 µm, about 8 to about 30 µm, about 8 to about 20 µm, about 10 to about 30 µm, about 10 to about 25 µm, about 10 to about 20 µm, about 10 to about 17 µm, about 10 to about 15 µm, about 11 to about 40 µm, about 11 to about 30 µm, about 11 to about 20 µm, about 11 to about 15 µm, about 12 to about 17 µm, about 15 to about 25 µm, about 15 to about 20 µm, and about 17 to about 23 µm.

Preferably, the nasally delivered nebulized particles are comprised of particles substantially having a mean diameter of about 5 to about 30 the delivered nebulized particles are comprises of particles substantially having a mean diameter of about 5 to about 30 µm, about 10 to about 20 µm, about 10 to about 17 µm, about 10 to about 15 µm, and about 12 to about 17 µm.

Preferably, the nasally delivered nebulized particles are comprised of particles substantially having a mean diameter of about 10 to about 15 µm, or about 12 to about 15 µm.

The phrase "substantially having a mean diameter," as used herein with respect to preferred particle diameter ranges, refers to the use of particle collections, wherein at least 50%, at least 60%, at least 70%, at least 80%, at least 90%, or at least 95% have the preferred diameter range. Preferably, at least 60%, 70%, 80%, 90% or 95% of the nebulized particles are of the preferred particle diameter range. More preferably, at least 70%, 80%, 90% or 95% of the nebulized particles are of the preferred particle diameter range.

Preferred Linear Nebulization Embodiments

In addition to art-recognized 'jet' nebulizers, linear or direct nebulizers are known. Particularly preferred embodiments of the present invention comprise linear nebulization.

Figure 45:
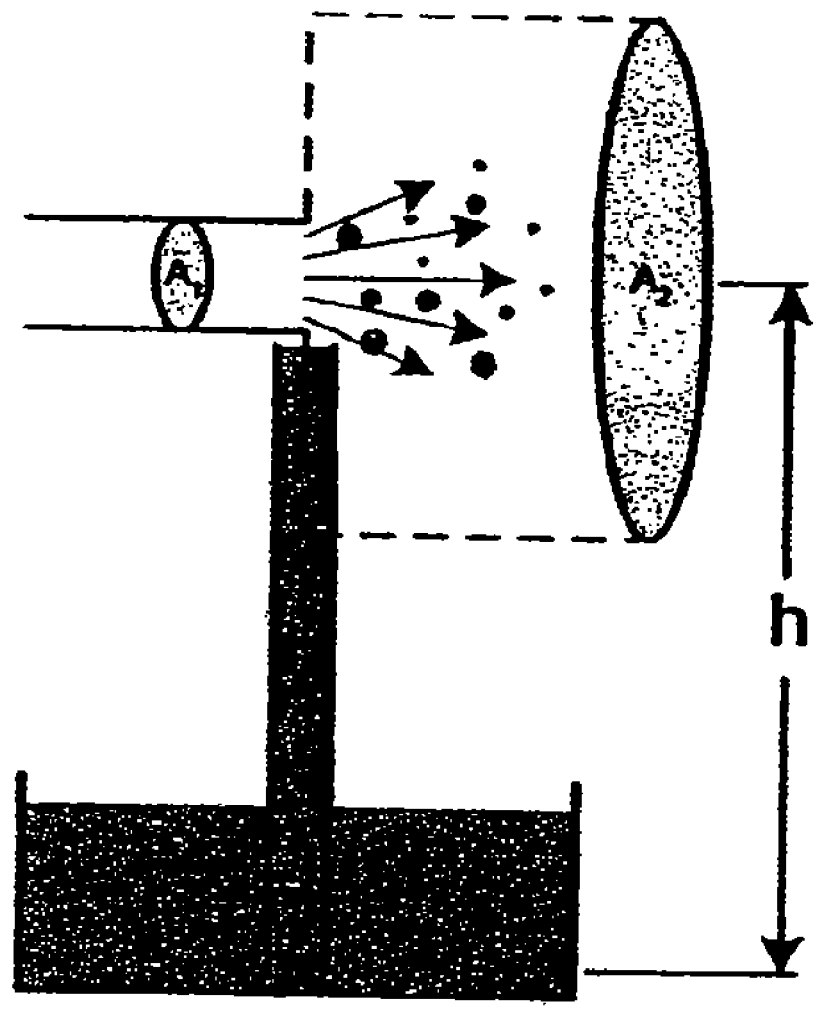
FIG. 45 shows the basic principals of direct (e.g., linear) nebulization using a nebulizer model with a vertical liquid column and air flowing through a horizontal conduit from left to right. The principals summarized are applicable to various direct or linear nebulizer designs, including particular embodiments of the inventive integrated nebulizer and particle dispersion chamber embodiments disclosed herein

Principles of linear nebulization. The basic principals of linear nebulization are discussed here with reference to FIG. 45, which shows, for simplicity of illustration, a nebulizer model with a liquid column and air flowing through a conduit from left to right. The principals summarized here are, nonetheless applicable to various nebulizer designs, including those of the inventive nebulizer embodiments herein).

When a fluid in a pipe or conduit encounters a sudden enlargement in cross-sectional area, 'head loss' ($H_L$) occurs. The momentum equation combines with Bernoulli's equation about the control volume $$P_1/\rho + V_1^2/2g_c = P_2/\rho + V_2^2/2g_c + H_L g/g_c \quad \text{(equation 1)}$$

The momentum equation equates the net force to the rate of change of momentum:

$$P_1 A_2 - P_2 A_2 = (V_2) V_2 A_2 \rho/g_c - (V_1) V_1 A_1 \rho/g_c \quad \text{(equation 2)}$$

The salient term in equation 2 is $P_1 A_2$. While it might appear that the force acting to the right (in the direction of the air stream) in the model of FIG. 45 should be $P_1 A_1 + P_2(A_2 - A_1)$, the low pressure prevails immediately after the expansion, because of the separated flow at the abrupt enlargement of cross-sectional area. This separation causes the head loss in the sudden expansion. Equating $P_2 - P_1$ from equations 1 and 2:

$$P_2 - P_1 = (V_1^2 - V_2^2)\rho/2g_c - H_L(g\rho/g_c) = (V_1 V_2 - V_2^2)\rho/g_c$$

Solving for head loss ($H_L$):

$$H_L = (1/2g)(V_1 - V_2)^2 = (V_1^2/2g)(1 - (A_1/A_2))^2$$

Furthermore, where $A_2 \ggg A_1$, $A_1/A_2$ approaches zero, such that:

$$H_L = V_1^2/2g$$

The pressure drop at the point of enlargement (inches of water) needs to be greater than the column of fluid (h). This will bring the liquid up the column and into the air stream.

The pressure generated by the water column is ρgh. This is the force the pressure, generated by the air flow, has to overcome.

Figure 49:
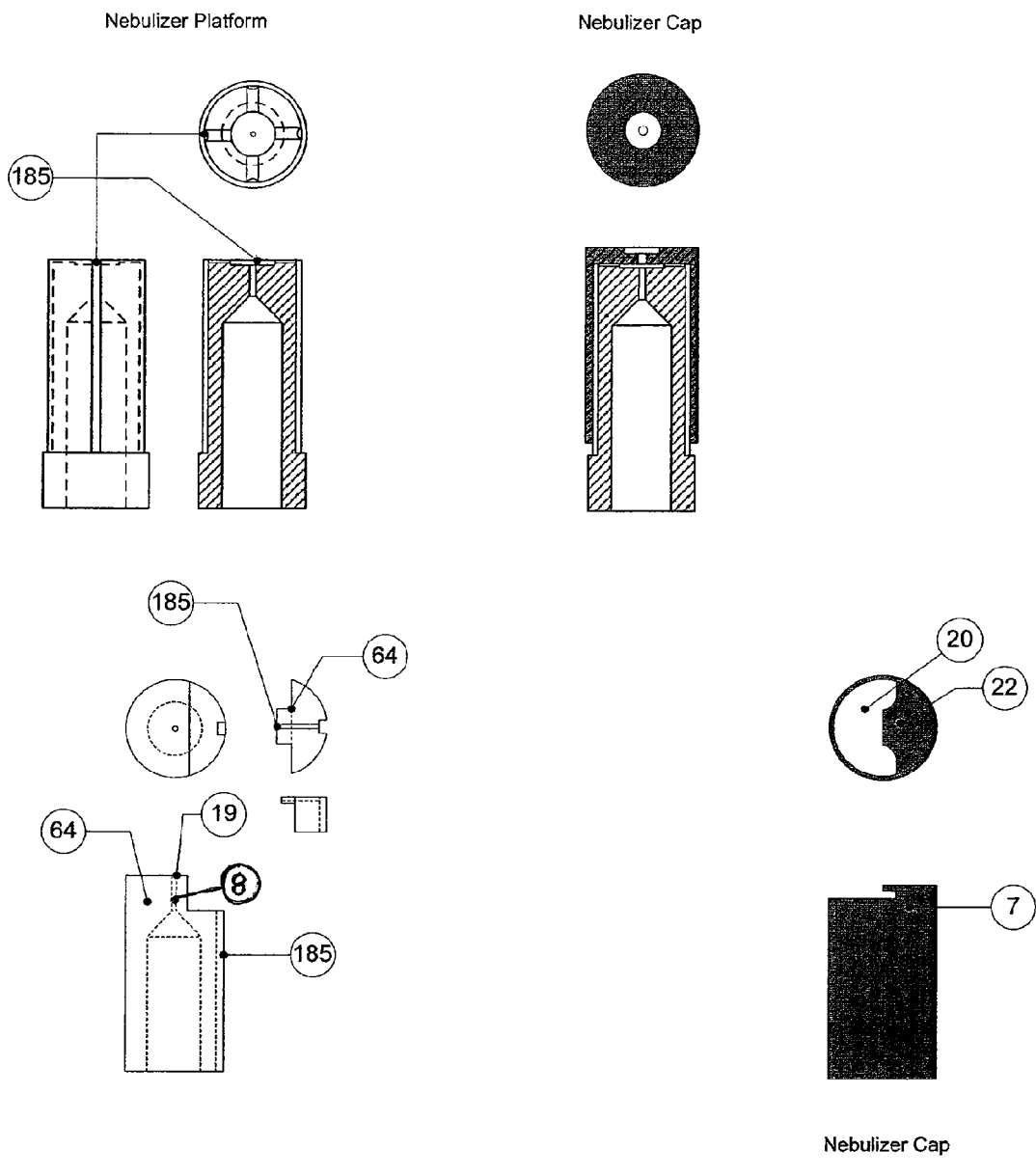
Figure 50:
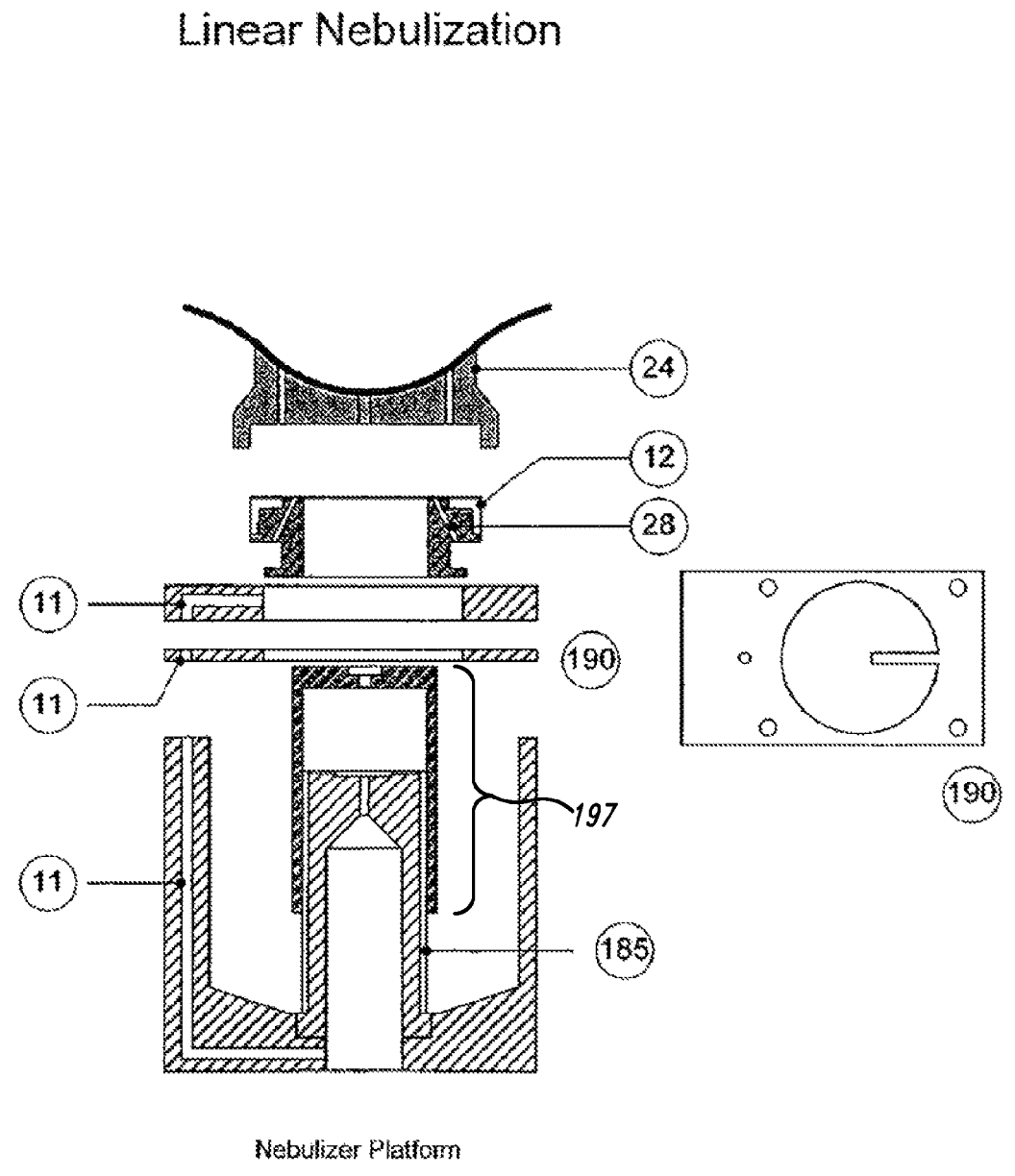

Preferred linear nebulization embodiment. A particularly preferred embodiment of the present invention is shown in FIGS. 49, and 50. Preferably, the device is constructed of medical grade polycarbonate or acrylic material, although other art-recognized materials will suffice. As describe above for jet nebulizer embodiments, the exemplary device comprises a housing, for example, having two halves held together, for example, by screws, pins, or the like. Alternatively, the housing could be sealed, snapped or otherwise held together. The unit may comprise one or more activatable (e.g., switch) battery-powered compressor pumps (fluid pumps), accommodated within the lower region of the housing, and my further comprise an external power source. Alternatively, compressed air cartridges may be used in place of batteries, or in place of batteries and compressors. In alternate embodiments there is a single battery-powered compressor pump, and a receiving compartment for a medicament cartridge (e.g. UDV).

Compressed fluid (e.g., air, gas, or combinations thereof) is directed from a compressor pump, via compressor channels, toward the pressure release channel 8 of the nebulizing pressure release member 64 projecting into the nebulizer chamber of the nebulizer. The compressed fluid is directed up through the pressure release channel 8 and member 64 to a pressure release orifice 19 located substantially at the center of the top surface of the pressure release member 64. A nebulization cap 7 fits over and substantially conforms to the surface (e.g., cylindrical surface) of the pressure release member 64. The nebulization cap 7 has a top opening 20 in communication with the pressure release orifice 19 to allow compressed fluid to travel from the pressure release orifice 19 through the top opening 20 of the nebulization cap 7. The nebulization cap 7 additionally comprises an obstructing member 22 that partially overlaps a position directly above the pressure release orifice 19, and thereby partially obstructs the path of emerging fluid from the pressure release orifice 19. The nebulizing pressure release member 64 further comprises a medicament channel 185 (see e.g., the analogous impacter channel 185 of FIGS. 30 and 33) that is recessed into the outer wall of the pressure release member 64, such that the pressure release channel 185 runs adjacent to the internal surface of the nebulization cap 7 (that is, when it is in place on the pressure release member 64), and further is in communication with the lower concave or receptacle-like bottom of the nebulizing chamber, and the pressure release orifice 19. During operation of the nebulizer, liquid medicament is drawn (by virtue of the flow of compressed fluid through the pressure release orifice 19 and nebulization cap opening 20) from the base of the nebulizing chamber up through the medicament channel 185, and to the end of the obstructing member 22, to the pressure release orifice 19, whereupon the liquid is nebulized into droplets directed into the nebulizer chamber. A keeper-plate 190 (or equivalent keeper member) is positioned above the nebulization cap 7 to hold the nebulization cap in position during operation of the nebulizer. As for other embodiments described herein, in addition to the nebulizing fluid entering the nebulization chamber from the pressure release member 64, supplemental air required by a breathing user enters the nebulization chamber through an appropriate opening of the nebulization chamber. In some embodiments, the supplemental air thus enters the nebulizing chamber and combines with the nebulizing fluid (e.g., air, gas) and nebulized particles.

Preferred embodiments comprise a supplementary inhalation channel integral to or in direct communication with the nasal adapter, the inhalation channel at one end in communication with ambient air, and the other end being positioned adjacent to and in communication with the perimeter of the nasal-proximal aperture of the adapter channel. Preferably, the nasal-proximal end of the inhalation channel is annular, positioned adjacent to and surrounding the perimeter of the nasal-proximal aperture of the adapter channel, and is suitable to provide for a supplementary air curtain substantially adjacent to and surrounding the dispersed flow of delivered nebulized particles. Preferably, the nebulized particles are delivered in a vortical flow, and upon supplemental inhalation, the air curtain provides sufficient convective draft to stretch and increase the voracity of the vortical flow.

Nebulized particles (and nebulizing fluid and supplemental air) travel through the nebulizer chamber and exit through a top opening into a particle dispersion chamber 12, which is in direct communication with the top opening of the nebulizer chamber. In this instance, the particle dispersion chamber 12 is formed, at least in part, from an outer annular member 2 and an inner annular member 1. The inner annular member 1, equipped with a pair of o-rings, is insertable into the outer annular member 2 to form an internal chamber 9 that is sealed at each end by the o-rings, which are compressed between the outer 2 and inner 1 annular members. The outer annular member 2 comprises an opening for entry of compressed fluid (e.g., bled from a compressor channel of the unit) into the internal chamber 9. The wall of inner annular member 1 comprises one or more integral fluid output channels 28 for channeling compressed fluid from the internal chamber 9 (formed between the inner 1 and outer 2 annul members) to the interior of the particle dispersion chamber. The integral fluid output channels are directionally oriented so that compressed fluid exiting therefrom passes tangentially, and at an upward angle θ (see FIG. 42) of between about 30 and about 75 degrees, into the particle dispersion chamber to provide for vortical flow of the nebulized medicament particles traveling through and exiting from the particle dispersion chamber. Preferably, the angle θ is about 30 to about 60 degrees. Preferably, the angle θ is about 45 degrees.

In the instant embodiment, compressed fluid travels from the compressor channel 10 to the particle dispersion chamber by means of a dispersion feed channel 11. The dispersion feed channel 11 may lie outside the nebulizer chamber and the particle dispersion chamber. Alternatively, the dispersion feed channel may be integrated into the wall of the nebulizer chamber, or may travel within the nebulizer chamber to eventually feed the integral fluid output channels of the particle dispersion chamber.

An optional 'check valve', as described above with respect to preferred jet nebulization embodiments, serves to prevent particles from exiting the supplementary air intake opening of the nebulization chamber.

Figure 53:
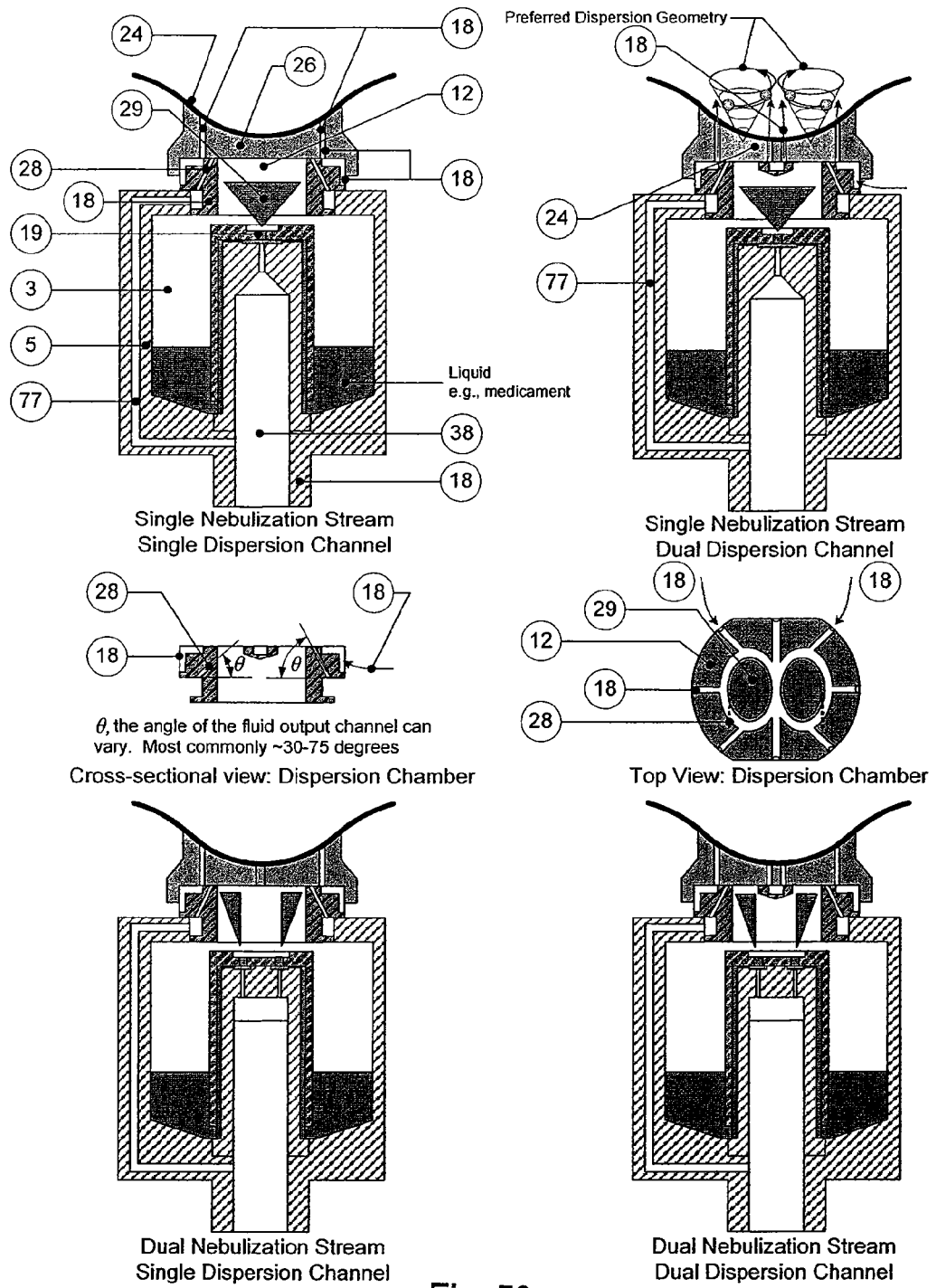
FIG. 53 shows particularly preferred representative embodiments of the inventive integrated nebulizer. Both single and double nebulization stream variations are shown a long with both single and dual particle dispersion channel variants.

Referring to FIG. 53, particularly preferred aspects of the present invention provide a nebulizer suitable for topical drug delivery to, or systemic drug delivery via, a deep nasal cavity or paranasal sinus, comprising: a nasal adapter 24 having nasal proximal and nasal distal ends, and having at least one adapter channel 26 communicating between an aperture in the nasal-proximal end and an aperture in the nasal-distal end; a particle dispersion chamber 12, integral or in direct communication with the nasal adapter 24, and comprising: a dispersion chamber wall 7 having an external and an internal surface, the internal surface defining at least one internal dispersion channel, the internal dispersion channel comprising the nasal adapter channel 26; and a compressed fluid output channel 28 in communication with the internal dispersion channel; a nebulizing chamber, integral or in direct communication with the particle dispersion chamber 3, and comprising: a nebulizing chamber wall 5; and nebulizing means with at least one pressure release orifice 19 suitable to produce a nebulized particle stream 29; a nebulizing pressure feed 37 having a compressor channel 38 in communication with the pressure release orifice 19 of the nebulizing chamber 3; and a dispersion feed channel 77 communicating between the nebulizing pressure feed 37 and the fluid output channel 28 of the particle dispersion chamber, the nebulizer suitable to deliver a dispersed flow of nebulized particles to a nasal orifice.

Preferably, the compressed fluid output channel 28 is integral with the dispersion chamber wall 7. Preferably, the compressed fluid output channel 28 communicates with the nasal adaptor portion 26 of the internal dispersion channel. Preferably, there is a plurality of compressed fluid output channels in communication with at least one dispersion feed channel. Preferably, the dispersion feed channel 77 is integral with at least one of the nebulization chamber wall 5 and the dispersion chamber wall 7. Preferably, dispersed particle flow of nebulized particles comprises vortical particle flow thereof. Preferably, the nebulizer comprises: a single nebulizer pressure release orifice; and dual internal dispersion channels comprising corresponding dual nasal adapter channels. Alternately, the nebulizer comprises: dual nebulizer pressure release orifices; and dual internal dispersion channels comprising corresponding dual nasal adapter channels. Preferably, the dispersion chamber is suitable to provide for independent vortical flow patterns within and from each of the dual internal dispersion channels. Preferably, the dispersion chamber is suitable to provide for dual vortical flow patterns that spiral in opposite directions. Preferably, the nebulizer comprises at least one of jet nebulization means 196 and linear nebulization means 197. Preferably, the nebulizer comprises linear nebulization means 197.

Preferably, the nebulizer further comprises a supplementary inhalation channel 18 integral to or in direct communication with the nasal adapter 24, the channel at one end in communication with ambient air, the other end 18 being positioned adjacent to and in communication with the perimeter of the nasal-proximal aperture of the adapter channel. Preferably, the nasal-proximal end 19 of the inhalation channel is annular, positioned adjacent to and surrounding the perimeter of the nasal-proximal aperture of the adapter channel, and is suitable to provide for a supplementary air curtain substantially adjacent to and surrounding the dispersed flow of delivered nebulized particles. Preferably, the nebulized particles are delivered in a vortical flow, and wherein, upon supplemental inhalation, the air curtain provides sufficient convective draft to stretch and increase the vorticity of the vortical flow.

Alternately, the nebulizer further comprises a supplementary inhalation channel integral to or in direct communication with the nasal adapter, the channel at one end in communication with ambient air, the other end being annularly positioned at the nasal distal end of the adapter channel to direct supplementary air flow in an annual curtain adjacent to the internal wall of the adapter channel.

According to the present invention, and as shown in the left central panel of FIG. 53, the angle between the fluid output channel and a cross-sectional plane of the particle dispersion channel is Preferably, the substantial mean diameter of the particle size is selected from the group consisting of about 2 to about 50 µm, about 5 to about 50 µm, about 5 to about 40 µm, about 5 to about 35 µm, about 5 to about 30 µm, about 5 to about 20 µm, about 5 to about 17 µm, about 5 to about 15 µm, about 8 to about 30 µm, about 8 to about 25 µm, about 8 to about 20 µm, about 10 to about 30 µm, about 10 to about 25 µm, about 10 to about 20 µm, about 10 to about 17 µm, about 10 to about 15 µm, about 11 to about 40 µm, about 11 to about 30 µm, about 11 to about 20 µm, about 11 to about 15 µm, about 12 to about 17 µm, about 15 to about 25 µm, about 15 to about 20 µm, and about 17 to about 23 µm. More preferably, the substantial mean diameter of the particle size is selected from the group consisting of about 5 to about 30 µm, about 8 to about 25 µm, about 10 to about 20 µm, about 10 to about 17 µm, about 10 to about 15 µm, and about 12 to about 17 µm. Even more preferably, the substantial mean diameter of the particle size is selected from the group consisting of about 8 to about 25 µm, about 10 to about 15 µm, or about 12 to about 15 µm. Most preferably, the substantial mean diameter of the particle size is about 8 to about 25 µm.

Preferably, the nebulizer further comprises: a medicament cartridge receiving portion 107 in communication with the nebulizing means 196/197; and a medicament cartridge 103 functionally complementary to the cartridge receiving portion 107.

Factors affecting nebulization rate, and particle size. According to the present invention, the rate of nebulization is affected, inter alia, by both the angle θ, and the compressed fluid flow. According to the present invention, the particle size is affected, inter alia, by the hydrodynamic properties of the medicament solution, the fluid flow, and the geometry (e.g., degree of overlap with, and distance above the pressure release orifice 19) of the nebulization cap relative to the pressure release member and orifice 19. Therefore, according to the present invention, these variables of the inventive integrated nebulizer and particle dispersion chamber can be adapted by one of ordinary skill in the art to provide particles having the preferred mean diameter range, and that can be delivered at an optimal rate and dosage.

Dual particle dispersion chambers and complementary nasal adaptor. In particularly preferred embodiments the inventive nebulizer is in direct communication with a pair of particle dispersion chambers oriented to provide direct parallel delivery of vortical flow particles into each nostril via a complementary bifurcated nasal adapter (see, e.g., the right panels of FIG. 53). According to the present invention, such parallel delivery significantly eliminates any medicament loss resulting from particle collisions with the center of the nose between the two separate nasal passages. Additionally, dual particle dispersion chambers allow for setting different vortical parameters for each particle dispersion chamber, and further allows for vortical flows having opposite directions (see, e.g., FIG. 54). This design allows a vortical flow targeted at each nostril, and the vortical flow is not interrupted by excessive particle collisions with the division between the nostrils. Thus, the dispersion parameters can be uniquely tailored to individual users is necessary or desired (e.g., for long-term users treating chronic conditions, or where one nostril if relatively obstructed or otherwise distinguishable from the other.

According to preferred aspects of the present invention, the nasally delivered nebulized particles are comprised of particles substantially having a mean diameter of about 2 to about 50 µm, about 5 to about 50 µm, about 5 to about 40 µm, about 5 to about 35 µm, about 5 to about 30 µm, about 5 to about 20 µm, about 5 to about 17 µm, about 5 to about 15 µm, about 8 to about 30 μm, about 8 to about 20 μm, about 10 to about 30 μm, about 10 to about 25 μm, about 10 to about 20 μm, about 10 to about 17 μm, about 10 to about 15 μm, about 11 to about 40 μm, about 11 to about 30 μm, about 11 to about 20 μm, about 11 to about 15 μm, about 12 to about 17 μm, about 15 to about 25 μm, about 15 to about 20 μm, and about 17 to about 23 μm.

Preferably, the nasally delivered nebulized particles are comprised of particles substantially having a mean diameter of about 5 to about 30 the delivered nebulized particles are comprises of particles substantially having a mean diameter of about 5 to about 30 μm, about 10 to about 20 μm, about 10 to about 17 μm, about 10 to about 15 μm, and about 12 to about 17 μm.

Preferably, the nasally delivered nebulized particles are comprised of particles substantially having a mean diameter of about 10 to about 15 μm, or about 12 to about 15 μm.

The phrase "substantially having a mean diameter," as used herein with respect to preferred particle diameter ranges, refers to the use of particle collections, wherein at least 50%, at least 60%, at least 70%, at least 80%, at least 90%, or at least 95% have the preferred diameter range. Preferably, at least 60%, 70%, 80%, 90% or 95% of the nebulized particles are of the preferred particle diameter range. More preferably, at least 70%, 80%, 90% or 95% of the nebulized particles are of the preferred particle diameter range.

Novel Use of Preferred Particles.

In consideration of the above disclosure, therefore, preferred embodiments of the present invention provide novel use, for topical drug delivery to, or systemic drug delivery via, a deep nasal cavity or paranasal sinus, of an aerosol comprised of substantially uniform diameter aerosolized particles.

Preferred embodiments thus provide a method of drug delivery to a deep nasal cavity or paranasal sinus, comprising: producing nebulized particles substantially having a uniform mean diameter.

Preferably, the aerosolized particles pass through a particle dispersion chamber prior to delivery.

Preferably, the particle dispersion chamber is suitable to provide for vortical particle flow from at least one particle dispersion channel. Preferably, a dual dispersion channel is used to provide for dual vortical particle flows. Preferably, the dual vertical particle flows are in opposite directions (see, e.g., Type I and Type II flow patterns illustrated in FIG. 54).

Preferably, the particles are comprised of particles substantially having a mean diameter of about 2 to about 50 μm, about 5 to about 50 μm, about 5 to about 40 μm, about 5 to about 35 μm, about 5 to about 30 μm, about 5 to about 20 μm, about 5 to about 17 μm, about 5 to about 15 μm, about 8 to about 30 μm, about 8 to about 25 μm, about 8 to about 20 μm, about 10 to about 30 μm, about 10 to about 25 μm, about 10 to about 20 μm, about 10 to about 17 μm, about 10 to about 15 μm, about 11 to about 40 μm, about 11 to about 30 μm, about 11 to about 20 μm, about 11 to about 15 μm, about 12 to about 17 μm, about 15 to about 25 μm, about 15 to about 20 μm, and about 17 to about 23 μm.

Preferably, the delivered nebulized particles are comprised of particles substantially having a mean diameter of about 5 to about 30 μm, about 8 to about 25 μm, about 10 to about 20 μm, about 10 to about 17 μm, about 10 to about 15 μm, and about 12 to about 17 μm.

Preferably, the particles are comprised of particles substantially having a mean diameter of about 8 to about 25 μm, 10 to about 15 μm, or about 12 to about 15 μm.

Preferably, at least 50%, at least 60%, at least 70%, at least 80%, at least 90%, or at least 95% have the preferred diameter range. Preferably, at least 60%, 70%, 80%, 90% or 95% of the nebulized particles are of the preferred particle diameter range. Preferably, at least 70%, 80%, 90% or 95% of the nebulized particles are of the preferred particle diameter range.

Preferred embodiments thus provide a method of drug delivery to a deep nasal cavity or paranasal sinus, comprising: producing nebulized particles substantially having a uniform mean diameter selected from the group consisting of about 5 to about 30 μm, about 8 to about 25 μm, about 10 to about 20 μm, about 10 to about 17 μm, about 10 to about 15 μm, and about 12 to about 17 μm; and passing the nebulized particles, prior to delivery, through a particle dispersion chamber suitable to provide for vortical particle flow. Preferably, the nebulized particles substantially have a uniform mean diameter of about 8 to about 25 μm. Preferably, at least 60%, at least 70%, at least 80%, at least 90% or at least 95% of the nebulized particles are of the preferred particle diameter range. More preferably, at least 70%, at least 80%, at least 90% or at least 95% of the nebulized particles are of the preferred particle diameter range. Most preferably, the integrated inventive nebulizers described herein are used for this purpose.

Complementary Cartridge Docking System: Drug Delivery Specificity, Based on Cartridge-Specific and Drug-Specific Docking with the Inventive Integrated Nebulizer Device Referring to FIGS. 51 and 52, additional preferred embodiments provide a complementary cartridge docking system (CCDS) that allows for drug-delivery specificity with respect to a given user and device. In preferred embodiments, the inventive CCDS system comprises an integrated nebulizer and particle dispersion chamber device according to the present invention, in combination with one of a plurality of distinctive adapter cartridge types receivable into a base nebulizer, and a medicament ampoule functionally complementary to one of the adapter cartridge types. This inventive system thus provides for cartridge-specific docking by the medicament ampoule, and user-specific drug delivery, where the user is provided with a base nebulizer, a specific adapter cartridge, and a corresponding functionally complementary medicament cartridge.

According to preferred aspects, specific drugs are restricted to specific ampoule designs to provide for drug-specific docking with the adapter cartridge portion of the integrated nebulizer and particle dispersion chamber device. Preferably, each drug (or drug provider) is paired with a unique ampoule (e.g., UDV; unit dose vial) shape and/or configuration, such that only that assigned ampoule (and therefore, that matched drug) can be used in a respective functionally complementary version (e.g., branded version) of the inventive integrated nebulizer and particle dispersion chamber device. Functional complementarity between the adapter cartridge and the ampoule design is the key to this system. The medicament ampoule design is not only matched (assigned to) a particular drug, but specific ampoule designs will only work with the respective functionally complementary version of the adapter cartridge of the integrated nebulizer and particle dispersion chamber device (i.e., will only work with those having a complementary adapter cartridge).

The inventive CCDS system can be appreciated as a docking station concept, under which a specifically designed UDV would be docked to a respective functionally complementary integrated nebulizer/particle dispersion chamber. Drug delivery is user-specific where a particular drug and unique UDV are, for example, prescribed by a physician to a given user.

Figure 51:
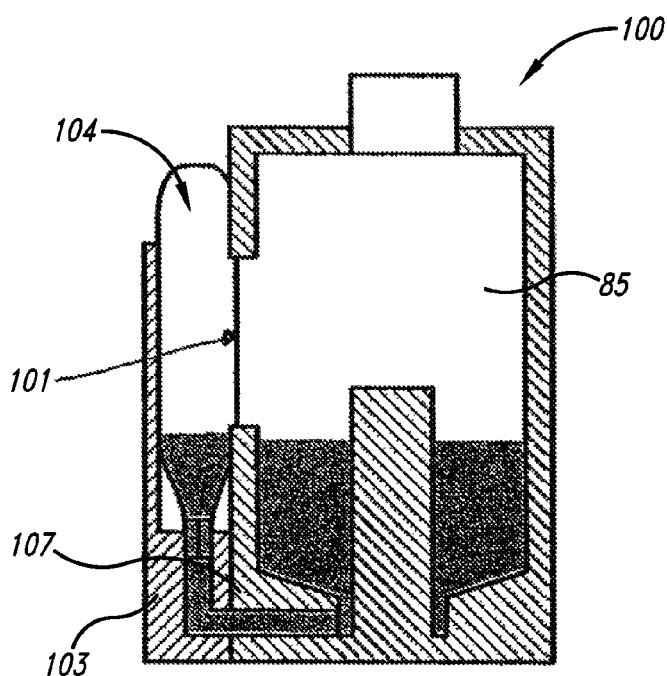
FIG. 51 shows an exemplary embodiment of the inventive complimentary cartridge docking system (CCDS), wherein a sidewall of a functionally complementary medicament cartridge (e.g., UDV; unit dose vial) forms an interior boundary of the nebulizer chamber. Without the complementary UDV, the integrated nebulizer device will not function properly.

FIG. 51 shows one embodiment of the inventive CCDS system, wherein a sidewall 101 of a complementary medicament ampoule (e.g., UDV) 104 forms an interior boundary of the nebulizer chamber 85 when it is mounted in the complementary adapter cartridge 103 of the inventive nebulizer 100. Therefore, the shape and/or functionality of a given adapter cartridge type is specifically complementary to the shape of the UDV (e.g., drug/UDV prescribed to a specific user), and/or the fill port within the adapter cartridge 103 is specific to the nozzle of the UDV. Additionally, and preferably, not only will insertion of the ampoule 104 into the adapter cartridge 103 depend on complementarity, but without the complementary UDV, the integrated nebulizer device will not function properly regardless of insertability.

Figure 52:
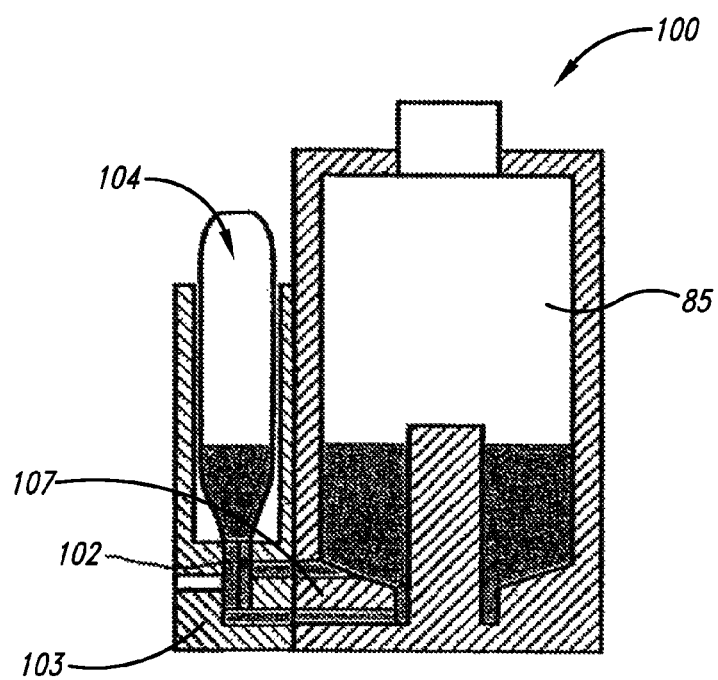
FIG. 52 shows another exemplary CCDS embodiment, wherein a complementary UDV nozzle blocks a drainage port of a nebulizer chamber. Without the functionally complementary UDV in place (i.e., in the absence of complementary docking), medicament non-productively drains from the device.

FIG. 52 shows another embodiment of the inventive CCDS system, wherein a complementary UDV nozzle 102 blocks a drainage port of a nebulizer chamber. Without the complementary UDV in place (i.e., in the absence of complementary docking), medicament solution would non-productively drain from the device. Preferably, the volume aspects of the device and medicament solution channels are designed such that if the drainage port is illicitly blocked (e.g., by someone attempting to use an illegitimate cartridge) by another non-complementary means, the liquid-holding volume of the device would not be sufficient to hold an entire dosing and the device would not work, because the liquid dose level would be high enough to cover the nebulizer jet and thereby preclude functionality. Preferably, as in the above embodiment, the shape of the adapter cartridge of the integrated nebulizer device is complementary with, and specific to the shape of the UDV, and/or the fill port within the adapter cartridge is specific to the nozzle of the UDV.

Accordingly, a variety of medicament cartridge shapes and configurations, as well as functional safeguards, are encompassed within the scope of the present invention, where in essence, the design of the ampoule must be insertibly complementary, and preferably also functionally complementary, with the adapter cartridge of the integrated nebulizer and particle dispersion chamber device. According to preferred aspects, complementarity is provided at the level of selective ampoule insertion/docking (e.g., by complementary ampoule body shape, or nozzle design), and/or at the level of nebulizer function after ampoule insertion. Thus, the inventive medicament ampoules could be of many shapes, sizes and designs, provided that insertional and functional complementarity exists between a specific medicament ampoule and a respective complementary adapter cartridge of the inventive integrated nebulizer and particle dispersion chamber device.

Preferably, a ampoule-specific adapter cartridge is provided to a user, along with the respective medicament ampoule (e.g., drug/UDV and adapter prescribed to a specific user). Ampoule design could take a variety of forms. For example, the ampoule could be complementary with a unique nozzle design/configuration of a particular adapter cartridge. Alternatively, the ampoule could be designed to preclude insertion into non-complementary shaped adapter cartridges.

Preferred embodiments provide a method for user-specific nebulized drug delivery using medicament ampoules, comprising: identifying an intended user of a desired nebulizable medicament; providing, to the user, a base nebulizer having an adapter cartridge receiving portion, wherein any one of a plurality of adapter cartridge types is receivable by the receiving portion, wherein each adapter cartridge type is designed to be functionally complementary to a corresponding distinctive medicament ampoule design, and wherein each medicament ampoule of a particular distinctive ampoule design comprises a particular nebulizable medicament or dosage thereof assigned to that design; and providing to the user an adapter cartridge type corresponding to the desired medicament, whereby user-specific nebulized drug delivery is afforded.

Preferably, nebulization is according to claim 21. Preferably, where the intended use is of a plurality of particular medicaments, the user is provided with a corresponding plurality of adapter cartridges. Preferably, functionally complementary between the adapter cartridge and the medicament ampoule is based, at least in part, on the external surface or shape of the medicament ampoule. Alternatively, functional complementarity is based on functional design of an otherwise receivable medicament ampoule.

The present invention is further illustrated by reference to the EXAMPLES below. However, it should be noted that these EXAMPLES, like the embodiments described above, are illustrative and are not to be construed as restricting the enabled scope of the invention in any way.

EXAMPLE I

The Inventive Integrated Nebulizer and Particle Dispersion Apparatus was Used to Target the Deep Nasal Sinuses (Paranasal Sinuses)

A 21-year-old female subject was provided with the nebulizer 25 and was instructed to perform the Controlled Particle Dispersion Breathing Technique (BT). A TC-DTPA aerosol radiopharmaceutical was provided in the nebulizer 25 in a dose of 10 mci. After performance of the BT, a technesium imaging test was performed on the nasal sinuses of the subject. The technesium imaging test was performed at Swedish Medical Center in Seattle, Wash. The technesium imaging test allows for identification of nebulized particles in the ethmoid and sphenoid sinuses. The findings of the technesium imaging tests were of tracer activity in the ethmoid and sphenoid sinuses bilaterally. There was no activity in the maxillary or frontal sinuses. Communication between the nasal airway and ethmoidal and sphenoid sinuses was documented.

EXAMPLE II

Using the Inventive Integrated Nebulizer and Particle Dispersion Chamber Apparatus, Aerosol, Delivered Via a Nasal Mask, Communicated with the Ethmoid and Sphenoid Sinuses Bilaterally but Not with the Frontal Sinuses A 25-year-old male subject was provided with the nebulizer 25 and instructed to perform the Controlled Particle Dispersion Breathing Technique (BT). The nebulizer 25 was provided with TC-DTPA aerosol at a dose of 15 mci. The technesium imaging test was performed at Swedish Medical Center in Seattle, Wash. The technesium imaging test allows for identification of nebulized particles in the ethmoid and sphenoid sinuses. The findings of the technesium imaging study were that proton activity was greater in the ethmoid, maxillary and sphenoid sinuses bilaterally greater right than left. There was no tracer activity in the frontal sinuses. The aerosol was delivered via a nasal mask communicated with the ethmoid and sphenoid sinuses bilaterally but not with the frontal sinuses.

A representative sinus-bent image for the subjects in Examples 1 and 2 is provided in FIG. 22. FIG. 22 shows delivery to the ethmoid, maxillary and sphenoid sinuses via the nebulizer 25. Prior art FIG. 21 shows no penetration into any of the paranasal sinuses and far less penetration of the nasal cavity. The exposed area in FIG. 22 using the nebulizer 25 is significantly larger with more absorption area. Most notably, the drug penetrated the ethmoid and sphenoid sinuses. The drug delivered through the nebulizer 25 and via the BT did provide a path to the throat.

All of these features have been built into the device for use as a nasal nebulizer for the treatment of chronic sinusitis, allergic rhinitis, colds and flu, pain relief and for any developments in which introduction of drugs via the nasal passages will be aided. In one potential embodiment the nebulizer 25 will be used to deliver various medicaments with a narrow range of particle sizes.

I claim:

1. A nebulizer suitable for topical drug delivery to, or systemic drug delivery via, a deep nasal cavity or paranasal sinus, comprising:
   a nasal adapter having nasal proximal and nasal distal ends, and having at least one nasal adapter channel communicating between an aperture in the nasal-proximal end and an aperture in the nasal-distal end;
   a particle dispersion chamber, integral or in direct communication with the nasal adapter, and comprising: a dispersion chamber wall having an external and an internal surface, the internal surface defining at least one internal dispersion channel communicating between input and output ends of the particle dispersion chamber, and a directed compressed fluid output channel in communication with the internal dispersion channel directing output at an acute forward angle with respect to the output end of the particle dispersion chamber, wherein the fluid output, when fluid flows therefrom, is operative to impart a vortical flow to aerosolized particles exiting the particle dispersion chamber;
   a nebulizing chamber, integral or in direct communication with the particle dispersion chamber, and comprising a nebulizing chamber wall and nebulizing means with at least one pressure release orifice suitable to produce a nebulized particle stream;
   a nebulizing pressure feed having a compressor channel in communication with the pressure release orifice of the nebulizing chamber; and
   a dispersion feed channel communicating between the nebulizing pressure feed and the directed compressed fluid output channel of the particle dispersion chamber, the nebulizer configured to deliver a vortical particle flow of nebulized particles exiting the nasal adaptor.

2. The nebulizer of claim 1, wherein the compressed fluid output channel is integral with the dispersion chamber wall.

3. The nebulizer of claim 1, wherein the nasal adapter channel comprises the internal dispersion channel, and the directed compressed fluid output channel communicates with the nasal adaptor channel.

4. The nebulizer of claim 1, comprising a plurality of compressed fluid output channels in communication with at least one dispersion feed channel.

5. The nebulizer of claim 1, wherein the dispersion feed channel is integral with at least one of the nebulization chamber wall and the dispersion chamber wall.

6. The nebulizer of claim 1, comprising: a single nebulizer pressure release orifice; and dual internal dispersion channels comprising corresponding dual nasal adapter channels.

7. The nebulizer of claim 1, comprising: dual nebulizer pressure release orifices; and dual internal dispersion channels comprising corresponding dual nasal adapter channels.

8. The nebulizer of any one of claim 6 or 7, wherein the dispersion chamber is suitable to provide for independent vortical flow patterns within each of the dual internal dispersion channels.

9. The nebulizer of claim 8, wherein the dispersion chamber is suitable to provide for dual vortical flow patterns that spiral in opposite directions.

10. The nebulizer of claim 1, comprising jet nebulization means.

11. The nebulizer of claim 1, comprising linear nebulization means.

12. The nebulizer of claim 1, further comprising a supplementary inhalation channel integral to or in direct communication with the nasal adapter, the supplementary inhalation channel at one end in communication with ambient air, the other end being positioned adjacent to and in communication with the perimeter of the nasal-proximal aperture of the adapter channel.

13. The nebulizer of claim 12, wherein the nasal-proximal end of the supplementary inhalation channel is annular, positioned adjacent to and surrounding the perimeter of the nasal-proximal aperture of the adapter channel, and is suitable to provide for a supplementary air curtain, substantially adjacent to and surrounding the dispersed flow of delivered nebulized particles, to stretch and increase the vorticity of the vortical flow.

14. The nebulizer of claim 13, wherein the nebulized particles are delivered in a vortical flow, and wherein, upon supplemental inhalation, the air curtain provides sufficient convective draft to stretch and increase the vorticity of the vortical flow.

15. The nebulizer of claim 1, further comprising a supplementary inhalation channel integral to or in direct communication with the nasal adapter, the supplementary inhalation channel at one end in communication with ambient air, the other end being annularly positioned at the nasal distal end of the adapter channel to direct a supplementary air flow in an annual curtain, adjacent to the internal wall of the nasal adapter channel, to stretch and increase the vorticity of the vortical flow.

16. The nebulizer of claim 1, wherein the substantial mean diameter of the particle size is selected from the group consisting of about 2 to about 50 µm, about 5 to about 50 µm, about 5 to about 40 µm, about 5 to about 35 µm, about 5 to about 30 µm, about 5 to about 20 µm, about 5 to about 17 µm, about 5 to about 15 µm, about 8 to about 30 µm, about 8 to about 25 µm, about 8 to about 20 µm, about 10 to about 30 µm, about 10 to about 25 µm, about 10 to about 20 µm, about 10 to about 17 µm, about 10 to about 15 µm, about 11 to about 40 µm, about 11 to about 30 µm, about 11 to about 20 µm, about 11 to about 15 µm, about 12 to about 17 µm, about 15 to about 25 µm, about 15 to about 20 µm, and about 17 to about 23 µm.

17. The nebulizer of claim 16, wherein the substantial mean diameter of the particle size is selected from the group consisting of about 5 to about 30 µm, about 8 to about 25 µm, about 10 to about 20 µm, about 10 to about 17 µm, about 10 to about 15 µm, and about 12 to about 17 µm.

18. The nebulizer of claim 17, wherein the substantial mean diameter of the particle size is selected from the group consisting of about 8 to about 25 µm, about 10 to about 15 µm, or about 12 to about 15 µm.

19. The nebulizer of claim 18, wherein the substantial mean diameter of the particle size is about 8 to about 25 µm.

20. The nebulizer of claim 1, further comprising: an adapter cartridge receiving portion in communication with the nebulizing means; an adapter cartridge, and a medicament ampoule functionally complementary to the adapter cartridge.

21. A method of drug delivery to a deep nasal cavity or paranasal sinus of a subject, comprising:

producing, in a nebulizing chamber, nebulized particles substantially having a uniform mean diameter selected from the group consisting of about 5 to about 30 μm, about 8 to about 25 μm, about 10 to about 20 μm, about 10 to about 17 μm, about 10 to about 15 μm, and about 12 to about 17 μm, wherein; and passing the nebulized particles, prior to delivery to a subject, through a particle dispersion chamber comprising a directed compressed fluid output channel in communication with an internal dispersion channel directing output at an acute forward angle with respect to the output end of the particle dispersion chamber, wherein the fluid output, when fluid flows therefrom, is operative to impart a vortical flow to aerosolized particles exiting the particle dispersion chamber, wherein providing a nebulizing pressure feed having a compressor channel in communication with the nebulizing chamber and a dispersion feed channel communicating between the nebulizing pressure feed and the directed compressed fluid output channel of the particle dispersion chamber, the nebulizer delivers a vortical flow of nebulized particles to a deep nasal cavity or paranasal sinus of the subject.

22. The method of claim 21, wherein the nebulized particles substantially have a uniform mean diameter of about 8 to about 25 μm.

23. The method of claim 21, wherein at least 60% of the nebulized particles are of the uniform mean diameter range.

24. The method of claim 23, wherein at least 70of the nebulized particles are of the uniform mean diameter range.

25. The method of claim 21, wherein the particle dispersion chamber comprises dual dispersion channels and provides for dual provides for dual vortical particle flow patterns targeted to corresponding nostril apertures of the user.

26. The method of claim 25, wherein the dual vortical particle flow patterns are in opposite directions.

* * * * *